(12) United States Patent
Årstad et al.

(10) Patent No.: US 6,548,042 B2
(45) Date of Patent: Apr. 15, 2003

(54) BIS-PHOSPHONATE COMPOUNDS

(76) Inventors: Erik Årstad, Oslo University, Forskningsparken AS, Gaustadallèen 21, N-0349 (NO); Lars Skattebøl, Oslo University, Forskningsparken AS, Gaustadallèen 21, N-0349 (NO)

( * ) Notice: Subject to any disclaimer, the term of this patent is extended or adjusted under 35 U.S.C. 154(b) by 0 days.

(21) Appl. No.: 09/901,862

(22) Filed: Jul. 9, 2001

(65) Prior Publication Data
US 2002/0042539 A1 Apr. 11, 2002

Related U.S. Application Data

(63) Continuation-in-part of application No. 09/678,903, filed on Oct. 4, 2000.

(30) Foreign Application Priority Data

Aug. 7, 2000 (GB) .............................................. 0019377

(51) Int. Cl.$^7$ .............................................. A61K 51/00
(52) U.S. Cl. ...................... 424/1.77; 534/10; 534/14; 514/102
(58) Field of Search .......................... 424/1.77; 562/20, 562/21, 11, 12, 13, 14; 514/102; 534/14, 10

(56) References Cited

U.S. PATENT DOCUMENTS

| | | | | |
|---|---|---|---|---|
| 3,974,268 A | * | 8/1976 | Subramanian et al. | 250/303 |
| 4,440,738 A | * | 4/1984 | Fawzi et al. | 252/397 |
| 4,446,123 A | * | 5/1984 | Woo | 424/1.65 |
| 4,515,766 A | * | 5/1985 | Castronovo et al. | 424/1.77 |
| 4,830,847 A | | 5/1989 | Benedict et al. | |
| 4,857,513 A | | 8/1989 | Oku et al. | |
| 4,880,007 A | | 11/1989 | Sadler et al. | |
| 5,236,695 A | | 8/1993 | Winchell et al. | |
| 5,391,743 A | | 2/1995 | Ebetino et al. | |
| 5,618,804 A | | 4/1997 | Kawabe et al. | |
| 5,683,992 A | | 11/1997 | Kawabe et al. | |
| 5,876,693 A | * | 3/1999 | Katti et al. | 424/1.65 |
| 6,214,812 B1 | * | 4/2001 | Karpeisky et al. | 514/107 |

FOREIGN PATENT DOCUMENTS

| | | |
|---|---|---|
| EP | 485026 A2 | 5/1992 |
| GB | 2331459 A | 5/1999 |
| WO | WO 94/20508 | 4/1994 |
| WO | WO 95/11029 | 4/1995 |
| WO | WO 96/39150 | 12/1996 |

OTHER PUBLICATIONS

CA:106:115760 abs of Radioakt Isot Klin Forsch by Eisenhut et al 17(1) pp 461–467 1986.*
CA:131:144503 abs of Nuclear Medicine and Biology by Murd et al 26(4) pp 397–403 1999.*
CA:131:144503 abs Nuclear Medicine and Biology by Murud et al 26(4) pp 397–403 1999.*
CA:102:92166 abs J Nucl Med by Eisenhut 25(12) pp 1356–1361 1984.*
CA:105:221858 abs of Appl Radiat Isot by Eisenhut 37(8) pp 741–747 1986.*
CA:112:76495 abs of Nuklearmedizin Suppl (Stuttgart) 25( Trends and Possibilities Nucl. Med) by Terriere et al pp148–150 1989.*
CA:135:73471 abs of Journal of Medicinal by Zhuang et al 44(12) pp 1905–1914 2001.*
CA:107:150420 abs of Appl Radiat Isot by Eisenhut et al 38(7) pp 535–540 1987.*
Eisenhut, M., et al., Appl. Radiat. Isot. 38: 535–540 (1987).
Larsen, R.H., et al., J. Nuc. Med. 40: 1197–1203 (1999).

* cited by examiner

Primary Examiner—Jean F. Vollano
(74) Attorney, Agent, or Firm—Mary M. Krinsky

(57) ABSTRACT

The present invention provides a pharmaceutical compound, or pharmaceutically acceptable salt thereof, for use in medicine, wherein said compound is of formula I R—Ar—X—Y    I wherein
R is a pharmaceutically active moiety;
Ar is an aromatic moiety;
X is a linker group; and
Y is a moiety comprising two phosphonate groups.

Further aspects of the invention relate to a method for palliative and curative treatment of bone disorders and cancer related disorders, such as breast cancer.

22 Claims, 21 Drawing Sheets

2h

3h

4d

5x

Reagents and conditions:

a) i) Mg, THF, rfx; ii) TMSCl; b) NBS, $CCl_4$; c) Lithium diethyl methylenephosphonate, THF; d) Butyllithium, diethyl chlorophosphate, THF; e) TMSBr; f) aq. EtOH, NaOH

Reagents and conditions:
a) aq. KCN, Bu$_3$N; b) i) NaOH, MeOH; ii) H$_2$O, H$^+$; c) SOCl$_2$;
d) Trimethylphospite, THF, ultrasound; e) Dimethylphosphite, BuNH, 1:1 Et$_2$O:hexane; f) TMSBr; g) aq. EtOH, NaHCO$_3$

2g, 3g                                  2h, 3h

R = H for 2g/2h and R = OH for 3g/3h

Reagents and conditions:
a) Na$^{131}$I, NCS, 9:1 TFA:AcOH, 5 min, room temp.

Figure 5A (30 min)

Figure 5B (2 hrs)

(5 hrs)

(24 hrs)

Figure 7
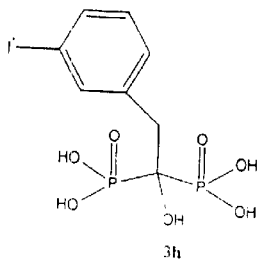
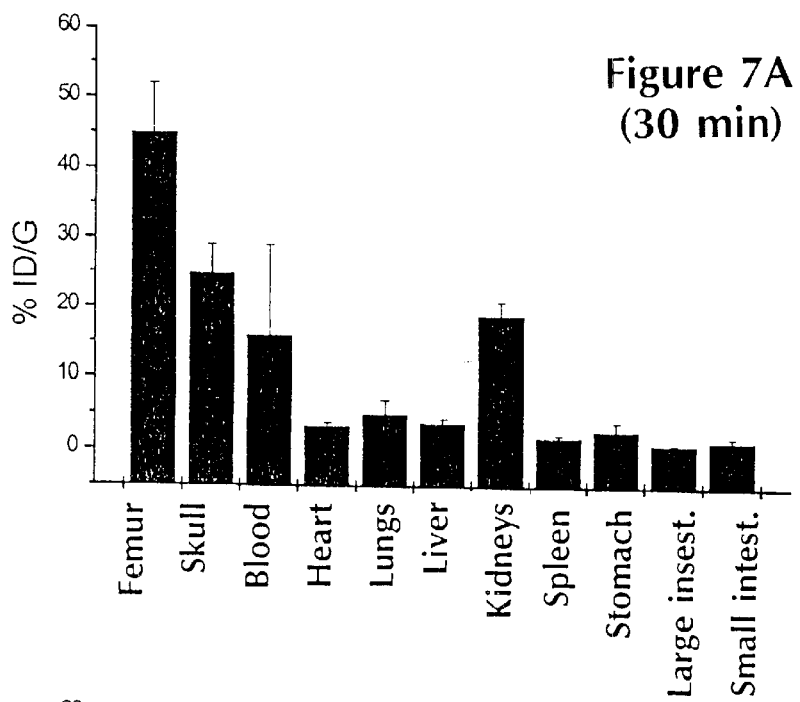
Figure 7A
(30 min)
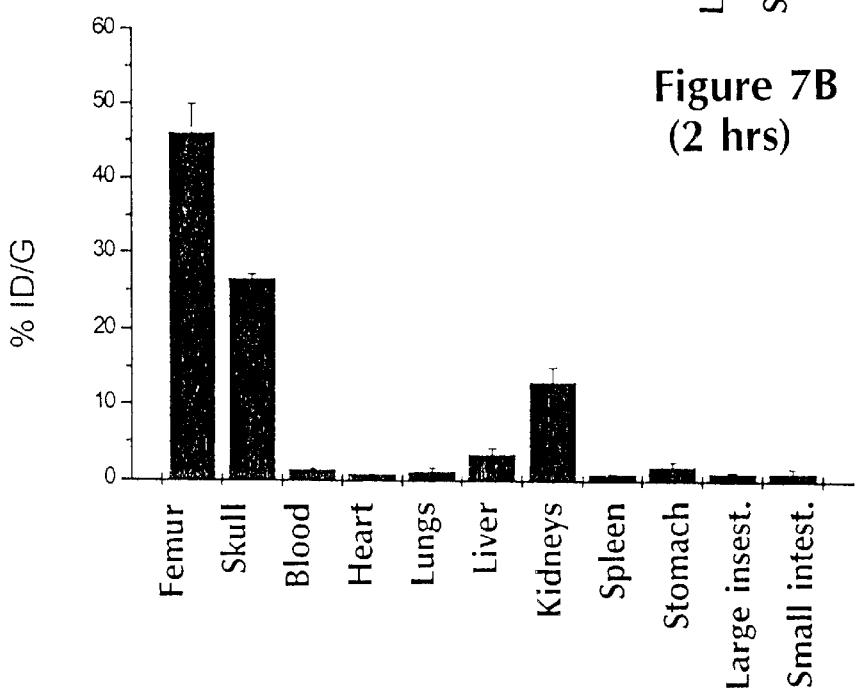
Figure 7B
(2 hrs)

(5 hrs)

(24 hrs)

Table 4: Biodistributions of 31a in balb/c mice (16-18 g) expressed as % injected dose per gram tissue (% ID/g).

| Organ | 0.25 h | 2 h | 5 h | 24 h |
|---|---|---|---|---|
| Femur | 5.88 ± 1.71 | 3.32 ± 0.74 | 2.78 ± 0.32 | 2.05 ± 0.49 |
| Skull | 3.38 ± 1.18 | 2.45 ± 0.48 | 1.98 ± 0.35 | 1.22 ± 0.19 |
| Blood | 2.46 ± 1.18 | 0.15 ± 0.04 | 0.04 ± 0.01 | 0.01 ± 0.01 |
| Heart | 0.94 ± 0.47 | 0.09 ± 0.03 | 0.05 ± 0.01 | 0.01 ± 0.01 |
| Lungs | 1.77 ± 0.71 | 0.31 ± 0.13 | 0.11 ± 0.02 | 0.02 ± 0.01 |
| Liver | 1.72 ± 0.59 | 0.17 ± 0.05 | 0.05 ± 0.01 | 0.02 ± 0.01 |
| Kidneys | 34.53 ± 9.06 | 2.24 ± 0.56 | 0.66 ± 0.05 | 0.08 ± 0.02 |
| Spleen | 0.63 ± 0.32 | 0.12 ± 0.02 | 0.06 ± 0.02 | 0.01 ± 0.01 |
| Stomach | 1.33 ± 0.69 | 0.52 ± 0.32 | 0.19 ± 0.08 | 0.01 ± 0.01 |
| Lg. Int. | 0.61 ± 0.27 | 0.34 ± 0.15 | 0.04 ± 0.01 | 0.01 ± 0.01 |
| Sm. Int. | 1.01 ± 0.49 | 0.15 ± 0.06 | 0.06 ± 0.01 | 0.01 ± 0.01 |
| Thyroid* | 0.11 ± 0.06 | 0.13 ± 0.03 | 0.14 ± 0.03 | 0.13 ± 0.03 |

*Values expressed as % of injected dose.

*Table 5: Biodistributions of 34a in balb/c mice (20-25 g), expressed as % injected dose per gram tissue (% ID/g).*

| Organ | 0.5 h | 2 h | 5 h | 24 h |
|---|---|---|---|---|
| Femur | 18.80 ± 0.51 | 21.16 ± 3.85 | 10.00 ± 7.81 | 15.25 ± 4.89 |
| Skull | 10.28 ± 2.58 | 7.64 ± 3.53 | 6.16 ± 4.82 | 7.13 ± 2.73 |
| Blood | 2.22 ± 0.31 | 0.31 ± 0.25 | 0.11 ± 0.09 | 0.03 ± 0.01 |
| Heart | 0.90 ± 0.15 | 0.26 ± 0.08 | 0.07 ± 0.05 | 0.04 ± 0.02 |
| Lungs | 1.00 ± 0.12 | 0.35 ± 0.05 | 0.10 ± 0.08 | 0.06 ± 0.03 |
| Liver | 2.98 ± 0.65 | 2.14 ± 0.11 | 0.94 ± 0.70 | 0.23 ± 0.02 |
| Kidneys | 8.23 ± 6.39 | 3.68 ± 2.80 | 2.26 ± 1.64 | 1.06 ± 0.10 |
| Spleen | 0.35 ± 0.26 | 0.26 ± 0.07 | 0.12 ± 0.09 | 0.10 ± 0.03 |
| Stomach | 1.14 ± 0.88 | 1.12 ± 0.50 | 0.23 ± 0.18 | 0.05 ± 0.03 |
| Lg. Int. | 0.37 ± 0.29 | 0.28 ± 0.05 | 0.24 ± 0.17 | 0.28 ± 0.30 |
| Sm. Int. | 0.53 0.04 | 0.33 ± 0.02 | 0.15 ± 0.12 | 0.04 ± 0.01 |
| Thyroid* | 0.21 ± 0.09 | 0.14 ± 0.05 | 0.06 ± 0.01 | 0.02 ± 0.01 |

*Values expressed as % of injected dose.

Table 6: Biodistributions of 46a in balb/c mice (20-25 g), expressed as % injected dose per gram tissue (% ID/g).

| Organ | 0.5 h | 2 h | 5 h | 24 h |
|---|---|---|---|---|
| Femur | 45.03 ± 6.75 | 45.54 ± 4.10 | 30.30 ± 8.90 | 37.79 ± 11.78 |
| Skull | 24.61 ± 3.85 | 26.49 ± 0.61 | 19.14 ± 8.61 | 21.34 ± 5.62 |
| Blood | 15.92±12.75 | 1.36 ± 0.25 | 0.82 ± 0.19 | 0.09 ± 0.03 |
| Heart | 3.35 ± 0.41 | 0.82 ± 0.21 | 0.40 ± 0.17 | 0.18 ± 0.07 |
| Lungs | 5.41 ± 1.67 | 1.20 ± 0.48 | 0.61 ± 0.05 | 0.54 ± 0.36 |
| Liver | 3.88 ± 0.49 | 3.36 ± 0.67 | 2.51 ± 0.07 | 2.27 ± 0.69 |
| Kidneys | 18.64 ± 1.78 | 13.30 ± 1.70 | 7.17 ± 0.25 | 5.16 ± 2.00 |
| Spleen | 2.02 ± 0.357 | 0.77 ± 0.07 | 0.47 ± 0.06 | 0.49 ± 0.20 |
| Stomach | 3.22 ± 1.06 | 1.79 ± 0.64 | 0.38 ± 0.13 | 0.13 ± 0.01 |
| Lg. Int. | 1.07 ± 0.06 | 1.00 ± 0.20 | 0.45 ± 0.06 | 0.16 ± 0.05 |
| Sm. Int. | 1.58 ± 0.50 | 1.04 ± 0.70 | 0.39 ± 0.09 | 0.16 ± 0.05 |
| Thyroid* | 0.51 ± 0.19 | 0.19 ± 0.08 | 0.49 ± 0.11 | 0.06 ± 0.04 |

*Values expressed as % of injected dose.

Table 7: Biodistributions of 67a and 72a in balb/c mice (20-25 g), expressed as % injected dose per gram tissue (% ID/g).

| Organ | 67a, 24 h | 72a, 24 h |
|---|---|---|
| Femur | 1.39 ± 0.43 | 8.84 ± 0.97 |
| Skull | 0.91 ± 0.08 | 10.36 ± 4.26 |
| Blood | 0.18 ± 0.04 | 0.02 ± 0.02 |
| Heart | 0.19 ± 0.08 | 0.06 ± 0.00 |
| Lungs | 0.67 ± 0.19 | 0.21 ± 0.02 |
| Liver | 5.57 ± 0.79 | 0.35 ± 0.06 |
| Kidneys | 0.40 ± 0.10 | 0.85 ± 0.08 |
| Spleen | 2.49 ± 0.37 | 0.17 ± 0.04 |
| Stomach | 0.07 ± 0.04 | 0.04 ± 0.01 |
| Lg. Int. | 0.10 ± 0.03 | 0.05 ± 0.01 |
| Sm. Int. | 0.08 ± 0.02 | 0.05 ± 0.01 |
| Thyroid* | 0.02 ± 0.01 | 0.02 ± 0.01 |

*Values expressed as % of injected dose.

Table 8: Biodistributions of HPLC-purified (HP) and nonpurified (NP) 46a in nude rats (60 g), expressed as % injected dose per gram tissue (% ID/g).

| Organ | HP, 24 h | NP, 24 h |
|---|---|---|
| Femur | 16.44 ± 1.96 | 5.28 ± 1.10 |
| Skull | 5.84 ± 0.35 | 0.79 ± 1.16 |
| Blood | 0.01 ± 0.01 | 0.13 ± 0.08 |
| Heart | 0.04 ± 0.02 | 0.09 ± 0.03 |
| Lungs | 0.05 ± 0.01 | 0.12 ± 0.04 |
| Liver | 0.18 ± 0.03 | 0.23 ± 0.04 |
| Kidneys | 0.36 ± 0.03 | 0.37 ± 0.03 |
| Spleen | 0.09 ± 0.01 | 0.19 ± 0.07 |
| Stomach | 0.05 ± 0.01 | 0.16 ± 0.10 |
| Lg. Int. | 0.03 ± 0.01 | 0.29 ± 0.25 |
| Sm. Int. | 0.03 ± 0.01 | 0.05 ± 0.01 |
| Thyroid* | 0.02 ± 0.01 | 0.03 ± 0.01 |

*Values expressed as % of injected dose.

BIS-PHOSPHONATE COMPOUNDS

CROSS-REFERENCES TO RELATED APPLICATIONS

This application is a continuation-in-part of co-pending U.S. Ser. No. 09/678,903, filed Oct. 4, 2000, which claimed benefit of United Kingdom application number 0019377.1, filed Aug. 7, 2000.

STATEMENT REGARDING FEDERALLY SPONSORED RESEARCH

Not Applicable.

BACKGROUND OF THE INVENTION

1. Field of the Invention

The present invention relates to a pharmaceutical compound and composition for use in medicine.

2. Description of the Related Art

It is well known in the art that phosphonate compounds, for example bisphosphonates, have a high affinity for hydroxyapatite crystals and thus tend to localise in vivo in regions of bone metabolism. Moreover, it has also been established that phosphonate compounds are generally low in toxicity.

U.S. Pat. No. 4,880,007 (Amersham International PLC) discloses complexes formed between (a) an amino di- or polyphosphonate; and (b) a paramagnetic metal ion, such as gadolinium (III). Such complexes exhibit calcified tissue seeking properties which render them useful as contrast agents for investigating bone metabolism by NMR scanning.

Similarly, U.S. Pat. No. 5,236,695 (Concat Ltd.) discloses polyphosphonate ligands containing three or more phosphonate groups, combined with paramagnetic metal cations which are administered in the form of pharmacologically acceptable salts. Such compounds are useful as MRI contrast agents which tend to localise in bone tissue without being conjugated to bone-specific biomolecules.

Bisphosphonates have also been used in combination with technetium-99 (Tc-99m). Indeed, Tc-99m is routinely used with carriers such as methylene bisphosphonate, for imaging in hospitals. Furthermore, U.S. Pat. No. 4,830,847 discloses diphosphonate-derivatised macromolecules, such as proteins, suitable for use as technecium-99m based scanning agents and anticalcification agents. Typically, the scanning agents are prepared by combining Tc-99m in a 3+, 4+ and/or 5+ oxidation state with the disphosphonate-derivatised macromolecule. Also disclosed are pharmaceutical compositions containing such diphosphonate-derivatised macromolecules.

The therapeutic applications of bisphosphonate compounds are also well documented in the art. For example, WO 96/39150 (Merck & Co., Inc.) discloses the use of bisphosphonates, such as alendronate, in the prevention or treatment of bone loss associated with rheumatoid arthritis. Similarly, GB 2,331,459 (SPA) discloses an injectable composition for treating skeletal and bone disorders which comprises a bisphosphonate in combination with a benzyl alcohol. Eisenhut et al. (Appln. Radiat. Isot., Vol 38, No.7, ps35–540) disclose the use of $^{131}$I-labelled benzylidine-diphosphonates for the palliative treatment of bone metastases. Finally, WO 95/11029 (Merck & Co., Inc.) discloses compositions comprising bisphosphonate and growth hormone secretagogues, which are useful for reducing the deleterious effects of osteoporosis in elderly patients.

The present invention seeks to provide improved phosphonate compounds for use in medicine. In particular, the invention seeks to provide pharmaceutical compounds which exhibit improved activity in the palliative and curative treatment of bone disorders, and/or which may also be suitable for use in medical imaging techniques.

SUMMARY OF THE INVENTION

Aspects of the invention are presented in the accompanying claims and in the following description.

In the broadest aspect, the present invention relates to a pharmaceutical compound for use in medicine. The pharmaceutical may be for a therapeutic use and/or a diagnostic use.

More specifically, the present invention provides a pharmaceutical compound, or pharmaceutically acceptable salt thereof, for use in medicine, wherein said compound is of formula I $$R-Ar-X-Y$$

wherein

R is a pharmaceutically active moiety;

Ar is an aromatic moiety;

X is a linker group; and

Y is a moiety comprising two phosphonate groups.

In a preferred aspect of the invention, Y comprises a geminal bisphosphonate group.

In a further preferred aspect, the invention provides a pharmaceutical compound, or pharmaceutically acceptable salt thereof, of formula II $$R-Ar-X-\underset{Z}{\overset{PO_3H_2}{\underset{}{\bigg\langle}}}PO_3H_2 \qquad \text{II}$$

wherein Z is H, $NH_2$ or an oxy substituent. Preferably, Z is H or OH.

The pharmaceutical compound of the present invention comprises a linker group, X.

In a preferred aspect, the linker group of the invention is a substituted or unsubstituted $C_{1-4}$ alkylene group.

In an alternative preferred aspect of the invention, X is a $C_{1-4}$ amine group, $C_{1-4}$ ether group or a $C_{1-4}$ thioether group, each of which may be substituted or unsubstituted.

In another preferred aspect of the invention, X is S=O or $SO_2$.

Where X is substituted, suitable substituents include one or more groups which do not interfere with the pharmaceutical activity of the compound in question. Exemplary non-interfering substituents include hydroxy, amino, halo, alkoxy, and alkyl.

The pharmaceutical compound of the present invention also comprises an aromatic moiety, Ar.

Preferably, the aromatic moiety of the compound is electron deficient.

In a more preferred aspect, the aromatic moiety of the invention is a single aromatic ring. However, other aromatic moieties are also suitable for use in the invention, for example, aromatic moieties comprising more than one aromatic ring, where the aromatic rings may be fused together or joined via one or more suitable spacer groups Examples of aromatic moieties suitable for the present invention include substituted or unsubstituted phenyl, naphthyl, thiophenyl, furyl, pyridyl and pyrrole groups.

Where the aromatic moiety is substituted, suitable substituents include one or more groups which do not interfere with the pharmaceutical activity of the compound in question. Exemplary non-interfering substituents include hydroxy, amino, halo, alkoxy, and alkyl.

The pharmaceutical compound of the present invention also comprises a pharmaceutically active moiety, R.

In a preferred aspect, R comprises a radiolabel. Examples of radiolabels suitable for use in the present invention include $^{124}$I, $^{125}$I, $^{131}$I, $^{211}$At (an α-emitter), $^{186}$Re, Tc-99m, and β-emitting bromine nuclei.

In an alternative preferred aspect, the pharmaceutically active moiety of the invention may comprise a functional group (or ligand) to which a metal ion can be chelated, or is chelated thereto. Species of the former type, i.e. those comprising a functional group to which a metal ion can be chelated, could be potentially useful for complexing any excess radiolabel close to the bone, thereby preventing radiolabel poisoning.

By way of definition, the term "chelate" refers to a complex in which a ligand is coordinated to a metal ion at two or more points, so that there is a ring of atoms including the metal, and where the term "ligand" refers to an ion or molecule that can donate a pair of electrons to said metal ion.

Suitable functional groups or ligands to which a metal ion may be chelated include amine, hydroxy, or carboxylic acid moieties.

In a particularly preferred aspect, the metal ion chelated to the functional group is paramagnetic. In the present context, the term "paramagnetic" refers to metal ions having net orbital or spin magnetic moments that are capable of being aligned in the direction of an applied magnetic field. Such atoms have a positive (but small) susceptibility and a relative permeability slightly in excess of one. Paramagnetism occurs in all atoms with unpaired electrons, e.g. transition metal ions with unpaired electron shells.

Examples of suitable paramagnetic metals include those of the lanthanide elements with atomic numbers 58 to 70, and those of the transition metals with atomic numbers 21 to 29, 42 and 44. Typical examples include chromium (III), manganese (II), iron (II), iron (III), cobalt (II), nickel (II), copper (II), praesodymium (III), neodymium (III), samarium (III), gadolinium (III), terbium (III), dysprosium (III), holmium (III), erbium (III) and ytterbium (III).

The pharmaceutically active moiety, R, may also comprise a paramagnetic component other than a paramagnetic ion, for example, a moiety comprising the group NO.

Compounds of the invention containing paramagnetic moieties or radiolabels may have applications in the field of medical imaging, especially calcified tissue imaging. In particular, such compounds may be administered to a patient in order to preferentially enhance the NMR image contrast in tissue. By way of definition, the term "NMR" also encompasses magnetic resonance imaging (MRI) in which images of tissue are produced by magnetic resonance techniques.

Thus, in one preferred aspect, the invention provides a pharmaceutical carrier molecule for a radiolabel. In a particularly preferred aspect, the radiolabel is Tc-99m.

The term "calcified tissue" refers to bone, regions of bone metabolism, regions of calcified tumours and other diseased tissues.

In a particularly preferred aspect of the invention, the pharmaceutically active moiety R is attached directly to the aromatic moiety, Ar.

By way of definition, the term "pharmaceutically acceptable salt" includes any salt that has the same general pharmacological properties as the parent species from which it is derived, and which is acceptable from a toxicity view-point. Typical pharmaceutically acceptable salts include acid addition salts, base salts or solvates or hydrates thereof. A review of suitable salts may be found in Berge et al., J. Pharm. Sci., 1977, 66, 1–19.

Suitable acid addition salts are formed from acids which form non-toxic salts. Examples include hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethane-sulphonate, benzenesulphonate, p-toluenesulphonate and pamoate salts.

Suitable base salts are formed from bases which form non-toxic salts and examples include alkali metal (sodium and potassium), alkaline earth metal (calcium and magnesium), aluminium, non-toxic heavy metal (zinc, stannous and indium), ammonium and low molecular weight substituted ammonium (mono-, di- and triethanolamine) salts.

Methods for preparing pharmaceutically acceptable salts of compounds of the invention will be familiar to those skilled in the art. Typically, pharmaceutically acceptable salts may be prepared by mixing together a solution of the agent and the desired acid or base, as appropriate. The salt may be recovered by evaporation of the solvent, or by precipitation from solution followed by filtration.

The compound of the present invention may exist in polymorphic form.

The compound of the present invention may contain one or more asymmetric carbon atoms and thus may exist in two or more stereoisomeric forms. The present invention includes the individual stereoisomers of the compound and, where appropriate, the individual tautomeric forms thereof, together with mixtures thereof.

Diastereoisomers of compounds of the invention may be separated by conventional techniques such as fractional crystallisation, chromatography or H.P.L.C. of a stereoisomeric mixture of the agent or a suitable salt or derivative thereof. Individual enantiomers of the agent may also be prepared from the corresponding optically pure intermediate or by resolution, such as by H.P.L.C. of the corresponding racemate using a suitable chiral support. Alternatively, individual enantiomers may be prepared by fractional crystallisation of the diastereoisomeric salts formed by reaction of the corresponding racemate with a suitable optically active acid or base, as appropriate.

The present invention also includes all suitable isotopic variations of the compound, or pharmaceutically acceptable salts thereof. The term "isotopic variation" as used herein refers to a compound in which at least one atom is replaced by an atom having the same atomic number but an atomic mass different from the atomic mass usually found in nature. Examples of isotopes that can be incorporated into the compounds of the invention, or pharmaceutically acceptable salts thereof, include isotopes of hydrogen, carbon, nitrogen, oxygen, phosphorus, sulphur, fluorine and chlorine such as $^{2}$H, $^{3}$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Isotopic variants in which a radioactive isotope is incorporated may have applications in drug and/or substrate tissue distribution studies. Typical examples preferred for their ease of preparation and detectability include tritium ($^{3}$H), and carbon-14 ($^{14}$C) isotopes. Substitution with other isotopes such as deuterium ($^{2}$H) may afford certain therapeutic advantages resulting from greater metabolic stability, i.e., increased in vivo half-life or reduced dosage requirements. Isotopic variations of the agent of the present invention and pharmaceutically acceptable salts thereof of this invention can generally be prepared by conventional procedures familiar to those skilled in the relevant art using the appropriate isotopic variations of suitable reagents.

It will be appreciated by those skilled in the art that the compound of the present invention may be derived from a prodrug. By way of example, a prodrug includes any entity having one or more protected group(s) and which may not possess pharmacological activity per se, but may, in certain instances, be administered (for example orally or parenterally) and thereafter metabolised in the body to form the pharmaceutically active agent of the present invention.

The skilled person in the art will further appreciate that certain moieties known as "pro-moieties", for example as described in "Design of Prodrugs" by H. Bundgaard, Elsevier, 1985 (the disclosured of which is hereby incorporated by reference), may be placed on appropriate functionalities of the compounds. Such prodrugs are also intended to fall within the scope of the present invention.

The present invention also provides a pharmaceutical composition comprising the compound provided by the present invention admixed with a pharmaceutically acceptable carrier, diluent, or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant (s), suspending agent(s), coating agent(s), solubilising agent (s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

The composition/formulation requirements may vary depending on the delivery systems. By way of example, the pharmaceutical composition of the present invention may be formulated to be delivered using a mini-pump or by a mucosal route, for example, as a nasal spray or aerosol for inhalation or ingestable solution. Alternatively, the composition may be formulated in an injectable form, for parenteral delivery, for example, by an intravenous, intramuscular or subcutaneous route. The formulation may also be formulated so as to be suitable for delivery by both routes.

Where the agent is to be delivered mucosally through the gastrointestinal mucosa, it should be able to remain stable during transit though the gastrointestinal tract; for example, it should be stable at acid pH, resistant to proteolytic degradation and to the detergent effects of bile.

The pharmaceutical compositions of the invention can be administered topically in the form of a lotion, solution, cream, ointment or dusting powder, or by the use of a skin patch. Alternatively, the compositions can be administered orally in the form of tablets containing excipients such as starch or lactose, or in capsules or ovules either alone or in admixture with excipients, or in the form of elixirs, solutions or suspensions containing flavouring or coloring agents, or in the form of a suppository or pessary. Further modes of administration include inhalation, or parenteral injection, for example intravenously, intramuscularly or subcutaneously. For parenteral administration, the compositions may be used in the form of a sterile aqueous solution which may contain other substances, for example appropriate levels of salts and/or monosaccharides to make the solution isotonic with blood. For buccal or sublingual administration the compositions may be administered in the form of tablets or lozenges which can be formulated in a conventional manner.

Typically, a physician will determine the actual dosage which will be most suitable for an individual patient and it will vary with the age, weight and response of the particular patient.

In a preferred aspect, the present invention relates to the use of the compound or composition of the invention in the palliative or curative treatment of bone disorders.

Preferably, the compounds and/or compositions of the invention are used to treat bone disorders that are cancer-related skeletal diseases, for example, skeletal metastases, osteoblastic osteosarcoma or multiple myelomas. However, the compounds and/or compositions of the invention may also be used to treat non-cancerous bone disorders, such as age-related bone loss, rheumatoid-related bone loss, or bone loss related to osteoporosis, disuse or steroid therapy.

The treatment of skeletal metastases is one of the main problems encountered in practical clinical oncology. It is estimated that up to 85% of all patients with advanced carcinomas to the breast, prostate or lung develop such metastatic conditions (Bijvoet, O. L. M., Fleisch, H. A., Bisphosphonate on Bones, Elsevier Science B.V., Amsterdam, 1995; pp. 349). Up to now, the prognosis for these patients has been poor.

To date, treatment methods in current clinical practice include external radiotherapy, hormone therapy and chemotherapy, although the number of patients achieving complete curation is negligible (Bijvoet, O. L. M., Fleisch, H. A., Bisphosphonate on Bones, Elsevier Science B.V., Amsterdam, 1995; pp. 350). In particular, severe side-effects often limit the applicability of these methods. Consequently, there is a strong need for improved therapeutic methods for slowing down tumour progression and for pain palliation.

Normally, the main method for radiation therapy is external beam irradiation. However, if there are multiple skeletal metastases present, a more efficient treatment may be the targeted radiotherapy of timorous osseous lesions by means of radioactive compounds with bone affinity. Such regions are characteristic for several types of bone-related diseases, malignant as well as benign. Examples of malignant lesions are skeletal metastases and osteosarcoma, examples of benign lesions are osteoporosis and Paget's disease (Bijvoet, O. L. M., Fleisch, H. A., Bisphosphonate on Bones, Elsevier Science B.V., Amsterdam, 1995; pp. 293). Pathological bone synthesis in skeletal metastases is observed in very large groups of cancer patients who develop metastatic foci originating from different types of soft-tissue tumours.

Furthermore, there is a small but important, clinically difficult niche of patients suffering from metastasised osteoblastic osteosarcoma. In this case, a primitive bone-like substance, osteoid, is produced by the tumour cells themselves. Although clinically very different from skeletal metastases, the chemistry of these lesions is similar, and they may often be targeted by the same type of bone affinity compounds.

Usually, myelotoxicity sets the limits for the radiation dose that can be administered to the tumour by means of radioactive bone-affinity compounds. Any development which decreases the radiation dose to the bone marrow would therefore substantially improve targeted radiotherapy techniques.

In a preferred aspect, the present invention thus seeks to provide improved bone affinity compounds which expose the bone marrow to substantially lower levels of radiation.

There are two classes of radioactive bone-affinity compounds currently in clinical use. The first and most important class includes ions of the radioisotopes of alkaline earth elements, such as $^{89}Sr^{2+}$, which is the most common bone-seeking agent in clinical use (Lewington, V. J., Cancer therapy using bone-seeking isotopes, Physics in Medicine and Biology, 1996; 41: 2031–2032).

The other class of bone-seeking compounds include radioactive bis- or polyphosphonic acids carrying a β-active radionuclide. The species most commonly used in the clinic are $^{186}Re$-HEDP (Lewington, V. J., Cancer therapy using bone-seeking isotopes, Physics in Medicine and Biology, 1996; 41: 2030) and $^{153}Sm$-EDTMP (Lewington, V. J., Cancer therapy using bone-seeking isotopes, Physics in Medicine and Biology, 1996; 41:2029). The latter has also been applied with success in the palliative treatment of osteoblastic osteosarcoma (Franzuis, C. et al., High Activity Samarium-153-EDTMP Therapy in Unresectable Osteosarcoma, Nuklearmedizin,1999; 38:337–340). However, in contrast to the compounds disclosed in the present invention, none of these nuclides reduce the tumour progression of small tumours, and hence they are not suitable for curative treatment.

β-emitters are usually classified into three groups according to β-particle energy and hence range. With regard to physical properties, β-particle energy and range are parameters which have to be matched to the size of the tumour. The half life and chemical properties, on the other hand, are related to the pharmacokinetics and metabolism of the carrier molecule. Radionuclides with β-energy in the range $E_{avg}$=0.08–0.18 MeV (mean range 0.4–0.9 mm) are best suited for treatment of small tumours (Zweit, J., Radionuclides and carrier molecules for therapy, Physics in Medicine and Biology, 1996; 41: 1908–1910). $^{311}I$ is the most familiar and the only radionuclide in this group that has been used clinically. Radionuclides with medium β-energy such as $^{153}Sm$ and $^{186}Re$ are less suitable for curative treatment, since the dose distribution will spare small tumours and the tumour on bone marrow ratio is too low. High energy β-emitters such as $^{89}Sr$ are only suited for the palliative and curative treatment of large tumours. There is speculation as to whether the use of α-emitters in combination with β-emitters would be superior for curative treatment. However, the short range of α-radiation (40–80 μm) would most likely require bonding of the α-emitting carrier molecule to most cancer cells within the tumour.

In an alternative aspect, the invention also relates to the use of the compound of the invention in the preparation of a medicament for the palliative or curative treatment of bone disorders.

As used herein the phrase "preparation of a medicament" includes the use of a compound of the invention directly as the medicament in addition to its use in a screening programme for the identification of further active agents or in any stage of the manufacture of such a medicament.

Such a screening programme may for example include an assay for determining whether a candidate substance is capable of mimicking the activity of a pharmaceutical compound of the present invention.

Another aspect of the invention provides a method of treating a subject in need of the palliative or curative treatment of bone disorders, the method comprising administering to said subject a therapeutically effective amount of the compound or composition of the present invention.

The present invention also provides a process for preparing a compound of the invention, wherein R comprises a radiolabel, said process comprising the following steps:

(i) preparing a phosphonate precursor comprising Ar, X and Y;

(ii) radiolabelling said bisphosphonate precursor.

In a preferred aspect, step (ii) of the above-mentioned process is a deiodosilylation reaction.

For practical purposes, it is desirable to produce targeting radionuclide agents at the site of use, e.g. hospitals.

To date, the demand for convenient labelling chemistry, high stability and favourable biological behaviour has proven difficult to meet with radiohalogenated bisphosphonates. In recent studies, pre-labelled compounds have been connected to bisphosphonic acid functionalities (Fritzberg, A. R. et al., U.S. Pat. No. 5,202,109: Conjugates for bone imaging and bone cancer therapy; Murud, k. et al., Synthesis, Purification, and in Vitro Stability of $^{211}At$- and $^{125}I$-Labeled Amidobisphosphonates; Nuclear Medicine and Biology, 1999, 26). Favourable results have been obtained with such radioconjugates. However, this strategy requires two reactions involving radioactivity and three purification steps to obtain the final product. When working with therapeutic doses of radioactivity such procedures are inappropriate in view of radiation safety standards. Up to now, no therapeutic experiments have been conducted with such radioconjugated bisphosphonic acids.

The present invention thus provides an improved labelling technique for bisphosphonic acids. More particularly, the invention focuses on precursors in which the label is incorporated in the final stages of the synthesis. The present process is therefore advantageous compared to the preparation of many of the radionucleotide agents currently in clinical use.

More specifically, the present invention employs trialkylarylsilyl precursors. These substances are easy to synthesise and appear to be very stable; moreover iododesilylation affords the radioiodinated bisphosphonic acids in very high yield. Dialkylaryltriazene precursors were also investigated, but labelling yields were lower, and the final purification was hampered by the presence of many side products.

From a chemical perspective, it is widely known that non-radioactive bisphosphonic acids may be used as pharmaceuticals for treating bone related disorders. By way of example, it is known that non-radioactive biphosphonates are biologically active molecules which are used to treat different clinical conditions, such as inhibitors of osteoporosis and as protectants against skeletal complications in cancer (see Larsen et al (1999 J Nucl Med 40: 1197). Therefore, in one broad aspect, the present invention relates to novel non-radioactive compounds of the present invention which may be used as pharmaceuticals for treating bone related disorders and cancer disorders. In this regard, the novel compounds of the present invention are acting as pharmaceutical compounds per se and not as carrier compounds for other pharmaceutically active moieties. Although it is known that other molecules linked to bisphosphonic acids may also affect bone affinity, it is the bisphosphonic acid functionality that is primarily responsible for the bone affinity of such molecules. This was the motivation for synthesising a series of radioiodinated aromatic bisphosphonic acids with different alpha functionalities and with various linker groups inserted between the aryl group and the bisphosphonic acid moiety (FIG. 1).

The synthesis of compound 2g is depicted in FIG. 2. The transformation of m-chlorotoluene (2a) to m-trimethylsilyltoluene (2b) by use of magnesium and trimethylchlorosilane in HMPTA is described in the literature (Effenberger, F. and Habich, D., Liebigs Ann. Chem., 1979, pp. 842–857). However, prolonged heating is required and the work-up uses large amounts of this strongly carcinogenic solvent. A second way of synthesising m-trimethylsilyltoluene is by reacting m-bromotoluene with molten sodium in toluene (Clark, H. A. et al., J. Am. Chem. Soc., 1951; 73:3798). However, this route is troublesome and hazardous. In contrast, by refluxing m-chlorotoluene with magnesium in THF followed by the addition of trimethylchlorosilane, m-trimethylsilyltoluene can be obtained in 88–90% yield. Trimethylsilyltoluene was then brominated with N-bromosuccinimide in carbon tetrachloride as described in the literature (Severson, R. G. et al., J. Am. Chem. Soc., 1957; 79:6540). The resulting m-trimethylsilylbenzyl bromide (2c) was reacted with the lithium ylide of diethyl methylenephosphonate providing diethyl m-trimethylsilylphenylethylidene-phosphonate (2d) in moderate yield. The phosphonate was then converted to the corresponding lithium ylide using butyllithium and the subsequent reaction with diethyl chlorophosphate gave the tetraethyl bisphosphonate 2e in high yield. Hydrolysis was achieved by trans-esterification to the corresponding tetramethylsilyl ester 2f, followed by the addition of aqueous ethanol. The bisphosphonic acid was isolated as the corresponding disodium salt 2g.

The synthesis of compound 3g is depicted in FIG. 3. m-Trimethylsilylbenzyl bromide (2c) was converted to tri-methylsilylbenzyl cyanide (3a) with potassium cyanide under phase transfer conditions. Hydrolysis to m-trimethylsilylphenylacetic acid (3b) was then achieved by refluxing the cyanide with sodium hydroxide in methanol. Overall yields in the range of 59–67% were obtained. The acid was then transformed to the acid chloride 3c employing thionyl chloride at ambient temperature. The ultrasound-assisted reaction of the acid chloride with trimethylphosphite afforded a cis/trans stereoisomeric mixture of the enolphosphonate 3d. The second phosphonate moiety was introduced by adding dimethylphosphite to the enolphosphonate under basic conditions. The corresponding tetramethyl bisphosphonate 3e was trans-esterified to the tetratrimethylsilyl ester 3f, which was subsequently hydrolysed by stirring with aqueous ethanol. The bisphosphonic acid was isolated as its disodium salt 3g.

Compounds 2g and 3g were labelled using an iododesilylation reaction (FIG. 4). This was achieved by adding n.c.a. (non carrier added) Na$^{131}$I and N-chlorosuccinimide as an oxidising agent to a solution of the precursor (2g, 3g) in a mixture of acetic acid and trifluoroacetic acid at room temperature. The yields obtained were greater than 95%, as measured by HPLC. The radioiodinated compounds were purified by HPLC and their structures were confirmed by coelution with the corresponding non-radioactive compounds.

Chemical and radiochemical purity is essential for the in vivo application of radiopharmaceuticals in man. Chemical purity demands the isolation of the radiolabelled compounds from all non-radioactive starting compounds and side-products. The bisphosphonates described in the present invention were all labelled with n.c.a. (non carrier added) radioiodine. Purification and confirmation of their structures was achieved by HPLC. The demand for a non-toxic mobile phase along with the complex aqueous chemistry of bisphosphonates made the development of HPLC systems problematic. In particular, bisphosphonates are apparently strongly associated in aqueous solutions and form clusters with a range of sizes all due to a single compound (Wiedmer, W. H. et al., Ultrafiltrability and Chromatographic Properties of Pyrophosphate, 1-Hydroxyethylidene-1,1-Bisphosphonate, Calcif. Tissue Int., 1983; 35:397–400). However, these problems were successfully solved for analytical and purification purposes, resulting in single peaks for each compound, whilst avoiding severe pressure build-up in the HPLC system With regard to biological activity, the success of radionuclide targeting therapy is strongly dependent on the following conditions:

i) choice of radionuclide;

ii) the ability of the targeting compound to home in on the target quickly and in high amounts;

iii) the retention time at the site;

iv) resistance towards degradation;

v) little accumulation in other organs.

Details of the biological activity of the compounds of the invention are discussed further in the Examples section below.

In summary, the biological results clearly indicate that the compounds disclosed herein exhibit superior properties to previously reported radiohalogenated bisphosphonic acids, in terms of bone affinity, selectivity, kinetics and stability in vivo. Moreover, the compounds of the invention are readily available and can be labelled in high yields by simple means from stable precursors With regard to cancer treatment, the compounds of the invention that are labelled with radioiodine have been shown to seek out the desired target quickly, selectively, and in extraordinarily high amounts. In addition, the compounds display resistance to enzymatic dehalogenation.

BRIEF DESCRIPTION OF DRAWINGS

The present invention will now be described only by way of example and with reference to the accompanying figures, wherein:

FIG. 11 also presents Table 4 which shows the biodistributions of 31a in balb/c mice (16–18 g) expressed as % injected dose per gram tissue (% ID/g).

FIG. 12 also presents Table 5 which shows the biodistribution of 34a in balb/c mice (20–25 g), expressed as % injected dose per gram tissue (% ID/g).

FIG. 13 also presents Table 6 which shows the biodistributions of 46a in balb/c mice (20–25 g), expressed as % injected dose per gram tissue (% ID/g).

FIG. 14 also presents Table 7 which shows the biodistributions of 67a and 72a in balb/c mice (20–25 g), expressed as % injected dose per gram tissue (% ID/g).

FIG. 15 also presents Table 8 which shows the biodistributions of HPLC-purified (HP) and nonpurified (NP) 46a in nude rats (60 g), expressed as % injected dose per gram tissue (% ID/g).

EXAMPLES (SECTION A)

m-Trimethylsilyltoluene

Figure 1:
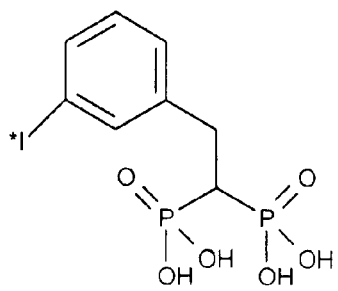
FIG. 1 shows the structure of bisphosphonate compounds 2h, 3h, 4d and 5x.
Figure 1:
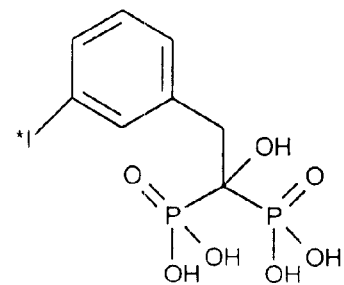
Figure 1:
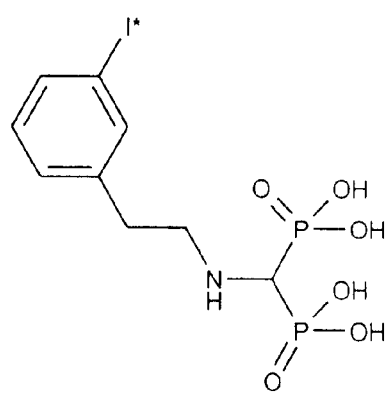
Figure 1:
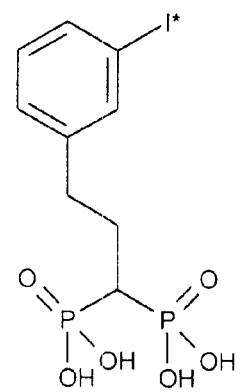
Figure 2:
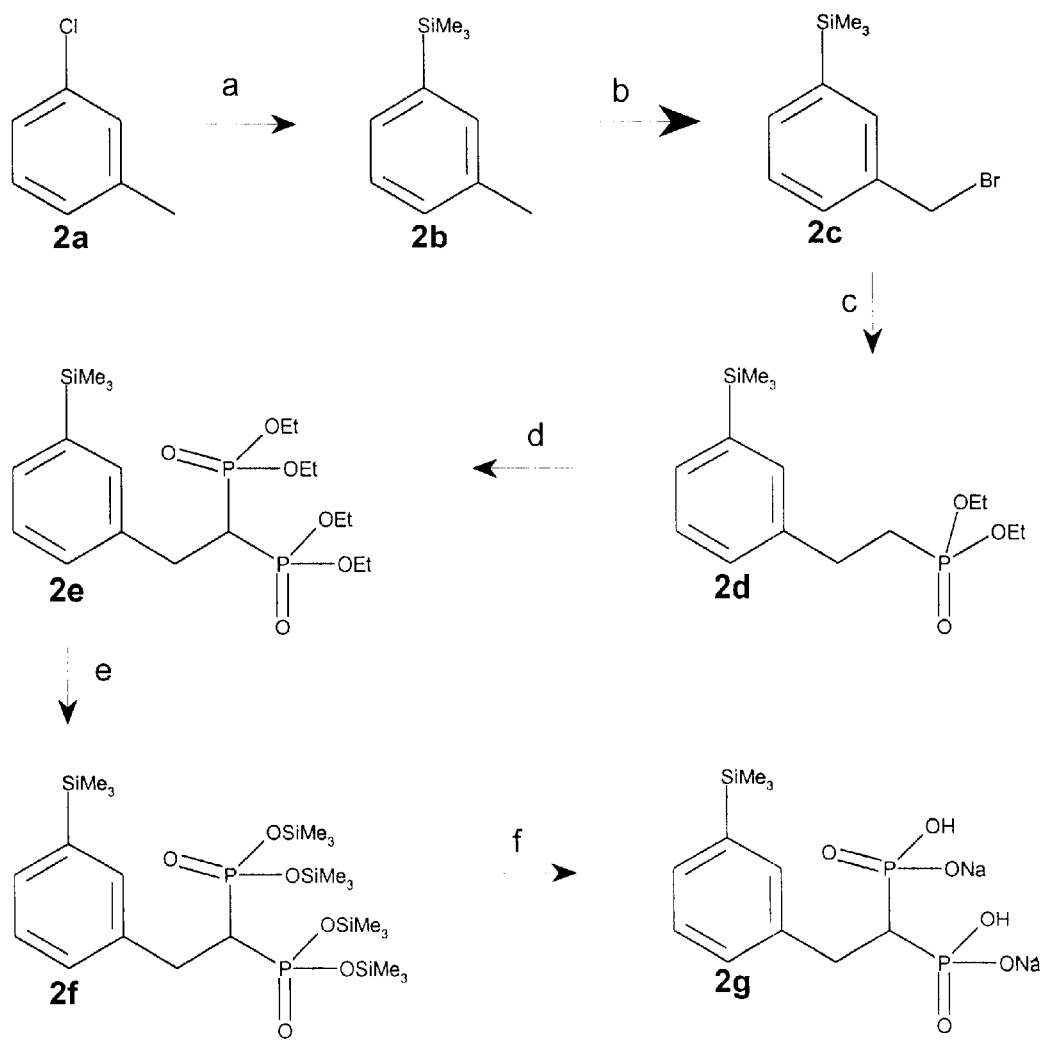
FIG. 2 shows the reaction scheme for the preparation of compound 2g.
Figure 3:
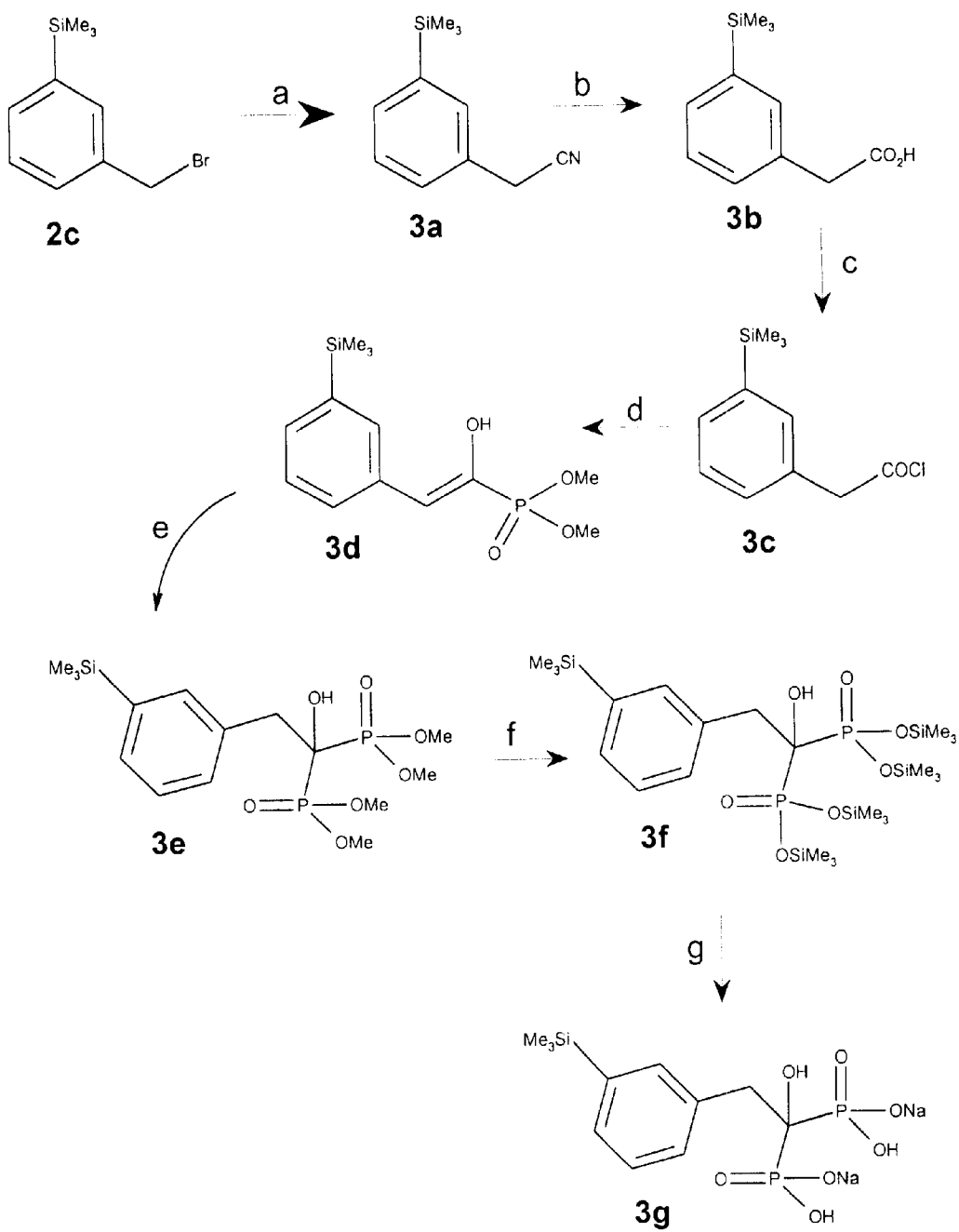
FIG. 3 shows the reaction scheme for the preparation of compound 3g.
Figure 4:
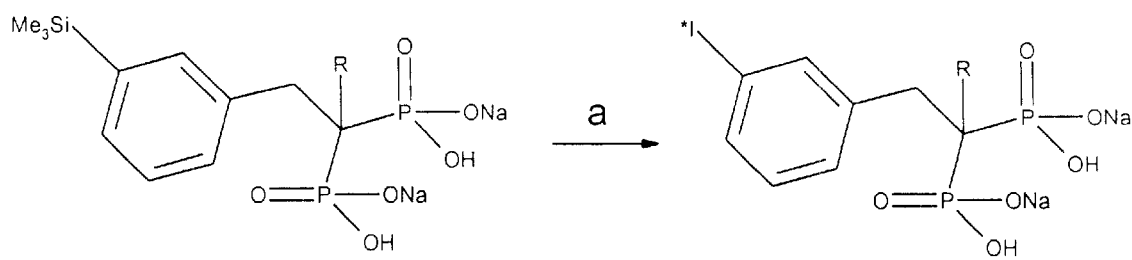
FIG. 4 shows the reaction scheme for radiolabelling compounds 2g and 3g.
Figure 5:
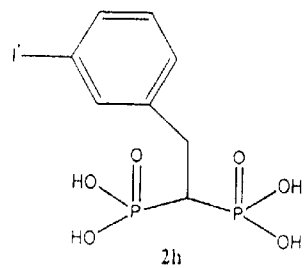
FIG. 5 shows the biodistribution of intravenously administered compound 2h in balb/c mice (20–25 g) after 30 mm (FIG. 5A), 2 hours (FIG. 5B), 5 hours (FIG. 5C), and 24 hours (FIG. 5D).
Figure 5:
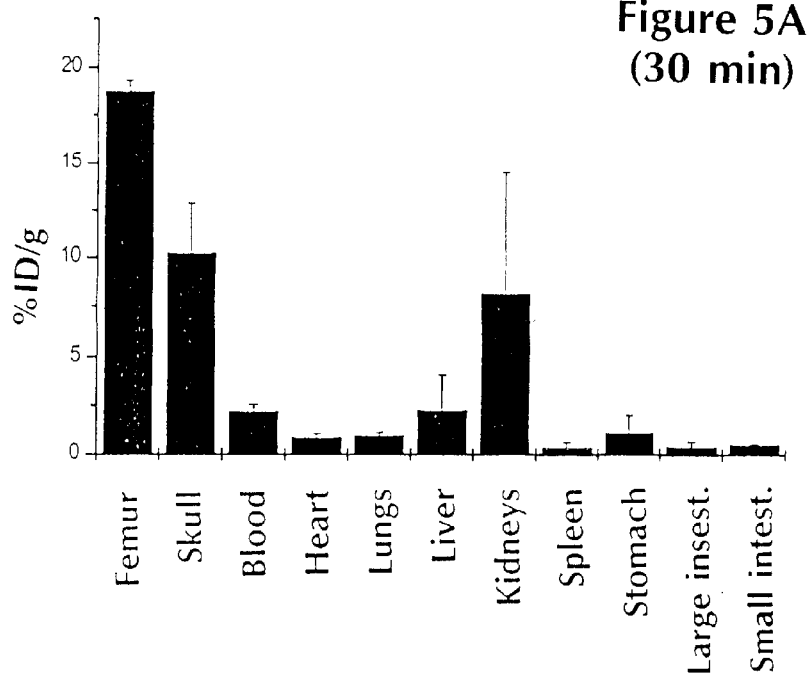
Figure 5:
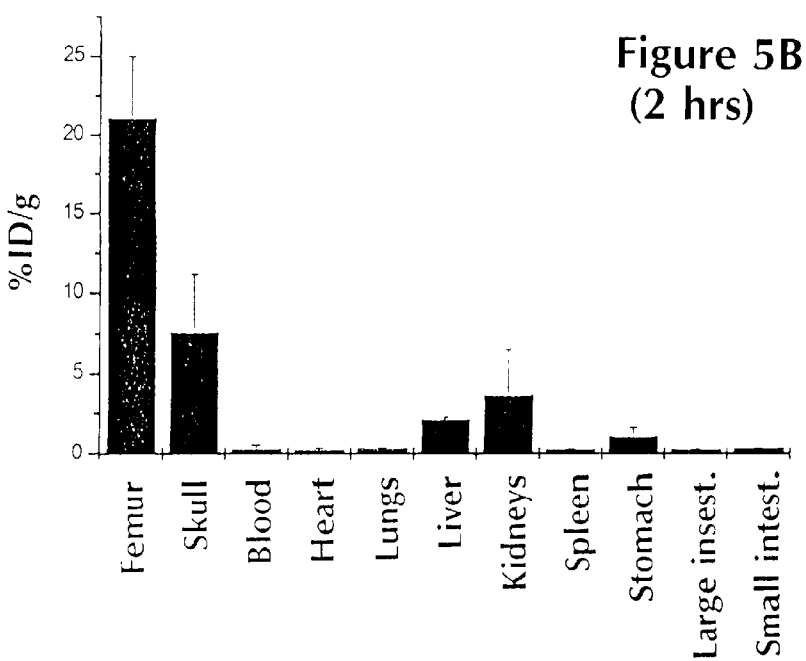
Figure 5C:
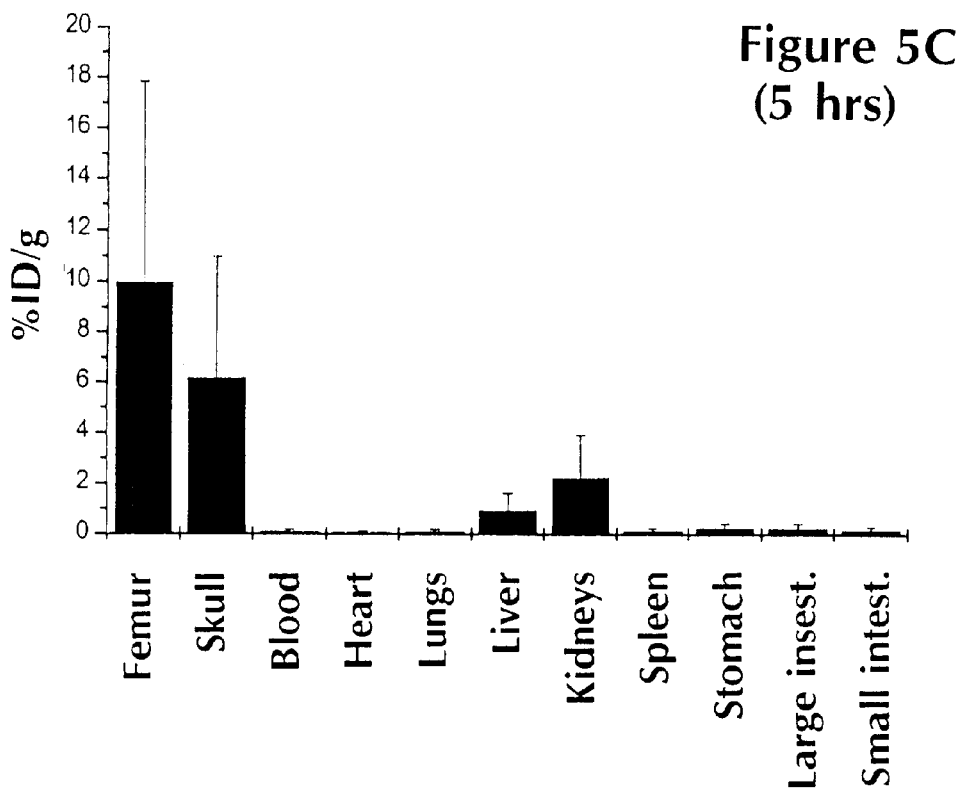
Figure 5D:
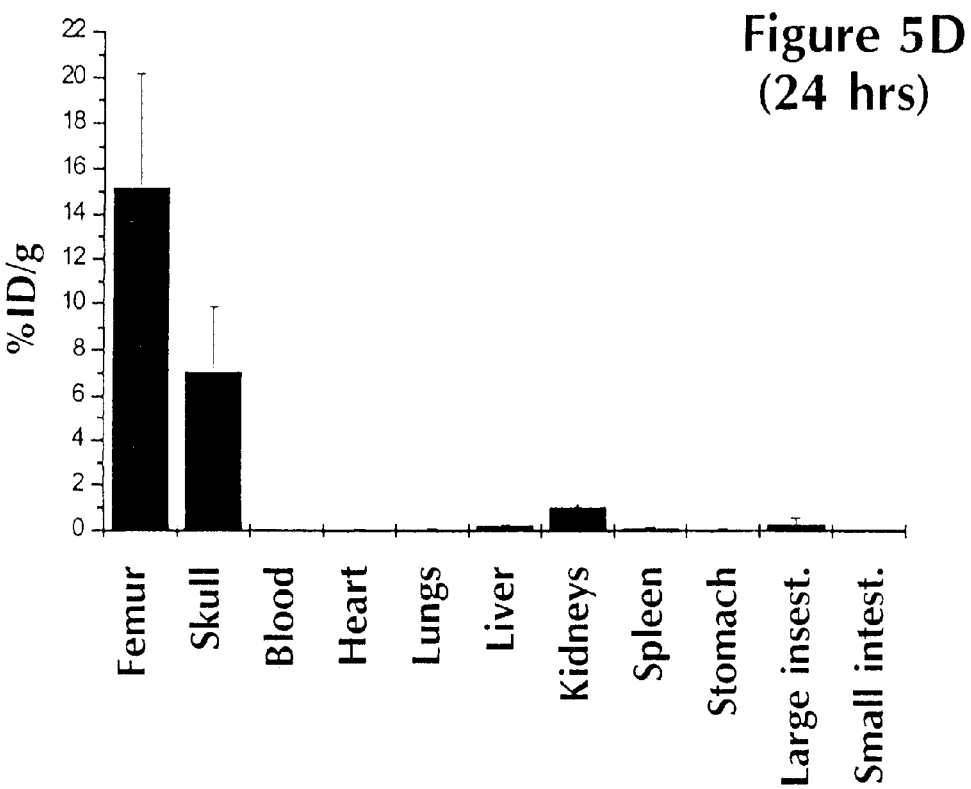
Figure 6:
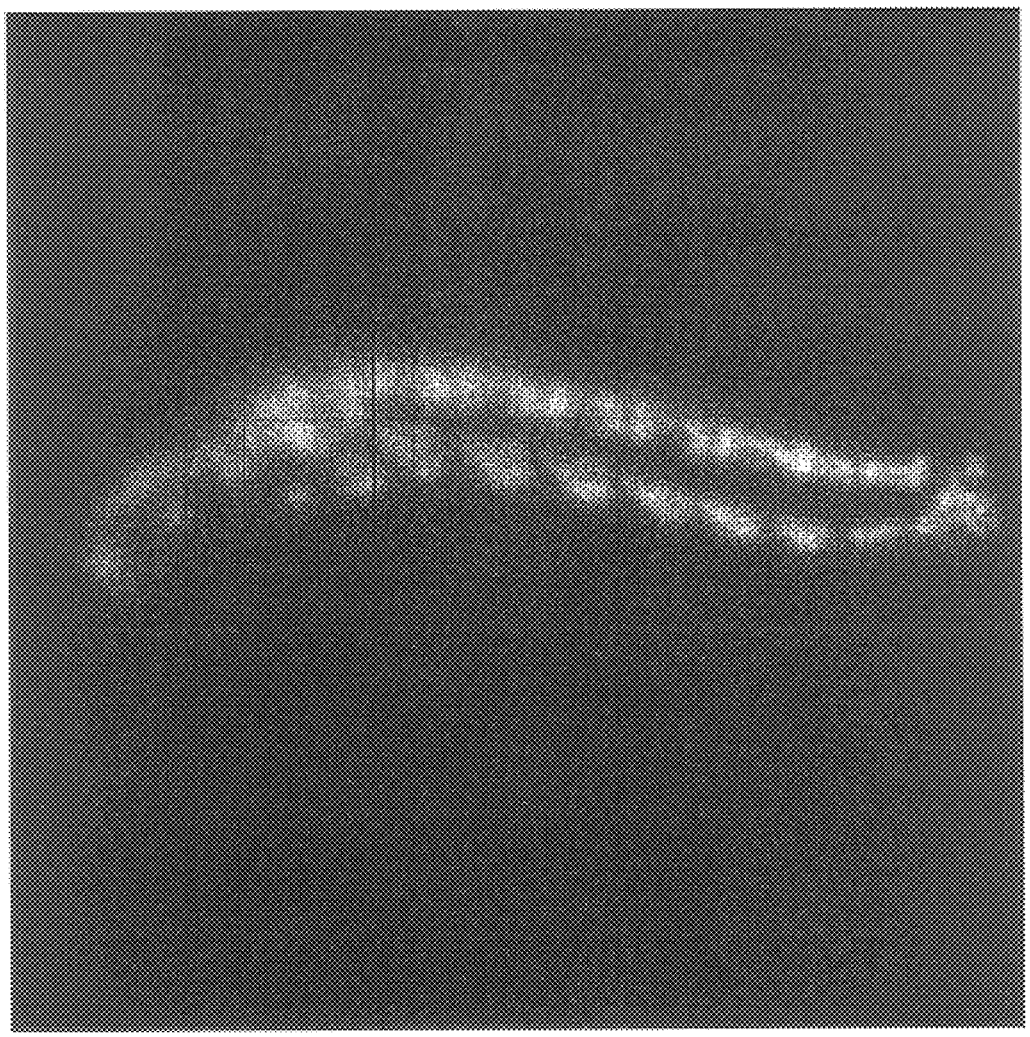
FIG. 6 shows a bioscope picture of the spinal cord (balb/c mice) employing compound 2h.

A solution of m-chlorotoluene (25.3 g, 0.20 mol), 1,2-dibromoethane (2.18 g, 11.6 mmol) and THF (40 cm$^3$) was added to magnesium turnings (5.35 g, 0.22 mol). The mixture was heated under reflux in an atmosphere of argon for 4 h, after which the heating bath was removed and trimethylchlorosilane (23.9 g, 0.22 mol) was added so that gently reflux was maintained. The mixture was stirred for another 30 min and then separated between 5% NaHCO$_3$ (100 cm$^3$) and dichloromethane (3×100 cm$^3$). The organic extract was washed with brine and dried (MgSO$_4$). The solvent was removed under reduced pressure affording the title compound (29.4 g, 89%) as a pale yellow liquid, which was used without purification in the next reaction. All spectroscopic data were identical to those reported in the literature (Eisenhut et al., ibid).

m-Trimethylsilylbenzylbromide

The reaction was carried out as described in the literature (Bijvoet, O. L. M. et al., Bisphosphonates on Bones, Elsevier Sciences B.V., Amsterdam, 1995, pp. 131 and pp. 142) with the following modifications. The reaction mixture was partitioned between water and dichloromethane, the organic extract was washed with brine, dried (MgSO$_4$) and the solvent evaporated. The residue was chromatographed on silica gel using hexane as an eluent to give the title compound (96%) as an orange liquid. The product was used without further purification in the next reaction.

m-Trimethylsilylbenzylcyanide

A mixture of KCN (5.5 g, 84 mmol), m-trimethylsilylbenzylbromide (5.31 g, 21.8 mmol), tributylamine (0.11 g, 0.59 mmol) and water (12.5 cm$^3$) was stirred overnight. The product was extracted with dichloromethane (3×30 cm$^3$), the extract was filtered through a silica plug (5g) and the solvent was removed under reduced pressure. The residue was distilled to give the product (2.27 g, 55%) as a colorless liquid.

Bp. 134–136° C. (2 mm); $V_{max}$(film)/cm$^{-1}$ 2956, 2255, 1412, 1249, 885 and 867; $\delta_H$ (200 MHz; CDCl$_3$; Me$_4$Si) 0.31 (9H, s, CH$_3$), 3.76 (2H, s, CH$_2$) and 7.27-7.56(4H, m, Ar); $\delta_C$ (50 MHz; CDCl$_3$; Me$_4$Si) 0.3, 24.3, 117.5, 127.7, 127.9, 128.6, 132.0, 132.3 and 141.2; m/z (EI) 189.0972 (M$^+$-C$_{11}$H$_{15}$NSi requires 189.0974).

m-Trimethylsilylphenylacetic Acid

To a solution of NaOH (4.0 g, 0.1 mol) in MeOH (20 cm$^3$) m-trimethyl-silylbenzylcyanide (2.84 g, 15.0 mmol) was added and the mixture was heated under reflux for 4 h. The solvent was evaporated and the residue was dissolved in water (50 cm$^3$). The resulting solution was washed with dichloromethane (2×20 cm$^3$), the aqueous phase was acidified with phosphoric acid to pH 2 and extracted with dichloromethane (3×30 cm$^3$). The extract washed with brine, dried (MgSO$_4$) and the solvent evaporated to give the title compound (2.93 g, 94%) as a yellow liquid.

$V_{max}$(film)/cm$^{-1}$ 3600–2600, 1717, 1418, 1254 and 847; $\delta_H$ (200 MHz; CDCl$_3$; Me$_4$Si) 0.32 (9H, s, CH$_3$), 3.70 (2H, s, CH$_2$) and 7.30–7.53 (4H, m, Ar); $\delta_c$ CDCl$_3$; Me$_4$Si) 0.53, 41.6, 127.8, 129.6, 132.1, 132.3, 134.1, 140.8 and 177.7; m/z (EI) 208.0918 (M$^+$-C$_{11}$H$_{16}$O$_2$Si requires 208.0920).

Dimethyl m-trimethylsilylphenylacetylphosphonate

To m-trimethylsilylphenylacetic acid (1.04 g, 5.0 mmol) was added SOCl$_2$ (0.82 g, 6.9 mmol) and the mixture was stirred overnight. Excess SOCl$_2$ was removed by adding toluene (2 cm$^3$) and then evaporating the solvent under reduced pressure. The residue was dissolved in THF (5 cm$^3$) and trimethylphosphite (0.69 g, 5.5 mmol) was added at −20° C., The resulting solution was kept in an ultrasound bath at 0° C. for 30 min, after which the solvent was evaporated to leave the phosphonate as a cream colored semisolid (1.63 g, 5.0 mmol). The product decomposed upon exposure to the atmosphere. An analytical sample was prepared by washing the crude product with hexane and was shown to consist of a mixture of two stereoisomeric enols. The spectral data represents the major component.

$V_{max}$(film)/cm$^{-1}$ 3600–2600, 1698, 1249 and 1036; $\delta_H$ (200 MHz; CDCl$_3$; Me$_4$Si) 0.19 (9H, s, CH$_3$), 3.86 (6H, d, J 14), 6.11 (1H, d, J 13), 7.20–7.78 (4H, m, Ar) and 7.92 (1H, d, J 7); $\delta_C$(50 MHz; CDCl$_3$; Me$_4$Si) 0.68, 54.6, 117.5, 118.1, 128.1, 130.4, 132.9, 133.6, 134.0, 134.9, 138.3, 140.6 and 142.3; $\delta_P$(500 MHz; CDCl$_3$; H$_3$PO$_4$) 16.3;; m/z (EI) 300.0929 (M$^+$-C$_{13}$H$_{21}$O$_4$PSi requires 300.0947).

Tetramethyl m-trimethylsilylphenyl-1-hydroxy-ethylidenebis(phosphonate)

To a solution of dimethyl m-trimethylsilylphenylacetylphosphonate (1.63 g, 5.0 mmol) in Et$_2$O (10 cm$^3$) was added a solution of dimethylphosphite (0.83 g, 7.5 mmol), dibutylamine (0.32 g, 2.5 mmol) and hexane (10 cm$^3$) at 0° C. A white solid began to form after a few minutes. After 20 min the mixture was filtrated to give the title compound (1.34 g, 65%) as a white solid. Recrystallization was achieved by adding water (9.5 cm$^3$) to a solution of the title compound (0.50 g) in acetic acid (0.5 cm$^3$) and then leaving the resulting mixture for several days in the refrigerator. Filtration afforded the bisphosphonate (0.33 g, 66%) as white crystals.

$V_{max}$(neat)/cm$^{-1}$ 3700–2815, 2958, 1645 and 1251; $\delta_H$ (200 MHz; CDCl$_3$; Me$_4$Si) 0.25 (9H, s, CH$_3$), 3.38 (2H, t, J 14), 3.71–382 (12H, m, OCH3) and 7.26–7.51 (4H, m, Ar); $\delta_c$ (50 MHz; CDCl$_3$; Me$_4$Si) 0.1, 40.1, 54.9, 73.3, 76.3, 79.3, 127.7, 132.1, 132.4, 133.8, 136.6 and 140.2; $\delta_P$(500 MHz; CDCl$_3$; H$_3$PO$_4$; M/Z (EI) 410.1080 (M$^+$-C$_{15}$H$_{28}$O$_7$P$_2$Si requires 410.1080).

Disodium m-trimethylsilylphenyl-1-hydroxy-ethylidenebis(Phosphonic Acid)

To tetramethyl m-trimethylsilylphenyl-1-hydroxy-ethylidenebis(phosphonate) (0.82 g, 2.0 mmol) was added trimethylbromosilane (2.45 g, 16 mmol) and the resulting solution was stirred for 1 h. Excess reagent was then removed under reduced pressure and the residue was dissolved in EtOH (75%, 8 cm$^3$) at 0° C. and stirred for 0.5 h. The resultant solution was neutralised to pH 8 with aqueous Na$_2$CO$_3$ (1.0 M, 3 cm$^3$) and filtrated to give the disodium bis(phosphonic acid) salt (0.75 g, 94%) as a white solid. The product was used without purification in the next reaction.

Tetramethyl m-iodophenyl-1-hydroxy-ethylidenebis (Phosphonate)

Tetramethyl m-trimethylsilylphenyl-1-hydroxy-ethylidenebis(phosphonate) (0.41 g, 1.0 mmol) was added to a solution of ICl (0.32 g, 2.0 mmol) in acetic acid (2 cm$^3$) and the mixture was stirred for 5 h. The solvent was then evaporated and the residue was extracted with 1:1 hexane:Et$_2$O (2×10 cm$^3$). Remaining solvents were removed from the residue under reduced pressure affording the title compound (0.38 g, 81%) as an orange liquid.

$\delta_H$ (200 MHz; CDCl$_3$; Me$_4$Si) 3.18 (2H, t, J 14) 3.68–3.79 (12H, m, OCH3) 6.95–7.69 (4H, m, Ar); $\delta_C$ (50 MHz; CDCl$_3$; Me$_4$Si) 39.7, 55.8, 56.3, 73.3, 76.3, 79.3, 94.2, 129.9, 130.8, 136.3, 136.8 and 140.2; $\delta_P$(500 MHz; CDCl$_3$; H$_3$PO$_4$) 19.6.

m-Iodophenyl-1-hydroxy-ethylidenebis(Phosphonic Acid)

A sample of tetramethyl m-iodophenyl-1-hydroxy-ethylidenebis(phosphonic acid) was prepared by refluxing the parent tetraester in concentrated hydrochloric acid for 3 h. Evaporation to dryness gave the title compound as an orange powder.

m-[$^{131}$I]-Iodophenyl-1-hydroxy-ethylidenebis (Phosphonic Acid)

To a solution of Na$^{131}$I in water (1–2 $\mu$l) was added a solution of N-chlorosuccinimide (0.4 mg, 3 mol) in 9:1 TFA:AcOH (10 $\mu$l) followed by the addition of disodium m-trimethylsilylphenyl-1-hydroxy-ethylidenebis (phosphonic acid) (0.1 mg, 0.25 $\mu$mol) in TFA (2 $\mu$l). The mixture was vortexed and left for 5 mm.

Biological Testing

In order to assess the targeting ability of the radioiodinated bisphosphonic acids described, tissue distributions were carried out in healthy mice.

24 h after injection, the bone uptake of phenylethylidenebisphosphonic acid (2h) was averaging 15±5% ID/g (injected dose per gram bone tissue) in femur, with a peak value of 21±4% ID/g after 2 h, indicating that the entire molecule is involved in the bone affinity.

Figure 7C:
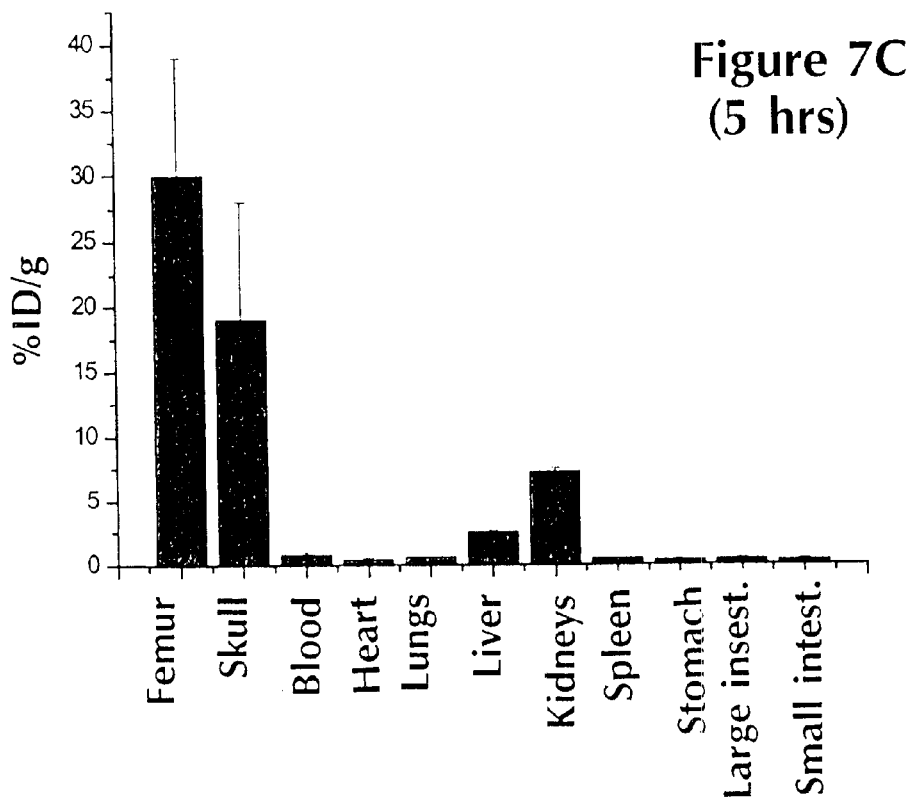
FIG. 7 shows the biodistribution of intravenously administered compound 3b in balb/c mice (20–25 g) after 30 mm (FIG. 7A), 2 hours (FIG. 7B), 5 hours (FIG. 7C) and 24 hours (FIG. 7D).
Figure 7D:
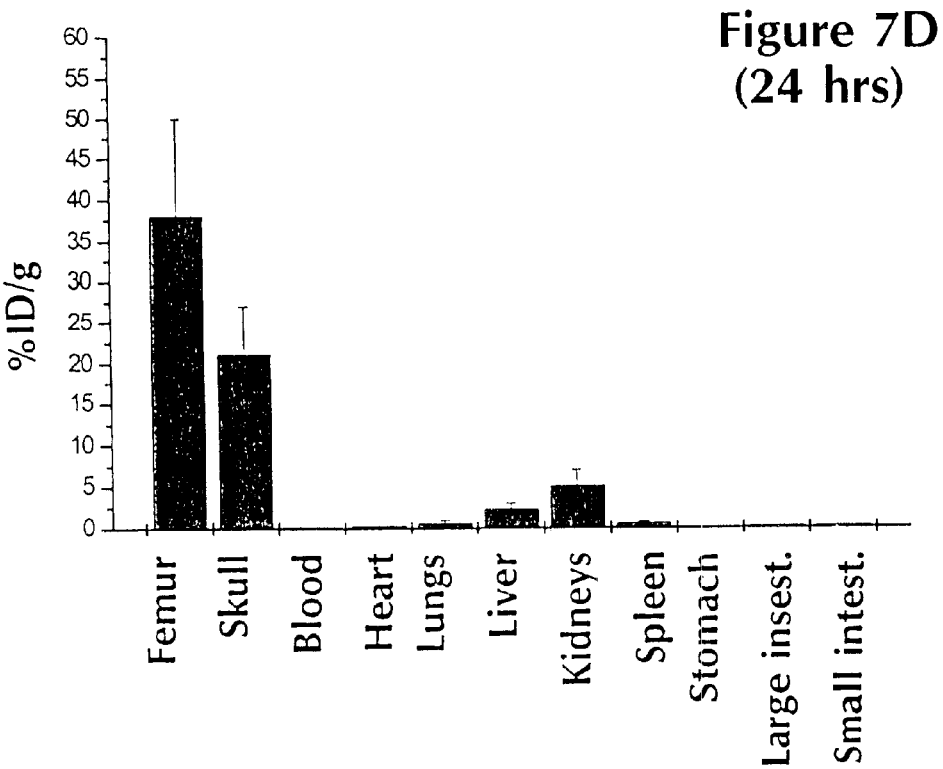

Compound 2h contains a hydrogen atom alpha to the bisphosphonate moiety and it is known in the art that hydroxybisphosphonic acids possess a superior bone affinity in general (Bijvoet, O. L. M. et al., ibid). Consequently, the alpha hydrogen in the phenylethylidenebisphosphonic acid was substituted with a hydroxy group. The resulting hydroxybisphosphonic acid 3h showed a two-fold increase in bone affinity compared to the unsubstituted derivative 2h (FIG. 7). 30 min after injection as much as 45±7% ID/g was observed in femur. The bone uptake remained high 24 h after injection (38±12% ID/g), with a peak value of 46±4% ID/g femur after 2 h. The compound cleared rapidly from all other organs, except the kidneys (5±2% ID/g 24 h) and liver (2±0.7% ID/g 24 h).

A fair resemblance has been found regarding uptake of bone seeking agents in various specimens (Murud, K. et al., Evaluation of blood clearance, tissue distribution, and bone microdistribution of $^{211}$At and $^{125}$I labeled bisphosphonates in dogs. Eur. J. Nucl. Med., 1999, submitted). However, care must be exercised when comparing different studies, since the age of the animals used is known to greatly affect bone uptake as well as kidney clearance (Hassfjell, S. P. et al., An alpha particle emitting bone seeking agent for targeted radiotherapy, Nucl. Med. Biol., 1997, in press). To overcome some of these problems an alternative parameter for the targeting ability of each compound was measured, namely % injected dose per gram tissue×animal body weight.

In this respect, the above-described compounds possess a bone uptake in the range 900 to 1100 (% injected dose per gram tissue×animal body weight). In contrast, the most promising radioiodinated compound reported in the literature to date possesses a bone uptake of only slightly greater than 400 (Larsen, R. H. et al., $^{211}$At- and $^{131}$I-labeled bisphosphonates with high in vivo stability and bone accumulation. J. Nucl. Med., 1999, in press). Since radioiodine is known to accumulate to a high degree in the thyroid gland (McNabb, F. M. Anne, Thyroid hormones, Englewood Cliffs, N.J.: Prentice Hall, 1992, pp. 23–25), uptake in the neck area is a good measurement for the stability of radioiodinated compounds. Indeed, about 0.05% of injected dose remained in the neck 24 h after injection, while values reported previously in the literature for this class of compounds have been in the range of 0.5% and above.

Biodistribution of Compound 3h in Nude/Nude Rats

Nude/nude rats with a body weight averaging 60 g were used in the biodistribution experiments. The aim of the study was to compare crude 3h with HPLC-purified 3h. The term "crude compound" refers to the diluted and neutralised labelling reaction mixture described hereinbefore. The compounds were administrated by tail vein injections of 200 μl for each animal, using three animals for each sample. 24 h after injection the animals were killed by a lethal injection and the tissue distribution determined.

Figure 8A:
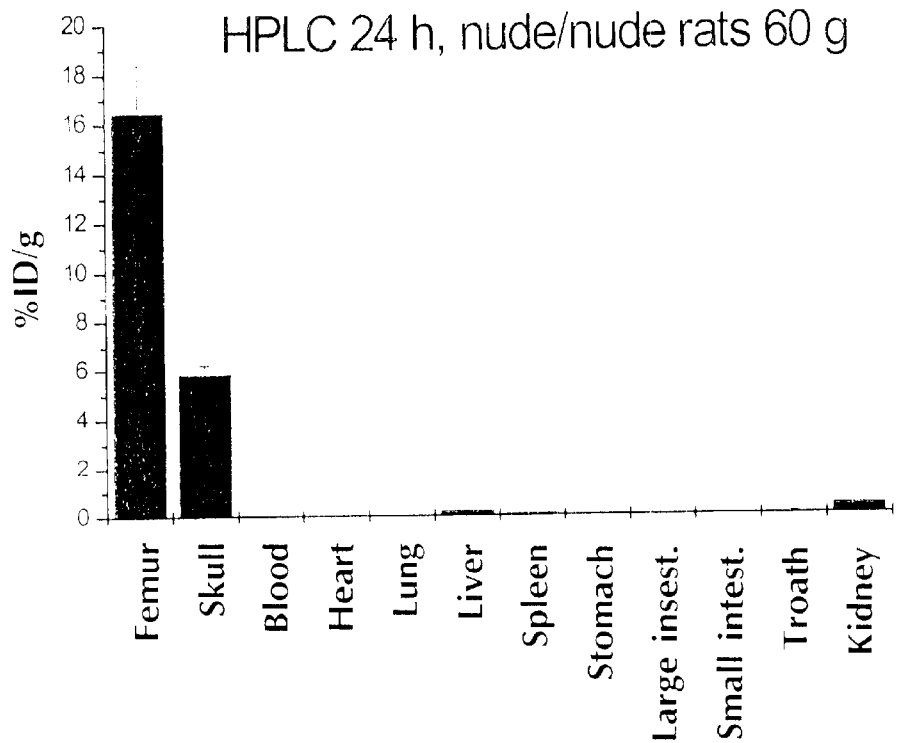
FIGS. 8A and 8B show the biodistribution of intravenously administered compound 3h in nude/nude rats (60g) for HPLC purified 3h and crude 3h.
Figure 8B:
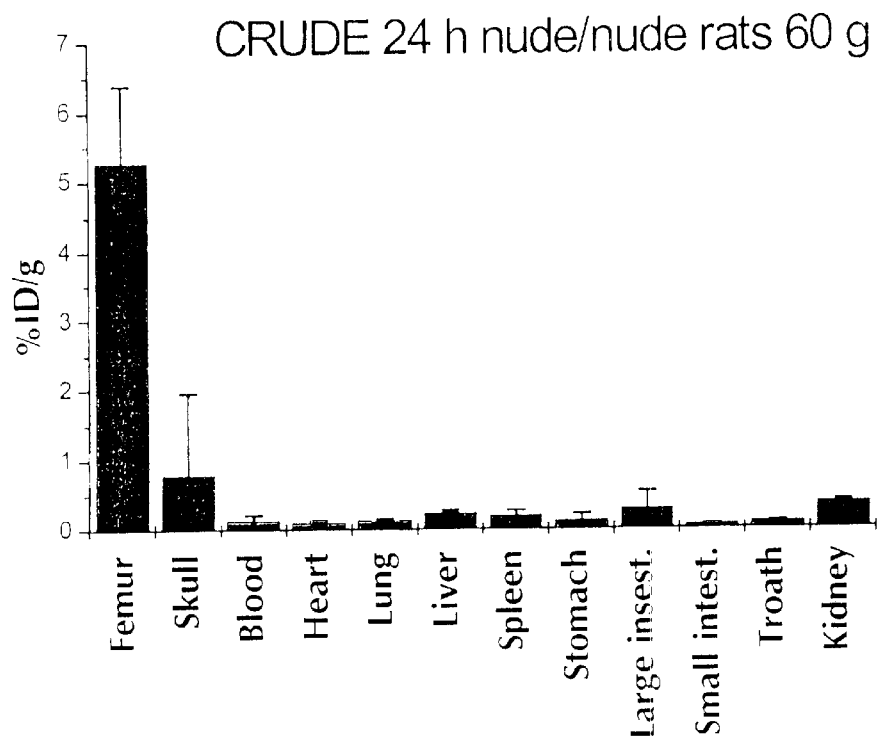

A significant difference was observed between crude 3h and HPLC purified 3h (FIG. 8). The purified compound possessed a 3-fold higher bone affinity than the crude product. Both samples showed high stability and selectivity although the purified sample was again superior. The bone affinity found for HPLC purified 3h was consistent with the results obtained with balb/C mice. Femur uptake was found to be 1020% g dose/g. In contrast, the most promising radioiodinated compound reported in the literature to date possesses a bone uptake of only slightly above 400% g dose/g.

Figure 9:
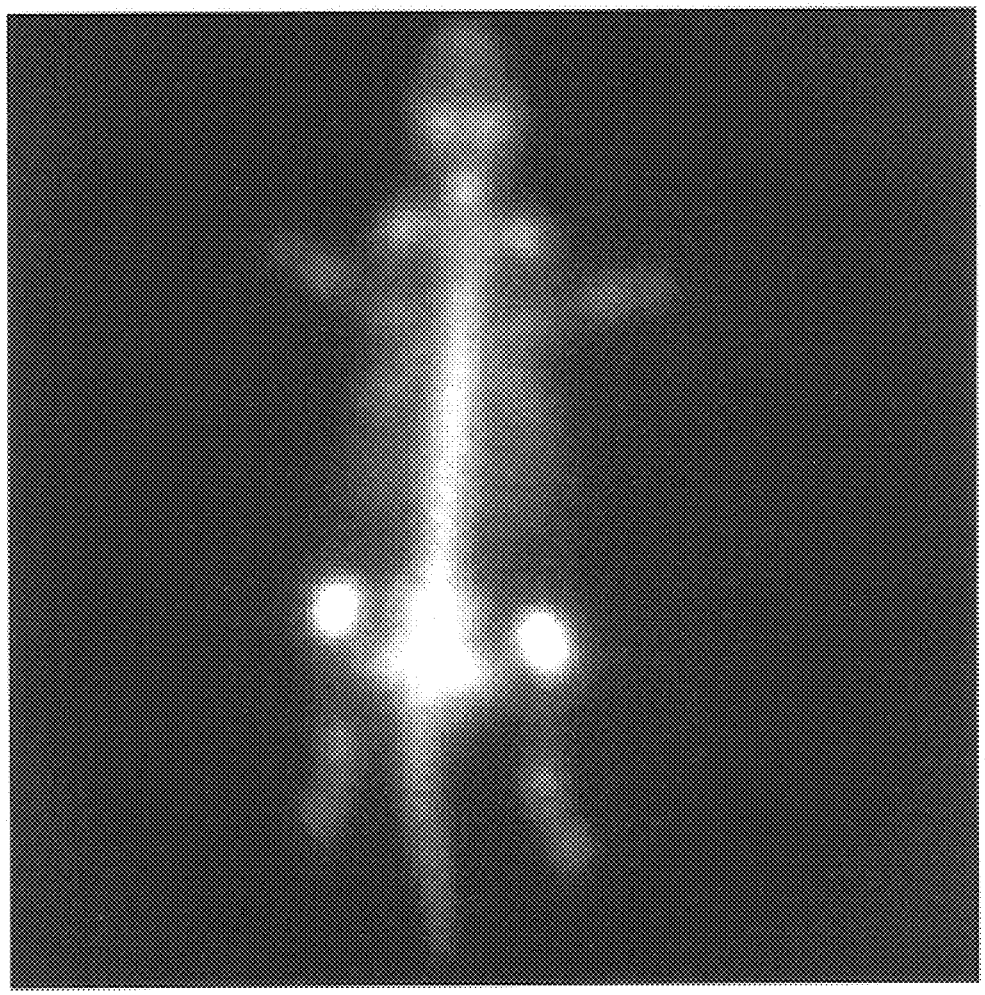
FIG. 9 shows a scintillation picture of intravenously administered compound 3h in nude/nude rat (60g) for HPLC purified compound.

It is interesting to compare the selectivity found in this experiment with the results obtained with balb/c mice. In mice, the highest uptake in non target tissues was found in kidneys. After 24 h the ratio between femur and kidney was found to be 7. In rats the ratio between femur and kidney was found to be above 45, indicating a remarkable selectivity. A scintillation picture of the HPLC purified compound in nude/nude rat further demonstrated the high selectivity of this compound (FIG. 9). To date, the most promising radioiodinated compound reported in the literature possesses ratios between femur uptake and uptake in non target tissues of 3/2 (femur:spleen), 7/3 (femur/liver) and 20 (femur/kidneys) after 24 h.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in chemistry or related fields are intended to be within the scope of the following claims.

EXAMPLES (SECTION B)

Evidence demonstrating the striking improvements in bone affinity, selectivity for bone, in vivo stability and anti tumour efficacy of the compounds of the present invention relative to the compounds disclosed in the closest prior art.

U.S. Pat. No 4,515,766 discloses compounds structurally related to those described in the present invention. Both include radiohalogenated bisphosphonates designed for clinical use. Eisenhut et al (*Appl. Radiat. Isot.,* 38 (1987) 535) and Larsen et al (*J. Nucl. Med.,* 40 (1999) 1197) have also described such compounds. The different workers have outlined different applications for these compounds; however, their potential use is very much determined by the radionuclide employed. This is because the biological properties required of the carrier molecule for applications such as palliative and curative treatment of bone-related cancer and imaging, are similar. The following data demonstrate the improved biological properties as compared to the compounds defining prior art.

We define the required biological properties for clinical applications of radiohalogenated bisphosphonates as affinity and selectivity for bone and in vivo stability. For the purpose of comparison, uptake in femur is regarded representative for bone affinity. Since the results available were obtained in different species, uptake is given as % gram dose per gram tissue. In this way the uptake is adjusted for the difference in weight in the animals used. The results are given in Table 1 and refer to the maximum uptake observed for each compound.

TABLE 1

Figure 10:
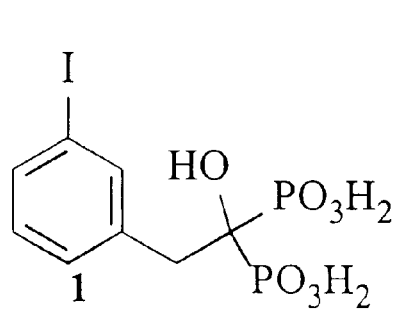
FIG. 10 shows (compound 1 as shown in FIG. 10 (also referred to as compound 3h in Examples, Section A and compound 46a in Examples, Section C), compound 2 which is disclosed in U.S. Pat. No 4,515,766, compound 3 which is disclosed in Eisenhut et al (*Appl. Radiat. Isot.,* 38 (1987) 535) and compound 4 which is disclosed in Larsen et al (*J. Nucl. Med.,* 40 (1999)
Figure 10:
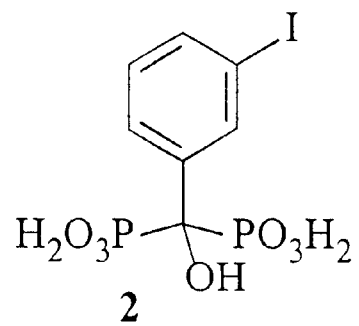
Figure 10:
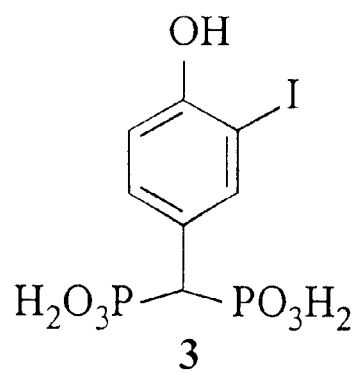
Figure 10:
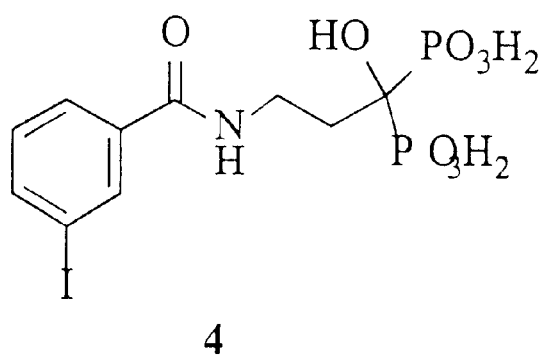
Figure 11:
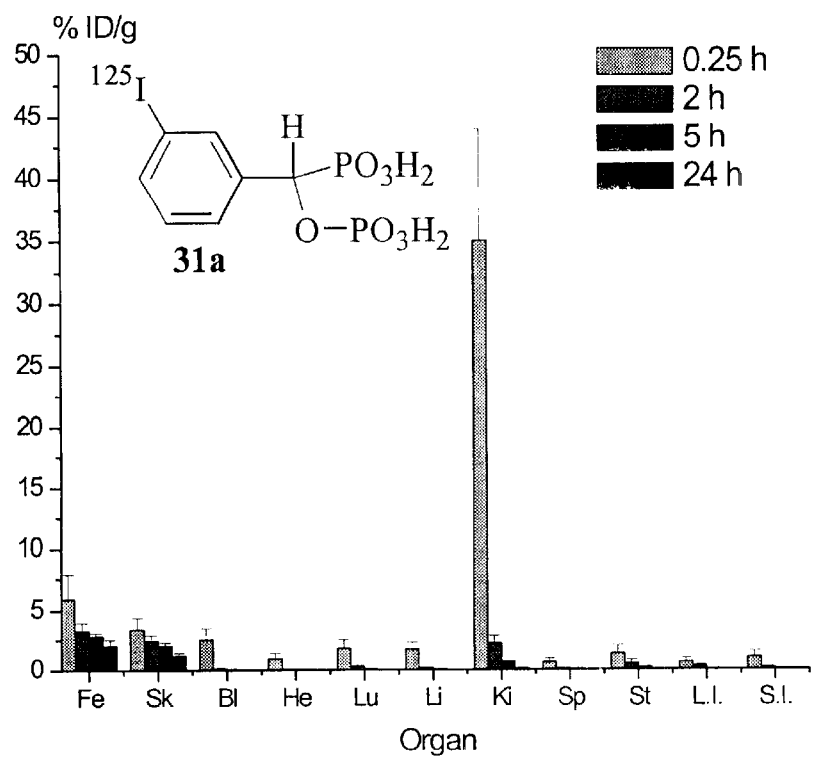
FIG. 11 shows the biodistribution of i.v. administered 31a in balb/c mice (16–18 g). The % of injected dose per gram of organ (% ID/g) is plotted for 0.25 h, 2 h, 5 h and 24 h time points. The values are the means of three mice with error bars representing the standard deviation. Abbreviations: Fe; femur, Sk; skull, Bl; blood, He; heart, Lu; lung, Li; liver, Ki; kidney, Sp; spleen, St; stomach, L.I.; large intestine, S.I.; small intestine.
Figure 12:
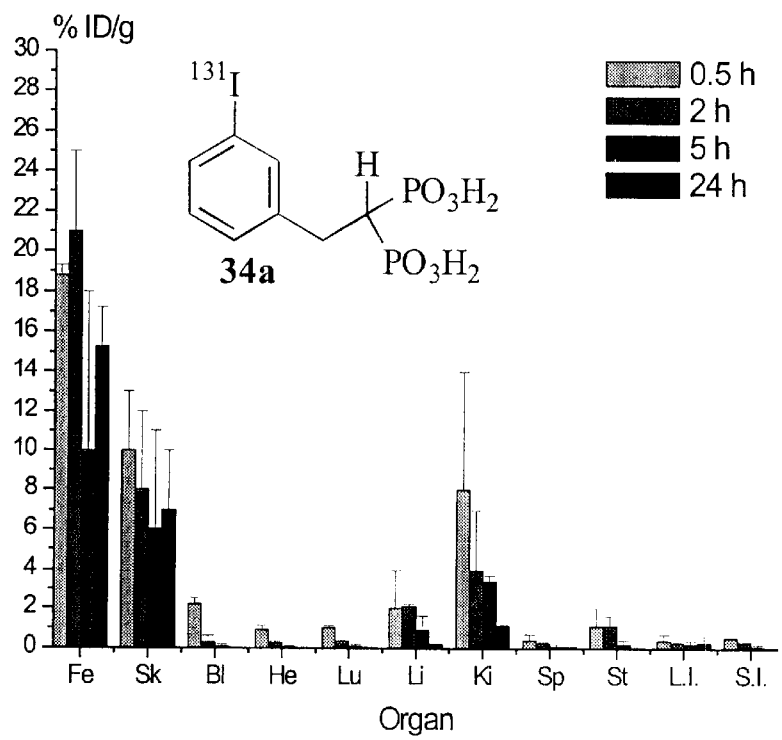
FIG. 12 shows the biodistribution of i.v. administered 34a in balb/c mice (20–25 g). The % of injected dose per gram of organ is plotted for 0.5 h, 2 h, 5 h and 24 h time points. The values are the means of three mice with error bars representing the standard deviation. Abbreviations: Fe; femur, Sk; skull, Bl; blood, He; heart, Lu; lung, Li; liver, Ki; kidney, Sp; spleen, St; stomach, L.I.; large intestine, S.I.; small intestine.
Figure 13:
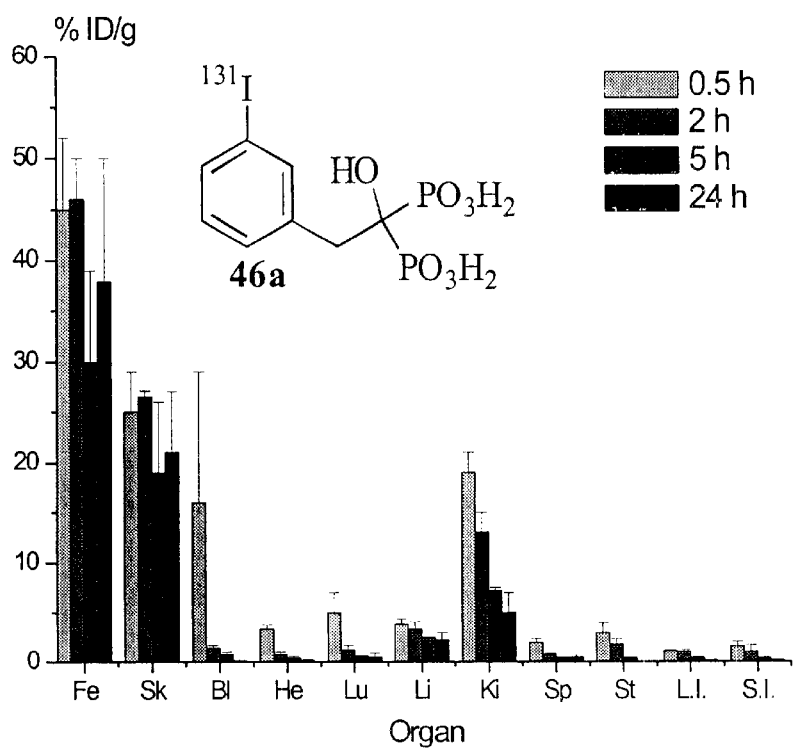
FIG. 13 shows the biodistribution of i.v. administered 46a in balb/c mice (20–25 g). The % of injected dose per gram of organ is plotted for 0.5 h, 2 h, 5 h and 24 h time points. The values are the means of three mice with error bars representing the standard deviation. Abbreviations: Fe; femur, Sk; skull, Bl; blood, He; heart, Lu; lung, Li; liver, Ki; kidney, Sp; spleen, St; stomach, L.I.; large intestine, S.I.; small intestine.
Figure 14:
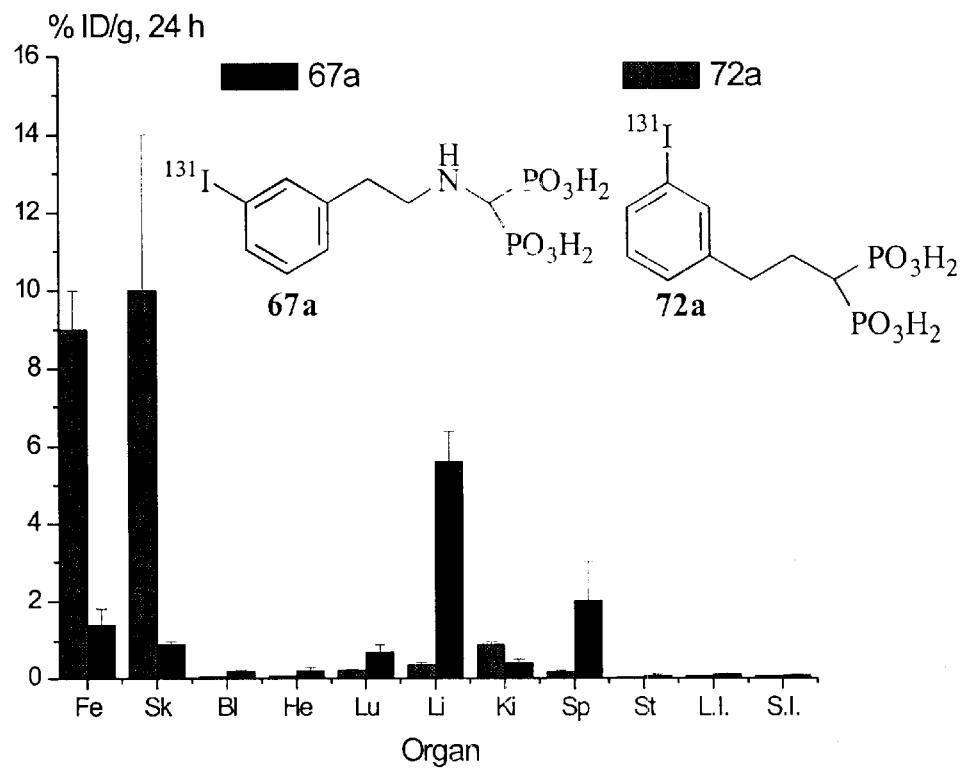
FIG. 14 shows the biodistribution of i.v. administered 67a and 72a in balb/c mice (20–25 g). The % of injected dose per gram of organ at the 24 h time point is plotted for both compounds. The values are the means of three mice with error bars presented as standard deviation. Abbreviations: Fe; femur, Sk; skull, Bl; blood, He; heart, Lu; lung, Li; liver, Ki; kidney, Sp; spleen, St; stomach, L.I.; large intestine, S.I.; small intestine.

| COMPOUND | Uptake in femur expressed as % gram dose per gram tissue |
|---|---|
| (compound 1, FIG. 10 and compound 3h FIG. 1) | 1025 (balb/c mice, 20–25 g, 2 h), 986 (Rowett rats, 60 g, 24 h) |
| U.S. Pat. No. 4,515,766 (compound 2, FIG. 1) | 299 (Swiss Webster mice, 20–25 g, 47 h) |
| Eisenhut et al. (compound 3, FIG. 1) | 438 (Sprague-Dawley rats, 220 g, 24 h) |
| Larsen et al. (compound 4, FIG. 1) | 702 (balb/c mice, 19–22 g, 2 h) |

As can be seen from Table 1, minor changes in the molecular structure of the carrier molecule may result in drastically changes in bone affinity. The most striking difference is observed when a methylene linker is introduced between the bisphosphonate part and the aromatic moiety in compound 2, resulting in compound 1 (see FIG. 10. Please note that compound 1 is the same as compound 3h presented in FIG. 1. The compound is hereinafter referred to as compound 1) This improves bone affinity from 299 to 1025% dose gram per gram tissue. Actually, the introduction of this linker resulted in a compound with a superior bone affinity as compared to all reported radiohalogenated bisphosphonates.

Selectivity for bone is usually given as the ratio between uptake in femur and that of the soft tissue with the highest uptake. In Table 2 ratios between femur and soft tissues are given for the actual compounds.

TABLE 2

| COMPOUND | Ratio between uptake in femur and soft tissues |
|---|---|
| (compound 1, FIG. 10 and compound 3h FIG. 1) | 7.3 (femur/kidney, balb/c mice, 20–25 g, 24 h) and 45.7 (femur/kidney, Rowett rats, 60 g, 24 h) |
| U.S. Pat. No. 4,515,766 (2) | 1.7 (femur/stomach, Swiss Webster mice, 20–25 g, 47 h) |
| Eisenhut et al. (3) | 1.5 (femur/kidney, Sprague-Dawley rats, 220 g, 24 h) |
| Larsen et al. (4) | 3.2 (femur/spleen, balb/c mice, 19–22 g, 24 h) |

As can be seen from Table 2, the bisphosphonate 1 has a very high selectivity for bone as compared with other radiohalogenated bisphosphonates.

It is well known that iodine accumulate in the thyroid, and to a lesser extent, in the stomach. Therefore, uptake in these tissues may be interpreted as enzymatic dehalogenation of the administered compounds. The uptake in the thyroid (expressed as % injected dose/organ) and that of the stomach (expressed as % ID/g) are given in Table 3.

TABLE 3

| COMPOUND | Thyroid | Stomach |
|---|---|---|
| (compound 1, FIG. 10 and compound 3h FIG. 1) | 0.06 ± 0.04 (balb/c mice, 20–25 g, 24 h) and 0.02 ± 0.01 (Rowett rats, 60 g, 24 h) | 0.13 ± 0.01 (balb/c mice, 20–25 g, 24 h) and 0.05 ± 0.01 (Rowett rats, 60 g, 24 h) |
| U.S. Pat. No. 4,515,766 (2) | 0.414 ± 0.147 (Swiss Webster mice, 20–25 g, 47 h) | 7.65 ± 0.02 (Swiss Webster mice, 20–25 g, 47 h) |
| Eisenhut et al. (3) | 3829 (% ID/g, Spargue-Dawley rats, 220 g, 24 h) | |
| Larsen et al. (4) | 0.45 ± 0.36 (balb/c mice, 19–22 g, 24 h) | 0.93 ± 0.95 (balb/c mice, 19–22 g, 24 h) |

The results indicate that the in vivo stability of the bisphosphonate 1 is about 7 times as high as that of compound 2 and 3, making the bisphosphonate 1 superior with respect to in vivo stability.

Furthermore, the bisphosphonate 1 has been evaluated in models of human breast cancer (MT-1) and osteoblastic osteosarcoma (OHS). The models were established in immuno-deficient rats. In the breast cancer model, treatment with the bisphosphonate resulted in increased lifetime. The response was statistically significant ($p<0.05$) at all dose levels investigated. In comparison, repeated treatments with the chemotherapeutic agents cisplatin and doxorubicin have not improved survival nor did they have any significant effect on the metastatic growth in this model. In the osteosarcoma model, treatment with the hydroxybisphosphonate 1 resulted in a dramatic increase in lifetime. Moreover, in the group receiving the highest dose, 3 of 5 animals were long-time survivors, while all the controls developed palpable tumours. At an administered dose level that resulted in similar survival of OHS-inoculated rats, the bone marrow dose of 1 was estimated to be less than half of that resulting from $^{153}$Sm-EDTMP. These results indicate that the antitumour efficacy of the hydroxybisphosphonate 1 is considerably higher than that of currently used drugs.

In conclusion, the bisphosphonate 1 has a considerably higher selectivity and affinity for bone than the bisphosphonates 2, 3 and 4. Additionally, compound 1 is far more stable in vivo. Finally, a high antitumour efficacy has been demonstrated for the bisphosphonate 1.

EXAMPLES (SECTION C (I))

General

Unless otherwise indicated analytical grade reagents were used without further purification. Other grades were purified according to standard procedures before use. All experiments involving organic solvents were run under an argon atmosphere. Glassware was dried over an open flame under low pressure or oven-dried at 120° C. over night. $^1$H, $^{13}$C and $^{31}$P NMR spectra were obtained with the following instruments: Varian Gemini 200, Bruker DPX 200 and Bruker DRX 500. Infrared spectra were obtained with a Perkin-Elmer 1310 infrared spectrophotometer or a Nicolet Magna-IR 550 spectrometer. Mass spectra were obtained on a Fision VG pro spectrometer; for GC-MS, a Fisons 8065 gas chromatograph with a CP SIL SCB-MS column was attached to the spectrometer. HPLC separations were performed with a systems consisting of a LC 10 AT pump and an SPD-M10A diode array UV detector, both from Shimadzu (Shimadzu Corporation, Kyoto, Japan). The column used was a PLRP-S (5 μm, 100 Å, 150×1,6 mm, Polymer Laboratories, UK). Unless otherwise indicated a mobile phase flow of 1 ml/min was used. Reaction mixtures were sonificated with a Transsonic 310 ultrasoundbath (Heigar). Melting points were measure on a Büchi apparatus and are uncorrected.

Abbreviations

AIBN: 2,2'-azobis(isobutyronitrile); TFA: trifluoroacetic acid; THF: tetrahydrofuran; LDA: lithium diisopropylamide; NCS: N-chlorosuccinimide; NBS: N-bromosuccinimide: TMSCl: trimethylchlorosilane; TMSBr: trimethylbromosilane; ICl: iodomonochloride; MsCl: methanesulphonyl chloride; TsCl: p-toluenesulphonyl chloride; TsOH: p-toluenesulphonic acid.

General Procedures

Preparation of LDA (xmmol): Diisopropylamine (xmmol) was dissolved in THF (xml) and the resultant solution was cooled to –78° C. by means of a dry ice-acetone bath. n-Butyllithium (0.625×ml of a 1.6 M solution in hexanes, xmmol) was added and the solution was allowed to reach 0° C. for 15 min.[56] Sodium diethylphosphite: To sodium (xmmol) was added THF (xml) and diethyl phosphite (1.1×mmol) and the mixture was stirred overnight.[30] Transesterification: To one equivalent of the parent tetra (alkyl) ester was added 10 equivalents of TMSBr and the mixture was stirred for 3 h at room temperature. The volatiles were then removed under reduced pressure to give the tetra(trimethylsilyl) ester.[35] Hydolysis: A sample of the tetra(alkyl) ester was dissolved in concentrated hydrochloric acid and the solution was refluxed for 3 h. The resultant mixture was then concentrated to dryness under reduced pressure to give the actual bisphosphonic acid.[49] Iodination: To the trimethylsilyl derivative (xmmol) was added a solution of ICl (2×mmol) in acetic acid (5×ml). The resulting mixture was stirred for 5 h at room temperature and concentrated to dryness under reduced pressure. The residue was dissolved in $Et_2O$ and the solution was washed with saturated $NaHCO_3$ (aq), followed by saturated $Na_2SO_3$ (aq), water and brine. The organic phase was dried ($MgSO_4$), filtered and the solvent was evaporated yielding the iodo derivative.

Diethyl hydroxy(m-nitrobenzyl)Phosphonate (17)

m-Nitrobenzaldehyde (4.53 g, 30 mmol) was dissolved in diethyl phosphite (4.14 g, 30 mmol) under gentle heating. The solution was brought to room temperature and KF (8.7 g, 0.15 mole) was added with rapid stirring. After 30 min the mixture was suspended in $CH_2Cl_2$ (150 ml). The resultant suspension was filtered and the filtrate was concentrated under reduced pressure furnishing 8.57 g (99%) of 17 as a yellow colored solid, mp 93–95° C., IR (neat): 3750–3040, 1540, 1355, 1205 and 1050; $^1H$ NMR (200 MHz, $CDCl_3$): δ1.23 (6H, m), 4.10 (4H, m), 5.14 (1H, d, J=12 Hz), 5.94 (1H, s, OH) and 7.93 (4H, m); 13C NMR (50 MHz, $CDCl_3$): δ17.6, 64.2, 64.9, 72.1, 122.4, 123.1, 129.3, 133.4, 139.8 and 148.3; HR-MS (EI): m/e 289.0715 ($M^+C_{11}H_{16}NO_6P$ requires 289.0714).

Diethyl mesyloxy(m-nitrobenzyl)phosphonate (18)[57]

To a solution of the phosphonate 17 (2.85 g, 9.8 mmol) in toluene (90 ml) was added MsCl (1.26 g, 11 mmol). A solution of $Et_3N$ (1.52 g, 15 mmol) in toluene (10 ml) was then added dropwice at −10° C. After 20 min the cooling bath was removed and water (25 ml) was added. The organic phase was washed with 10% HCl, saturated $NaHCO_3$ (aq), brine and dried ($MgSO_4$). Filtration through a silica plug and removal of solvent under reduced pressure gave 3.18 g (88%) of 18 as a white solid, mp 81–84° C., IR (neat): 2940, 1530, 1380, 1360, 1245 and 1025; $^1H$ NMR (200 MHz, $CDCl_3$): δ1.28 (6H, m), 3.08 (3H, s,), 4.17 (4H, m), 5.84 (1H, d, J=15 Hz) and 7.97 (4H, m); $^{13}C$ NMR (50 MHz, $CDCl_3$): δ16.4, 39.5, 64.4, 74.0, 77.4, 123.1, 124.7, 130.3, 134.1, 135.2 and 148.7; HR-MS (EI): m/e 367.0472 ($M^+C_{12}H_{18}NO_8PS$ requires 367.0491).

Tetraethyl 1-phosphonyl(m-nitrobenzyl)Phosphate (19)

From 17: To a solution of the phosphonate 17 (0.289 g, 1 mmol) in THF (10 ml) was added diethyl chlorophosphate (0.259 g, 1.5 mmol) and $Et_3N$ (0.30 g, 3.0 mmol) at 0° C., After 20 min the cooling bath was removed and the reaction mixture was stirred for 48 h. The mixture was extracted with $CH_2Cl_2$, the organic phase was washed with water, 10% $H_3PO_4$, then brine and dried ($MgSO_4$). Filtration and evaporation afforded 0.25 g (59%) of a pale yellow colored liquid. From 18: Sodium diethyl phosphite (18 mmol) was added to a solution of the phosphonate 18 (5.51 g, 15 mmol) in THF (60 ml) at 0° C., After 2 h the reaction was quenched by addition of saturated $NH_4Cl$ (aq) (1.5 ml) and the mixture was concentrated under reduced pressure. The residue was extracted with $CH_2Cl_2$, the organic phase was washed with water, then brine and dried ($MgSO_4$). Filtration and evaporation yielded the crude product (6.45 g), which was purified by flash chromatography (silica, AcOEt/MeOH gradient) to give 4.64 g (73%) of the phosphate phosphonate 19. From 22a: Sodium diethyl phosphite (3.5 mmol) was added to a solution of the phosphonate 22a (0.91 g, 2 mmol) in THF (10 ml) at 0° C., The resulting orange mixture was stirred for 2 h and quenched by addition of saturated $NH_4Cl$ (aq) (1 ml). The product mixture was extracted with $CH_2Cl_2$, the organic phase was washed with water, then brine and dried ($MgSO_4$). Filtration and evaporation gave 0.76 g (89%) of 19 as a yellow colored liquid. IR (film): 2910, 1535, 1350, 1290 and 1025; $^1H$ NMR (200 MHz, $CDCl_3$): δ1.23 (12H, m), 3.99 (8H, m), 5.64 (1H, dd, J=3, 11 Hz) and 7.87 (4H, m); $^{13}C$ NMR (50 MHz, $CDCl_3$): δ16.6 (m), 64.5 (m), 71.9 (d, J=7 Hz), 75.3 (d, J=7 Hz), 122.5, 123.8, 128.4, 129.5, 133.7 and 148.3; HR-MS (EI): m/e 425.1010 ($M^+C_{15}H_{25}NO_9P_2$ requires 425.1006).

Reaction of Tetraethyl 1-phosphonyl(m-nitrobenzyl) Phosphate (19) with Sodium Ethoxide Sodium ethoxide was prepared from Na (0.38 g, 16.5 mmol) and EtOH (10 ml). The phosphate phosphonate 19 (0.41 g, 1 mmol) was then added neat and the resulting solution was stirred overnight. The reaction was quenched by addition of saturated $NH_4Cl$ (aq) (2 ml) and the solvent was evaporated. The residue was extracted with $CH_2Cl_2$, the organic phase was washed with water, then brine and dried ($MgSO_4$). Filtration and evaporation afforded 0.44 g of a yellow colored liquid. $^1H$- and $^{13}C$ NMR of the product mixture confirmed the presence of triethylphosphate and m-nitrobenzylalcohol as the two major products by comparison with authentic samples.

Diethyl Tosyloxy(m-nitrobenzyl)Phosphonate (22a)

To the phosphonate 17 (2.89 g, 10 mmol) and TsCl (2.29 g, 12 mmol) was added pyridine (1.58 g, 20 mmol) and the mixture was stirred overnight. Ice-water (75 ml) was added and the resulting mixture was stirred for 20 min. The mixture was extracted with $CH_2Cl_2$, the organic phase was washed with 10% $H_3PO_4$, then brine and dried ($MgSO_4$). Filtration and evaporation afforded 4.00 g (90%) of 22a as a yellow colored solid, mp 90–92° C. $^1H$ NMR (200 MHz, $CDCl_3$): δ 1.25 (6H, m), 2.34 (3H, s), 4.13 (4H, m), 5.72 (1H, d, J=16 Hz) and 7.60 (8H, m); $^{13}C$ NMR (50 MHz, $CDCl_3$): δ16.3 (m), 21.4, 64.2 (m), 74.2, 77.5, 122.8, 123.7, 127.9, 129.5, 129.8, 133.2, 133.9, 134.4, 145.6 and 147.9; MS (EI): e/m 443.0 ($M^+1.95$), 2.88.0 (34.4) and 244.0 (100).

Diethyl Tosyloxybenzylphosphonate (22b)

Diethyl hydroxybenzylphosphonate was prepared as described in the literature.[28] The sulphonate 22b was then obtained in 98% yield from diethyl hydroxybenzylphosphonate by employing the method described for the preparation of the sulphonate 22a to give a white solid, mp 63–65° C. $^1H$ NMR (200 MHz, $CDCl_3$): δ1.21 (6H, m) 2.34 (3H, s), 4.03 (4H, m), 5.65 (1H, d, J=16 Hz) and 7.35 (9H, m); $^{13}C$ NMR (50 MHz, $CDCl_3$): δ16.4 (m), 21.6, 63.5 (m), 75.8, 79.2, 128.0, 128.2, 128.3, 128.4, 128.5, 129.0, 129.1, 129.5, 131.8, 133.8 and 144.8; MS (EI): e/m 398.7 ($M^+0.80$), 260.7 (45.7), 243.8 (32.9) and 154.8 (100).

Tetraethyl 1-phosphonylbenzylphosphate (23)

Sodium diethyl phosphite (3.5 mmol) was added to a solution of the phosphonate 22b (0.79 g, 2 mmol) in THF (10 ml) at 0° C. The resulting mixture was stirred overnight and quenched by addition of saturated NH$_4$Cl (aq) (1 ml). The mixture was extracted with CH$_2$Cl$_2$, the organic phase was washed with water, then brine and dried (MgSO$_4$). Filtration and evaporation followed by flash chromatography (silica, EtOAc/MeOH gradient) of the residue provided 0.47 g (62%) of 23 as a pale yellow colored liquid. IR (film): 2960, 2240, 1255 and 1032; $^1$H NMR (200 MHz, CDCl$_3$): δ1.21 (12H, m), 3.98 (8H, m), 5.53 (1H, dd, J=3, 10 Hz) and 7.40 (5H, m); $^{13}$C NMR (50 MHz, CDCl$_3$): δ16.1 (m), 63.9 (m), 73.1 (dd, J=7), 76.5 (dd, J=7), 128.0, 128.2, 128.4, 128.5, 129.0, 129.1 and 133.8; MS (EI): e/m 380.7 (M$^+$3.94) 379.6 (23.57) and 242.7 (100).

Reaction of the Phosphonate 22b with Sodium Ethoxide

To the phosphonate 22b (0.20 g, 0.5 mmol) was added a solution of sodium ethoxide (375 mg, 0.55 mmol) in EtOH (1.8 ml) and the mixture was stirred overnight. The solution was then neutralised by addition of saturated NH$_4$Cl (aq) (1 ml) and the mixture was extracted with EtOAc. The organic phase was washed with water, then brine and dried (MgSO$_4$). The residue obtained upon filtration and evaporation was subjected to flash chromatography (silica, 7:3 EtOAc/hexane,) to give ethyl benzoate, identified by comparison with an authentic sample.

Tetraethyl Benzylidenebisphosphonate (26)

The title compound was obtained from diethyl benzylphosphonate as described in the literature.[34] $^1$H NMR (200 MHz, CDCl$_3$): δ1.18 (12H, m), 3.74 (1H, t, J=25 Hz), 4.05 (8H, m) and 7.36 (5H); $^{13}$C NMR (50 MHz, CDCl$_3$): δ16.2, 45.7 (t, J=132 Hz), 63.5 (m), 127.7, 128.6, 129.9, 130.1, 130.2, 130.4, 130.5 and 130.6; MS (EI): 364.0 (M$^+$60.80).

Tetraethyl 1-phosphonyl(m-aminobenzyl)Phosphate (27)

To a solution of the phosphate phosphonate 19 (3.27 g, 8 mmol) in EtOH (15 ml) was added SnCl$_2$ (9.03 g, 40 mmol). The mixture was heated to 60° C. at which temperature an exothermic reaction started. The temperature was kept at 70° C. for 0.5 h and the resultant mixture was then brought back to room temperature and poured into an ice-cold, saturated solution of Na$_2$HPO$_4$ (aq) (150 ml). The resulting mixture was extracted with EtOAc, the organic phase was washed with brine and dried (MgSO$_4$). Filtration and evaporation afforded 3.02 g (99%) of 27 as a pale yellow colored liquid. IR (film): 3430, 3370, 2995, 1630, 1605, 1270 and 1050 (br); $^1$H NMR (200 MHz, CDCl$_3$): δ1.18 (12H, m), 3.97 (10H, m), 5.41 (1H, dd, J=3, 11 Hz) and 6.88 (4H, m); $^{13}$C NMR (50 MHz, CDCl$_3$): δ16.1 (m), 63.9 (m), 73.1 (dd, J=7 Hz), 76.6 (dd, J=7 Hz), 114.5, 114.6, 115.7, 115.8, 118.0, 118.1, 129.3, 134.6 and 146.8; HR-MS (EI): m/e 395.1265 (M$^+$C$_{15}$H$_{27}$NO$_7$P$_2$ requires 395.1262).

Tetraethyl Phosphonyl(1-m-phenyl-3,3-diethyltriazenyl)Methylphosphate (29)[58]

To BF$_3$.OMe$_2$ (60%, 3 mmol) kept at −15° C. was added a solution of the phosphonate 27 (0.96 g, 2.4 mmol) in CH$_2$Cl$_2$ (10 ml) over 5 min. After 10 min $^t$BuONO (0.36 g, 3.5 mmol) was added and the mixture was stirred for 0.5 h at 0° C. to give the diazonium salt 28. Pentane (20 ml) was then added and the resulting mixture was left in the cold overnight for phase separation. The solvent layer was decanted off and the residue was dissolved in CH$_2$Cl$_2$ (5 ml). To the resulting solution was added Et$_2$NH (0.76 g, 7.5 mmol) at 0° C., the solution was stirred for 0.5 h at ambient temperature and concentrated under reduced pressure. The deeply red colored residue was dissolved in CH$_2$Cl$_2$, the solution was washed with water, then brine and dried (MgSO$_4$). Filtration and evaporation furnished 0.86 g (74%) of 29 as a red colored oil. IR (film): 3020, 2970, 1270 and 1015; $^1$H NMR (200 MHz, CDCl$_3$): δ1.18 (18H, m), 3.72 (4H, q, J=7 Hz), 3.99 (8H, m), 5.53 (1H, dd, J=3, 11 Hz) and 7.40 (4H, m); $^{13}$C NMR (50 MHz, CDCl$_3$): δ12.9 (br), 16.2 (m), 73.3 (dd, J=7 Hz), 76.6 (dd, J=7 Hz), 120.0, 120.2, 121.3, 124.5, 124.6, 128.8, 134.2, 151.3 and 151.4; MS (EI): 479.0 (M$^+$1.41), 378.7 (100) and 224.8 (52.45).

Tetra(trimethylsilyl) Phosphonyl(1-m-phenyl-3,3-diethyltriazenyl)Methylphosphate (30)

To a solution of the ester 29 (0.39 g, 0.84 mmol) in CHCl$_3$ (5 ml) was added TMSBr (0.77 g, 5 mmol) at 0° C. and the resultant mixture was stirred for 3 h at ambient temperature. Evaporation of volatiles gave the title compound as a viscous liquid. Quantitative transesterification was achieved as determined by $^1$H and $^{13}$C NMR.

Tetraethyl Phosphonyl(m-iodobenzyl)Phosphate (32)

To a solution of the ester 29 (43 mg, 93 μmol) and NaI (16 mg, 106 μmol) in acetone (1 ml) was added TFA (30 μl) at 0° C. and the deeply red colored solution was stirred for 2.5 h at ambient temperature. The resulting mixture was extracted with CH$_2$Cl$_2$, the organic phase was washed with water, saturated NaHCO$_3$ (aq), then brine and dried (MgSO$_4$). Filtration and evaporation gave 27 mg (60%) of 32 as a brownish colored liquid.

$^1$H NMR (200 MHz, CDCl$_3$): δ1.21 (12H, m), 4.05 (8H, m), 5.48 (1H, dd, J=3, 11 Hz) and 7.44 (4H, m); $^{13}$C NMR (50 MHz, CDCl$_3$): δ17 (m), 64 (m), 72 (d), 75 (d), 94, 127, 129, 135, 136 and 137; HPLC; SAX (35 mM phosphate buffer, pH 2), R=8.5 min; HR-MS (EI): e/m 506.0117 (M$^+$C$_{15}$H$_{25}$O$_7$P$_2$I requires 506.0120).

Phosphonyl(m-iodobenzyl)Phosphoric Acid (31b)

To a solution of the ester 32 (27.2 mg, 52 μmol) in CHCl$_3$ (1 ml) was added TMSBr (0.15 g, 1 mmol) and the resulting mixture was stirred for 3 h. Volatiles were removed under reduced pressure, the residue was dissolved in EtOH (0.5 ml) and stirred overnight. Removal of solvent yielded a brownish colored residue. Quantitative hydrolysis was achieved as judged by $^1$H NMR.

m-Trimethylsilyltoluene (36)

A solution of m-chlorotoluene (12.66 g, 0.100 mol) and 1,2-dibromoethane (0.5 ml) in THF (20 ml) was added to magnesium turnings (2.67 g, 0.110 mol). The mixture was heated under reflux for 4 h, after which the heating bath was removed and trimethylchlorosilane (11.08 g, 0.102 mol) was added so that gentle reflux was maintained. The mixture was stirred for another 0.5 h and 5% NaHCO$_3$ (100 ml) was then added. The resulting mixture was extracted with CH$_2$Cl$_2$ (3×50 ml), the organic phase was washed with brine and dried (MgSO$_4$). Filtration and evaporation provided 15.05g (92%) of 36 as a pale yellow liquid. Spectroscopic data were identical to those previously reported in the literature.[40]

m-Trimethylsilylbenzyl Bromide (37)

A mixture of m-trimethylsilyltoluene (8.22 g, 50 mmol), NBS (8.90 g, 50 mmol), AIBN (0.05 g) and chlorobenzene (50 ml) was heated by means of a heating bath preheated to 110° C. An exothermic reaction started when the reaction mixture reached 80–90° C. and the orange suspension became a colorless solution within minutes. The mixture was cooled down with the aid of an ice-bath, ice water was added and the resulting mixture was extracted with hexane. The organic phase was washed with water, then brine and dried (MgSO$_4$). Filtration through a silica plug (10 g) followed by evaporation of solvents yielded 12.05 g (99%) of 37 as a colorless liquid. Spectroscopic data were identical to those reported in the literature.[43]

Diethyl m-trimethylsilylphenylethylphosphonate
(38)

To a solution of diethyl methylphosphonate (2.28 g, 15 mmol) in THF (20 ml) was added n-butyllithium (17 mmol, 1.6 M solution in hexane) at −78° C. After 45 min, the white suspension was added to a solution of the bromide 37 (3.65 g, 15 mmol) in THF (20 ml) and the mixture was stirred for 1.5 h. The temperature was then increased to −10° C. and after 1 h the deeply red colored solution was quenched by addition of saturated NH$_4$Cl (aq). Volatiles were removed under reduced pressure and the residue was purified by flash chromatography (silica, EtOAc) to give 2.48 g (53%) of 38 as a colorless liquid. IR (film): 3473, 2955, 1248, 1058 and 1031; $^1$H NMR (200 MHz, CDCl$_3$): δ0.30 (9H, s), 1.31 (6H, t, J=7 Hz), 2.10 (2H, m), 2.92 (2H, m), 4.11 (4H, m) and 7.29 (4H, m); $^{13}$C NMR (50 MHz, CDCl$_3$): δ−1.2, 16.4, 26.3, 28.6, 29.0, 61.5, 127.9, 128.4, 131.2, 132.9, 139.9, 140.2 and 140.7; HR-MS (EI): e/m 314.1453 (M$^+$C$_{15}$H$_{27}$O$_3$PSi requires 314.1467).

Tetraethyl m-trimethylsilylphenylethylidene-1,1-bisphosphonate (39)

A solution of the phosphonate 38 (2.51 g, 8 mmol) in THF (10 ml) was added to a solution of LDA (16 mmol) at −78° C. After 30 min diethyl chlorophosphate (1.41 g, 9 mmol) was added and the mixture was stirred for 45 min. The temperature was then increased to −25° C. and the reaction mixture was quenched by addition of saturated NH4Cl (aq). The mixture was concentrated under reduced pressure and the residue was extracted with hexane. The organic phase was washed with water, then brine and dried (MgSO$_4$). Filtration and evaporation provided 3.22 g (87%) of 39 as a pale yellow colored liquid. $^1$H NMR (200 MHz, CDCl$_3$): δ0.19 (9H, s), 1.21 (12H, m), 2.61 (1H, m), 3.19 (2H, m), 4.03 (8H, m) and 7.26 (4H, m); $^{13}$C NMR (50 MHz, CDCl3): δ0.5, 17.6, 32.5, 37.7, 40.3, 42.9, 63.4, 127.9, 129.6, 131.7, 134.0, 138.8, 138.9, 139.1 and 140.4; HR-MS (EI): m/e 450.1753 (M$^+$C$_{19}$H$_{36}$O$_6$P$_2$Si requires 450.1756).

m-Trimethylsilylphenylethylidene-1,1-bisphosphonate disodium salt (33)

Transesterification of the ester 39 (0.45 g, 1.0 mmol) was carried out as described under general procedures. The resulting tetra(trimethylsilyl) ester 40 was dissolved in EtOH (90%, 2.0 ml) at 0° C. and stirred for 30 min. NaOH (0.08 g, 2 mmol) in EtOH (90%, 4ml) was added to neutralise the mixture and subsequent removal of volatiles provided 33 as a white fluffy solid (0.43 g) in quantitative yield.

Tetraethyl m-iodophenylethylidene-1,1-bisphosphonate (41)

Iodination of the trimethylsilyl derivative 39 was carried out as described under general procedures to give the iodide 41 in high yield. IR (film): 3350, 2960, 1240, 1015 and 960; $^1$H NMR (200 MHz, CDCl$_3$): δ1.26 (12H, m), 2.57 (1H, m), 3.12 (2H, m), 4.07 (8H, m) and 7.39 (4H, m); $^{13}$C NMR (50 MHz, CDCl$_3$): δ16.3, 30.7, 36.2, 38.9, 41.5, 62.5, 93.9, 128.1, 129.8, 135.4, 137.8 and 141.9; HR-MS (EI): m/e 504.0365 (M$^+$C$_{16}$H$_{27}$O$_6$P$_2$I requires 504.0328).

m-Iodophenylethylidene-1,1-bisphosphonic acid
(34*c*)

The ester 41 was transesterified as described under general procedures. Hydrolysis was achieved by stirring the resulting tetra(trimethylsilyl) ester in EtOH (75%) overnight.

m-Trimethylsilylbenzyl cyanide (47)[48]

A mixture of KCN (5.5 g, 84 mmol), the bromide 37 (5.31g, 21.8 mmol), tributylamine (0.11 g, 0.59 mmol) and water (12.5 ml) was stirred overnight. The product was extracted with CH$_2$Cl$_2$ (3×30 ml), the extract was filtered through a silica plug (5 g) and solvent was removed under reduced pressure. The residue was distilled to give 2.27 g (55%) of 47 as a colorless liquid, bp. 134–136° C. (2 mm). IR (film): 2956, 2255, 1412, 1249, 885 and 867; $^1$H NMR (200 MHz, CDCl$_3$): δ0.31 (9H, s), 3.76 (2H, s) and 7.42 (4H, m); $^{13}$C NMR (50 MHz, CDCl$_3$): δ0.3, 24.3, 117.5, 127.7, 127.9, 128.6, 132.0, 132.3 and 141.2; HR-MS (EI): m/e 189.0972 (M$^+$C$_{11}$H$_{15}$NSi requires 189.0974).

m-Trimethylsilylphenylacetic acid (48)[45]

To a solution of NaOH (4.0 g, 0.1 mol) in MeOH (20 ml) was added the cyanide 47 (2.84 g, 15.0 mmol) and the mixture was heated under reflux for 4 h. The solvent was evaporated and the residue was dissolved in water (50 ml). The resulting solution was extracted with CH$_2$Cl$_2$ (2×20 ml). The aqueous phase was acidified with 85% H$_3$PO$_4$ to pH 2 and extracted with CH$_2$Cl$_2$ (3×30 ml). The extract was washed with brine, dried (MgSO$_4$) and solvent was removed under reduced pressure to give 2.93 g (94%) of 48 as a yellow colored liquid. IR (film): 3600–2600, 1717, 1418, 1254 and 847; $^1$H NMR (200 MHz, CDCl$_3$): δ0.32 (9H, s), 3.70 (2H, s) and 7.42 (4H, m); $^{13}$C NMR (50 MHz, CDCl$_3$): δ0.5, 41.6, 127.8, 129.6, 132.1, 132.3, 134.1, 140.8 and 177.7; HR-MS (EI): m/e 208.0918 (M$^+$C$_{11}$H$_{16}$O$_2$Si requires 208.0920).

Dimethyl m-trimethylsilylphenylacetylphosphonate
(50*a*)

To the acid 48 (1.04 g, 5.0 mmol) was added SOCl$_2$ (0.82 g, 6.9 mmol) and the mixture was stirred overnight. Toluene (2 ml) and then added and volatiles were removed under reduced pressure. The residue was dissolved in THF (5 ml) and trimethylphosphite (0.69 g, 5.5 mmol) was added at −20° C. The resulting solution was kept in an ultrasound bath at 0° C. for 30 min, after which the solvent was evaporated off to yield 1.63 g of a cream colored semisolid. The product decomposed upon exposure to the atmosphere. An analytical sample of 50*a* was prepared by washing the crude product with hexane and was shown to consist of a mixture of two stereoisomeric enols. The spectral data represents the major component. IR (film): 3600–2600, 1698, 1249 and 1036; $^1$H NMR (200 MHz, CDCl$_3$): δ0.19 (9H, s), 3.86 (6H, d, J 14Hz), 6.11 (1H, d, J 13 Hz), 7.46 (4H, m) and 7.92 (1H, d, J=7 Hz); $^{13}$C NMR (50 MHz, CDCl$_3$): δ0.7, 54.6, 117.5, 118.1, 128.1, 130.4, 132.9, 133.6, 134.0, 134.9, 138.3, 140.6 and 142.3; $^{31}$p (202 MHz; CDCl$_3$;

$H_3PO_4$): δ16.3; HR-MS (EI): m/e 300.0929 ($M^+C_{13}H_{21}O_4PSi$ requires 300.0947).

Dimethyl Phenylacetylphosphonate (50b)

This compound was prepared from phenylacetic acid (0.68 g, 5.0 mmol) as described for the preparation of the trimethylsilyl analogue 50a. The reaction furnished 1.17 g of 50b as a white solid, mp. 117–122° C. (hygroscopic). IR (film): 3600–2600, 1457, 1312, 1237 and 1053; $^1H$ NMR (200 MHz, $CDCl_3$): δ3.83 (6H, d, J=11 Hz), 6.07 (1H, d, J=12 Hz) and 7.52 (5H, m); $^{13}C$ NMR (50 MHz, $CDCl_3$): δ53.6, 116.3, 116.8, 127.2, 127.3, 127.9, 129.2, 133.7, 134.1, 137.8 and 141.9; $^{31}P$ (202 MHz; $CDCl_3$; $H_3PO_4$): δ16.1; HR-MS (EI): mi/e 228.0550 ($M^+C_{10}H_{13}O_4P$ requires 228.0551).

Tetramethyl 1-hydroxy(m-trimethylsilylphenyl)-ethylidene-1,1-bisphosphonate (51a)

To a solution of the phosphonate 50a (1.63 g, 5.0 mmol) in $Et_2O$ (10 ml) was added a solution of dimethylphosphite (0.83 g, 7.5 mmol) and dibutylamine (0.32 g, 2.5 mmol) in hexane (10 ml) at 0° C. A white solid began to form after a few minutes. After 20 min the mixture was filtrated to give 1.34 g (65%) of 51a as a white solid, mp. 114–118° C., When required, recrystallization was achieved by adding water (9.5 ml) to a solution of the title compound (0.50 g) in acetic acid (0.5 ml) and leaving the solution for several days in the cold. IR (film): 3700–2815, 2958, 1645 and 1251; $^1H$ NMR (200 MHz, $CDCl_3$): δ0.25 (9H, s), 3.38 (2H, t, J=14 Hz), 3.76 (12H, m) and 7.39 (4H, m); $^{13}C$ NMR (50 MHz, $CDCl_3$): δ0.1, 40.1, 54.9, 73.3, 76.3, 79.3, 127.7, 132.1, 132.4, 133.8, 136.6 and 140.2; $^{31}P$ (202 MHz; $CDCl_3$; $H_3PO_4$): δ20.7; HR-MS (EI): m/e 410.1080 ($M^+C_{15}H_{28}O_7P_2Si$ requires 410.1080).

Tetramethyl 1-hydroxyphenylethylidene-1,1-bisphosphonate (51b)

To a cold solution (0° C.) of dimethyl phosphite (0.22 g, 2.0 mmol) and diisopropylamine (0.05 g, 0.5 mmol) in $Et_2O$ (5 ml) the phosphonate 50b (0.46 g, 2 mmol) was added in portions during 30 min. After 1 h the mixture was filtered, the white solid was washed with cold $Et_2O$ and dried to give 0.54 g (80%) of 51b, mp. 122–124° C., IR (film): 3700–2800, 1645, 1216 and 1055; $^1H$ NMR (200 MHz, $CDCl_3$): δ3.35 (2H, t, J=14 Hz), 3.69 (12H, m) and 7.29 (5H, m); $^{13}C$ NMR (50 MHz, $CDCl_3$): δ39.1, 54.0, 72.4, 75.4, 78.4, 126.5, 127.3, 130.7 and 133.8; $^{31}P$ (81 MHz; $CDCl_3$; $H_3PO_4$): δ22.1; HR-MS (EI): m/e 338.0674 ($M^+C_{12}H_{20}O_7P_2$ requires 338.0684).

1-Hydroxy(m-trimethylsilylphenyl)Ethylidene-1,1-bisphosphonate Disodium Salt (45)

The ester 51a (0.82 g, 2.0 mmol) was transesterified as described under general procedures. The resultant tetra (trimethylsilyl) ester 52 was dissolved in EtOH (75%, 8 ml) at 0° C. and stirred for 0.5 h. The mixture was neutralised by addition of $Na_2CO_3$ (aq) (1.0 M, 3 ml) and filtered to give 0.75 g (94%) of 45 as a white solid.

Tetramethyl 1-hydroxy(m-iodophenyl)ethylidene -1,1-bisphosphonate (53)

The bisphosphonate 51a (0.41 g, 1.0 mmol) was added to a solution of ICl (0.32 g, 2.0 mmol) in acetic acid (2 ml) and the solution was stirred for 5 h. The solvent was evaporated and the residue was extracted with 1:1 hexane/$Et_2O$ (2×10 ml). Solvents were removed from the residue under reduced pressure furnishing 0.38 g (81%) of 53 as an orange colored liquid. IR (film): 3381 (br), 2958, 1643, 1216 and 1057; $^1H$ NMR (200 MHz, $CDCl_3$): δ3.18 (2H, t, J=14 Hz) 3.74 (12H, m) and 7.32 (4H, m); $^{13}C$ NMR (50 MHz, $CDCl_3$): δ39.7, 55.8, 56.3, 73.3, 76.3, 79.3, 94.2, 129.9, 130.8, 136.3, 136.8 and 140.2, $^{31}P$ (500 MHz; $CDCl_3$; $H_3PO_4$): δ19.6; HR-MS (EI): m/e 463.9630 ($M^+C_{12}H_{19}O_7P_2I$ requires 463.9651).

1-Hydroxy(m-iodophenyl)ethylidene-1,1-bisphosphonic acid (46c)

The iodo derivative 53 was hydrolysed as described under general procedures to give the title compound as an orange colored powder in quantitative yield. Reaction of dimethyl phenylacetylphosphonate (50b) with benzylamine To a solution of the phosphonate 50b in $CHCl_3$ (5 ml) was added molecular sieves (4A, 0.25 g) followed by benzylamine (0.11 g, 1 mmol). After 0.5 h a catalytic amount of TsOH was added and the mixture was stirred for 2 h. The mixture was filtered and flash chromatography (silica, 3:7 EtOAc/hexane) of the filtrate provided N-benzylphenylacetamide (61), as determined by comparison with an authentic sample.

BOC-Protected Diethyl Aminomethylphosphonate 62

The title compound was obtained from diethyl methylphosphonate in 42% yield by employing the method of Genet et al.[55] $^1H$ NMR (200 MHz, $CDCl_3$): δ1.34 (6H, t, J=7 Hz), 1.45 (9H, s), 3.56 (2H, m), 4.15 (4H, m) and 4.90 (1H); $^{13}C$ NMR (50 MHz, $CDCl_3$): δ16.8, 28.7, 34.9, 38.0, 62.8, 80.5 and 155.8; MS (EI): m/e 213.0 (2.13), 212.0 (31.66) and 138.0 (100).

Reaction of BOC-Protected Diethyl Aminomethylphosphonate 62 with LDA and Benzyl Bromide To a solution of phosphonate 62 (0.253 g, 1 mol) in THF (1 ml) was added LDA (1 mmol) at −78° C., After 15 min was added benzyl bromide (0.171 g, 1 mmol) in THF (1 ml), the mixture was stirred for 2.5 h and brought up to 0° C., After another 2 h the reaction was quenched by addition of saturated $NH_4Cl$ (aq). Work up as usual yielded 0.46 g of a yellow colored liquid. Flash chromatography (silica, hexane/EtOAc gradient) gave 0.19 g of 65 as a liquid.

m-Trimethylsilylphenylethylamine (68)[52]

To a suspension of $ZrCl_4$ (4.66 g, 20 mmol) in THF (70 ml) was added $NaBH_4$ (3.03 g, 80 mmol). This resulted in gas evolution and the formation of a cream colored suspension. The cyanide 47 (3.03 g, 16 mmol) was then added neat and the mixture was stirred for 24 h. After cooling to 0° C. the reaction was quenched by addition of water (100 ml), then 25% $NH_3$ (aq) until basic and extracted with EtOAc. The organic phase was washed with brine and solvents were removed under reduced pressure to give 3.65 g of a colorless liquid. The crude amine was purified by precipitation of the picric salt in benzene. The salt was then dissolved in water, the mixture was basified with LiOH and extracted with $Et_2O$. Remaining picric acid was removed from the organic phase by several washings with NaOH (aq). The organic phase was then washed with brine, dried ($MgSO_4$) and the solvent was evaporated to give 1.53 g (50%) 68, obtained as a pale yellow colored liquid. IR (film): 2954, 1248 and 858; $^1H$ NMR (200 MHz, $CDCl_3$): δ0.27 (9H, s), 1.49 (2H, br, NH2), 2.76 (2H, d, J=7 Hz), 2.98 (2H, d, J=7 Hz) and 7.28

(4H, m); $^{13}$C NMR (50 MHz, CDCl$_3$): δ0.37, 40.4, 43.8, 127.0, 128.4, 130.3, 133.8, 138.0 and 139.6; HR-MS (EI): m/e 193.1293 (M$^+$C$_{11}$H$_{19}$NSi requires 193.1287).

Tetraethyl N-(m-trimethylsilylphenylethyl)aminomethylenebisphosphonate (69)[53]

A mixture of the amine (68) (0.48 g, 2.5 mmol), triethyl orthoformate (0.44 g, 3.0 mmol) and diethyl phosphite (1.38 g, 10 mmol) was stirred at 150° C. for 1.5 h with continuous removal of the ethanol formed. The resulting mixture was brought back to room temperature and volatiles were removed under reduced pressure. The residue was subjected to flash chromatography (silica, 96:2:2 CH$_2$Cl$_2$/Et$_3$N/EtOH) to afford 0.86 g (72%) of 69, obtained as a yellow colored liquid. IR (film): 2981, 1678, 1244 and 1037; $^1$H NMR (200 MHz, CDCl$_3$): δ0.25 (9H, s), 1.31 (12H, m), 2.80 (2H, t, J=7 Hz), 3.14 (2H, t, J=7 Hz), 3.32 (1H, t, J=22 Hz), 4.17 (8H, m) and 7.27 (4H, m, Ar); $^{13}$C NMR (50 MHz, CDCl$_3$): δ–1.0, 16.5, 36.6, 51.7, 51.8, 54.4, 57.3, 63.1, 127.9, 129.2, 131.3, 133.8, 138.7 and 140.7; HR-MS (EI): m/e 479.1998 (M$^+$C$_{20}$H$_{39}$NO$_6$P$_2$Si requires 479.2022).

N-(m-Trimethylsilylphenylethyl) aminomethylenebisphosphonate Disodium Salt (66)

The tetra(ethyl) ester 69 (0.48 g, 1 mmol) was transesterified as described under general procedures. The resultant tetra(trimethylsilyl) ester was dissolved in a mixture of CH$_3$CN (2 ml) and MeOH (0.5 ml), and the solution was left in the cold for 5 h. A solution of NaOH (0.08 g, 2 mmol) in EtOH (2 ml) was then added. The resulting precipitate was collected by filtration and dried under reduced pressure to give 0.38 g (92%) of 66 as a cream colored solid.

Tetraethyl N-(m-iodophenylethyl)aminomethylenebisphosphonate (70b)

The trimethylsilyl derivative 69 was iodinated as described under general procedures to give the iodide 70b in high yield. IR (film): 2982, 1658, 1247 and 1042; $^1$H NMR (200 MHz, CDCl$_3$): δ1.29 (12H, m), 2.67 (2H, t, J=7 Hz), 3.06 (2H, m), 3.23 (1H, t, J=22 Hz), 4.14 (8H, m) and 7.24 (4H, m, Ar); $^{13}$C NMR (50 MHz, CDCl$_3$): δ16.1, 35.8, 50.8, 51.0, 53.9, 56.8, 63.0, 94.0, 127.7, 129.7, 134.8, 137.2 and 141.7; HR-MS (ESI) M+H$^+$: 534.0666 (C$_{17}$H$_{31}$NO$_6$P$_2$I, error 1.714e-04).

N-(m-Iodophenylethyl) aminomethylenebisphosphonic acid (67b)

Hydrolysis of the tetraethyl ester was carried out as described under general procedures to give the acid 67b in quantitative yield.

m-Trimethylsilylbenzylbenzenesulphone (74)[54]

Thiophenol (2.20 g, 20 mmol) was added to a solution of NaOH (0.80 g, 20 mmol) in MeOH (20 ml). To this solution was added a solution of the bromide 37 (4.38 g, 18 mmol) in MeOH (10 ml) and the mixture was stirred overnight. The residue obtained after concentration under reduced pressure was extracted with EtOAc. The organic phase was washed with water, then brine and dried (MgSO$_4$). Filtration and evaporation yielded m-trimethylsilylbenzenesulphide 4.79 g (98%) as a pale yellow colored liquid. The product (2.73 g, 10 mmol) was dissolved in MeOH (40 ml) and a suspention of oxone (18.44 g, 30 mmol) in water (40 ml) was added at 0° C. The reaction mixture was brought to ambient temperature and stirred overnight. The resulting mixture was extracted with CH$_2$Cl$_2$, the organic phase was washed with water, brine and dried (MgSO$_4$). Filtration and evaporation gave 2.84 g of a white solid, which was purified by chromatography on silica (Hexane/EtOAc gradient) to furnish 2.05 g (67%) of 74 as a white solid, mp 73–74° C., IR (neat): 2954, 1446, 1310, 1253 and 1155; $^1$H NMR (200 MHz, CDCl$_3$): δ0.18 (9H, s), 4.35 (2H, s) and 7.31(9, m); $^{13}$C NMR (50 MHz, CDCl$_3$): δ–1.2, 63.1, 127.6, 128.1, 128.8, 128.9, 131.4, 133.7, 135.7, 137.9 and 141.1; HR-MS (EI): m/e 304.0943 (M$^+$-Cl$_{16}$H$_{20}$O$_2$SiS requires 304.0953).

Diethyl 3-(m-trimethylsilylphenyl)-3-benzenesulphonyl-propyl-1-phosphonate (75)

To a solution of the sulphone 74 (3.04 g, 10 mmol) in THF (50 ml) was added LDA (10.5 mmol) at −78° C., The mixture was stirred for 0.5 h and diethyl 2-bromoethylphosphonate (2.45 g, 10 mmol) was then added neat. After 2 h the reaction was quenched by addition of AcOH (1 ml) at 0° C., Evaporation of volatiles followed by chromatography (silica, EtOAc) of the residue gave 3.08 g (66%) of 75 as a pale yellow colored liquid. IR (film): 2982, 2956, 1308, 1249 and 1056; $^1$H NMR (200 MHz, CDCl$_3$): δ0.13 (9H, s), 1.27 (6H, m), 1.70 (2, m), 4.09 (5H, m) and 7.20 (9H, m); $^{13}$C NMR (50 MHz, CDCl$_3$): δ-1.4, 16.3 (d, J=5 Hz), 20.8, 21.5, 24.4, 61.7 (d, J=7 Hz), 70.9, 71.2, 128.0, 128.5, 128.9, 129.5, 130.5, 133.4, 133.8, 135.1, 137.0 and 140.9; HR-MS (ESI); m/e M+H$^+$469.1628344 (C$_{22}$H$_{34}$O$_5$SiP, error 7.394e-04); HPLC: (PLRP 100 Å, 95:5 MeOH/H$_2$O), T$_R$=3.5 min, >95% purity.

Diethyl 3-(m-trimethylsilylphenyl)propyl-1-phosphonate (76)

To a solution of the phosphonate 75 (1.15 g, 2.45 mmol) in MeOH (25 ml) was added Na$_2$HPO$_4$ (3.48 g, 24.5 mmol) followed by Na(Hg) 6% (9.21 g, 24.5 mmol) at 0 C. The resulting mixture was stirred for 3 h and quenched by addition of saturated NH$_4$Cl (aq) (20 ml). The resulting mixture was extracted with Et$_2$O, the organic phase was washed with brine and dried (MgSO$_4$). Filtration and evaporation provided 0.77 g (96%) of 76 as a colorless liquid. IR (film): 2955, 1405, 1259, 1060 and 1032; $^1$H NMR (200 MHz, CDCl$_3$): δ0.28 (9H, s), 1.33 (6H, t, J=7 Hz), 1.86 (4H, m), 2.73 (2H, t, J=7 Hz), 4.10 (4H, m) and 7.28 (4H, m); $^{13}$C NMR (50 MHz, CDCl$_3$): δ–1.0, 16.5, 24.3, 25.2 (d, J=141 Hz), 36.7 (d, J=17 Hz), 61.5, 127.9, 129.0,131.2,133.5, 140.3 and 140.7; HR-MS (EI): m/e 328.1634 (M$^+$C$_{16}$H$_{29}$O$_3$P requires 328.1624); HPLC: (PLRP 100 Å, 95:5 MeOH/H$_2$O), T$_R$=4.2 min, >95% purity

Tetraethyl 3-(m-trimethylsilylphenyl)propyl -1,1-bisphosphonate (77)

To LDA (8.9 mmol) was added a solution of the diethyl 76 (1.40 g, 4.25 mmol) in THF (15 ml) at −78° C., After 0.5 h diethyl chlorophosphate (0.70 g, 4.5 mmol) was added neat and the resultant mixture was stirred for 2 h. The reaction was quenched by addition of acetic acid (0.5 ml) and the resulting mixture was concentrated to dryness under reduced pressure. Flash chromatography (silica, Et$_2$O/EtOH gradient) of the residue gave 1.86 g (94%) of 77 as a pale yellow colored liquid. IR (film): 2981, 1249, 1027 and 969; $^1$H NMR (200 MHz, CDCl$_3$): δ0.25 (9H, s), 1.32 (12H, m), 2.29 (3H, m), 2.91 (2H, t, J=7 Hz), 4.17 (8H, m) and 7.29 (4H, m); $^{13}$C NMR (50 MHz, CDCl$_3$): δ-1.3, 16.2, 27.2, 34.6, 35.6 (t, J=134 Hz), 62.4, 127.7, 128.9, 131.0, 133.4, 140.0 and 140.4; HR-MS (EI): m/e 464.1878 (M$^+$C$_{20}$H$_{38}$O$_6$P$_2$Si requires 464.1913).

Tetraethyl 3-(m-iodophenyl)propyl-1,1-bisphosphonate (78)

The trimethylsilyl derivative 77 (0.46 g, 1 mmol) was iodinated as described under general procedures to provide 0.46 g (86%) of 78 as a yellow colored liquid. $^1$H NMR (200 MHz, CDCl$_3$): δ1.26 (12H, m), 2.14 (3H, m), 2.28 (2H, t, J=7 Hz), 4.08 (8H, m) and 7.20 (4H, m); $^{13}$C NMR (50 MHz, CDCl$_3$): δ6.3, 26.9, 33.9, 35.5 (t, J=133 Hz), 62.4, 94.3, 127.8, 130.0, 135.1, 137.5 and 143.2; HR-MS (EI): m/e 518.0460 (M$^+$C$_{17}$H$_{29}$O$_6$P$_2$1 requires 518.0484).

3-(m-Trimethylsilylphenyl)propylidene-1,1-bisphosphonate disodium salt (71)

The ester 77 (0.23 g, 0.5 mmol) was transesterified as described under general procedures. The tetra(trimethylsilyl) ester was then dissolved in EtOH (75%, 1.5 ml) at 0° C., After 0.5 h was added a solution of NaOH (40 mg, 1 mmol) in EtOH (75%, 1 ml). Evaporation of volatiles furnished 71 as a white solid (0.20 g) in quantitative yield.

3-(m-Iodophenyl)propylidene-1,1-bisphosphonic acid (72c)

The ester 78 was hydrolysed as described under general procedures to give the title compound as a brownish powder in high yield.

EXAMPLES (SECTION C(II))

General

Radioactivity measurements were carried out either with a liquid scintillation counter (Beckman LS 6500, Beckman Instruments, USA) or with a Capintec CRC-7R radioisotope calibrator (Capintec, USA). Sodium [$^{131}$I]-iodide was obtained from NEN (NEN life science products, USA) and sodium [$^{125}$I]-iodide was purchased from Amersham (UK). HPLC separations were performed with one of the following systems: (i) an LKB Model 2150 pump and an LKB 2151 variable wavelength ultraviolet (UV)-detector combined with a Beckman Model 170 radioactivity detector (Beckman Instruments, USA). (ii) A LC10 AT pump and an SPD-M10A diode array UV detector, both from Shimadzu (Shimadzu Corporation, Kyoto, Japan) combined with a Beckman Model 170 radioactivity detector (Beckman Instruments, USA). The following columns were used: Supel cosil LC-Si (3 μm, Supelco), Supelcosil LC-18 (5 μm/25 cm, Supelco), Supelcosil LC-SAX (5 μm, 25cm×4,6 mm, Supelco), PLRP-S (5 μm, 100 Å, 150×1,6 mm, Polymer Laboratories, UK), PLRP-S (8 μm, 100 Å, 150×4,6 mm, Polymer Laboratories, UK) and TSKgel G 1000 HHR (300×7,8 mm, TosoHaas). Mixtures were sonificated with a Transsonic 310 ultrasoundbath (Heigar).

Production and Purification of $^{211}$At

The $^{209}$Bi (α, 2n)$^{211}$At reaction was employed for the production of $^{211}$At. The target consisted of a 0.25 mm thick layer of bismuth melted into a circular cave (r=12.7 mm, h=0.50 mm) on an aluminium target backing. The target was irradiated with 30 MeV alpha particle energy with maximum intensity of 10 μA for up to 3 h. The $^{211}$At was produced at the cyclotron (Scanditronix MC 35) at Section for Nuclear Physics, University of Oslo. Activities of up to 600 MBq was obtained at the end of the bombardment. Henriksen et al. have published a detailed description of the production method and the yields obtained as a function of beam energy, intensity and time.[75] Separation of the $^{211}$At from the target was achieved by either of two methods:

Method A: The target was placed in a quarts-still and heated to 650° C. in a custom built oven for 1 h. A stream of argon (20 ml/min) was used to facilitate transport of the astatine to a double cold-trap. Yields in the range of 40–60% were obtained, when measured as the total activity accumulated in the traps. Larsen et al. have published a detailed description of this method.[76]

Method B: The target was placed in a quarts-still and heated to 750° C. in a custom built oven. A stream of dry air (0.2 ml/min) was used to facilitate the transport of astatine from the target to a coil of silver, which was kept at a temperature below 100° C., After 30 min the oven was switched off. The still was then disassembled, the silver coil removed and placed in a glass tube equipped with a cold trap. The glass tub e was sea led with a stopper and heated to 500° C. for 15 min. Yields (measured as the activity present in the substance washed out from the trap) in the range of 10–60% were obtained. The method described above is a slightly modified version of the method of Doberenz et al.[73]

Preparation of n.c.a. phosphonyl(M-[$^{125}$I]-iodobenzyl)Phosphoric Acid (31a)

To an Eppendorf vial was added a solution Na $^{125}$I in water, followed by a solution of the tetra(trimethylsilyl) ester 30 (1 μmol, 66 μg) in CHCl$_3$ (10 μl). The mixture was concentrated to dryness with a stream of argon. To the residue was added acetone (100 μl) followed by TFA (10 μl). The vial was sealed, swirled and placed in a heating bath at 110° C. for 30 min. The product mixture was then dissolved in water (20 μl), filtered and purified by HPLC. For this purpose a SAX column was used with a mobile phase consisting of 35 mM phosphate buffer with pH 2.5. With a flow rate of 1 ml/min the iodide 31a eluted after 8.5 min. in an overall isolated yield of 8%. Prior to biological testing the n.c.a. iodide 31a was filtered through an AgCl column, neutralised with trisodium phosphate and filtered with a sterile filter (2 μm pore size).

Preparation of n.c.a. m-[$^{125}$I and $^{131}$I]-iodophenylethylidene-1,1-bisphosphonic Acid (34a and 34b)

To a solution of the radionuclide in water (2 μl) was added a solution of NCS (400 μg) in TFA (10 μl), followed by addition of the trimethylsilyl derivative 33 (100 μg, 0.2 μmol) in AcOH (2 μl). The resulting mixture was sealed, swirled and left for 5 min. The reaction mixture was analysed and purified by means of HPLC. For this purpose a PLRP-S column (100 Å) was used with a mobile phase consisting of 50 mM phosphate buffer with pH 7.2, to which 2% EtOH was added. With a flow rate of 1 ml/min the iodides 34ab eluted after 6.0 min. The radiochemical yield, as determined by integration, was >95%. However, the overall yield of isolated material was only 30%.

Preparation of m-[$^{211}$At]-astatophenylethylidene-1,1-bisphosphonic acid (79)

To a solution of $^{211}$At in CHCl$_3$ (3 μl) was added solution of NCS (400 μg) in TFA (10 μl), followed by addition of the trimethylsilyl derivative 33 (500 μg, 1 μmol) in AcOH (5 μl). The resulting mixture was sealed, swirled and placed in a heating bath at 60° C. for 5 min. To the reaction mixture was added water (100 μl) and the resulting mixture was analysed and purified with HPLC. For this purpose a PLRP-S coloumn (100 Å) was employed with a mobile phase consisting of 50 mM phosphate buffer with pH of 7.2, to which 2% EtOH was added. With a flow rate of 1 ml/min the astatide 79 eluted after 7.8 min. The radiochemical yield as determined by integration, was up to 92%, and the overall yield of isolated material was up to 39%. However, this method was capricious and frequently gave no yield at all.

Preparation of n.c.a 1-hydroxy(m-[$^{131}$I and $^{125}$I]-iodophenyl)-ethylidene-1,1-bisphosphonic acid (46a and 46b)

Method A: To a solution of the actual radionuclide (<50 MBq) in water (2 µl) was added a solution of NCS (400 µg) and AcOH (2 µl) in TFA (10 µl), followed by addition of the trimethylsilyl derivative 45 (100 µg, 0.2 µmol) in TFA (2 µl). The resulting mixture was sealed, swirled and left for 5 min. Prior to HPLC, 25% phosphoric acid (30 µl) was added and the mixture was placed in an ultrasound bath for 5 min.

Method B: A solution of n.c.a. $^{131}$I (<5 GBq) in water (<0.5 ml) was concentrated to about 10 µl with a stream of argon. To the resulting solution was added NCS (2 mg) and AcOH (10 µl) in TFA (40 µl), followed by addition of the trimethylsilyl derivative 45 (500 µg, 1 µmol) in TFA (5 µl). The resulting mixture was sealed, swirled and left for 0.5 h. Prior to HPLC, 30% $H_3PO_4$ (20 µl) was added and the mixture was then placed in an ultrasound bath for 10 min.

HPLC was carried out with a PLRP-S coloumn (100 Å) and a mobile phase consisting of 50 mM phosphate buffer with pH of 7.1, to which 2% EtOH was added. With a flow rate of 1 ml/min the iodides 46a and 46b eluted after 4.9 min. The radiochemical yield as determined by integration, was >95%. However, the overall yield of isolated material was only 30–45%.

Method A was used to prepare samples for biodistribution studies and method B was used to prepare samples for therapy studies. With the latter method, up to 0.7 GBq of the n.c.a. iodide 46a was isolated in 5–8 ml of the mobile phase. Prior to biological testing the samples were filtered through a sterile filter (2 µm pore size). In the case of biological testing of the non-purified compound, labelling was achieved with method B. The reaction mixture was then separated in two, one part (15 µl) was purified by HPLC and the other part (50 µl) was concentrated to dryness with a stream of argon, dissolved in phosphate buffer and sterile filtered. The latter sample contained about 125 µg bisphosphonate derivatives/ml.

Preparation of n.c.a N-(m-[$^{131}$I]-iodophenylethyl) aminomethylene-bisphosphonic acid (67a)

To a solution of Na$^{131}$I in water (2 µl) was added a solution of NCS (400 µg) in TFA (10 µl), followed by addition of the tetraester 69 (100 µg, 0.2 µmol) in AcOH (2 µl). The resulting mixture was sealed, swirled and left for 0.5 h. Analysis and purification was carried out by means of HPLC. For this purpose a PLRP-S (100 Å) column was used and the mobile phase consisted of 70:30:1 MeOH/H$_2$O/TFA. With a flow rate of 1 ml/min the iodide 70a eluted after 6.8 min. The yield as measured by integration, was 50%. The iodide was collected and the eluate was concentrated to dryness. The residue was dissolved in TMSBr (2.5 ml) and left overnight. Evaporation to dryness followed by addition of 75% EtOH (0.25 ml) provided the iodo derivative 67a. When this compound was subjected to HPLC under the conditions described above, only one peak appeared in the chromatogram with retention time of 2.7 min. Prior to biological testing the hydrolysed bisphosphonate was concentrated to dryness, dissolved in saline and sterile filtered (pore size 2 µm). The overall yield of isolated material was only 2%.

Preparation of n.c.a 3-(m-iodo-[$^{131}$I and $^{125}$I]-phenyl)propylidene-1,1-bisphosphonic acid (72a and 72b)

To a solution of the actual radionuclide in water (2 µl) was added a solution of NCS (400 µg) in TFA (10 µl), followed by addition of the trimethylsilyl derivative 71 (100 µg, 0.2 µmol) in AcOH (2 µl). The resulting mixture was sealed, swirled and left for 5 min. The reaction mixture was analysed and purified by means of HPLC. A PLRP-S coloumn (100 Å) was employed with a mobile phase consisting of 50 mM phosphate buffer with pH 7.3, to which 2% EtOH was added. With a flow rate of 1 ml/min the iodides 72a and 72b eluted after 5.9 min. The radiochemical yield as determined by integration, was >95%. However, the yield of isolated material was only 30%. Prior to biological testing the sample was filtrated with a sterile filter (2 µm pore size). In the case of 72a, the iodide 46c (250 µg, 0.5 µmol) was added to the reaction mixture prior to HPLC in order to facilitate subsequent analysis and purification.

EXAMPLES (SECTION C(III))

Preparation of the Labelled Compounds

The n.c.a. labelled compounds 31a, 34a, 46a, 67a and 72a were prepared as described in section 3.5, Experimental Part II. The compounds were used within one week after preparation.

Animals

Biodistribution and antitumour efficacy studies were performed in healthy athymic nude mice (balb/c, nu/nu) and congenitally athymic nude rats (Han rnu/rnu Rowett) of both sexes. The weight of the animals is specified for each experiment. Rats were anesthetized with 0.3 ml/100 g of a mixture with equal parts of fentanyl/fluanison (Hypnorm®, Janssen, Beerse, Belgium) and midazolam (Dormicum®, Roche, Basel, Schwitzerland) during the surgical procedures. The animals were bred in the nude rodent facility at the Norwegian Radium Hospital, maintained under specific pathogen-free conditions, and food and water were supplied ad libitum. Housing and all procedures involving animals were performed according to protocols approved by the animal care and use committee, in compliance with the National Committee for Animal Experiment's guidelines on animal welfare.[89, 90]

Biodistribution Studies

Mice. Samples of 100 µl containing 50,100, 400, 140 or 45 KBq of 31a, 34a, 46a, 67a or 72a, respectively, were injected into the tail veins as single bolus injections. No sign of discomfort or toxicity was observed after administration of samples. At 0.5 h, 2 h, 5 h and 24 h postinjection times the animals were sacrificed; except in the case of the phosphate phosphonate derivative 31 were the animals were sacrificed 0.25 h, 2 h, 5 h and 24 h postinjection. Randomly selected groups of three animals were used at each time point. The whole animals were weighed and dissected. The excised organs, i.e. femur, skull, blood, heart, lung, liver, kidney, spleen, stomach, large intestine and small intestine, were weighed separately prior to counting.

Rats. Samples of 200 µl containing 4 or 0.4 MBq of nonpurified or HPLC-purified 46a, respectively, were injected into the tail veins as single bolus injections. At 24 h postinjection the animals were sacrificed, weighed and dissected. Randomly selected groups of three animals were used for each sample. The excised organs, i.e. femur, skull, blood, heart, lung, liver, kidney, spleen, stomach, large intestine and small intestine, were weighed separately prior to counting.

Pharmacokinetics in mice. Two animals weighing 20 g and 28 g were anaesthetized and given 250 μl single bolus tail vein injections containing 12 MBq of 46a. The animals were placed under a gamma camera and 2 min frames were collected for the following 2 h. The presented data refers to the animal weighing 20 g.

Tumour lesion to healthy bone ratio. A rat weighing 114 g was given a single bolus tail vein injection of 15 MBq (500 μl) of 46a seven days after inoculation with 1×10$^6$ MT-1 cells. The animal was sacrificed 24 h postinjection. The whole animal was then placed under a gamma camera and images were obtained. The spine was then excised and cut into slices of 10 μm. The slices were molded in Epon and images were obtained with a beta camera.

Antitumour Efficacy Studies

Initially, a skeletal metastases model in nude rats, including the human breast carcinoma line MT-1 (1) was tested. A total of 1×10$^6$ cells were injected into the left vintricula of the heart (L.V.) of 4–5 weeks old nude rats (2). A primary osteogenic sarcoma model in nude rats, was established by intratibial (i.t.) injection of 1×10$^6$ OHS cells (3–5). A total of 20 animals, allocated in four groups (n=5 for each group) were used for both cell lines. The animals inoculated with MT-1 cells were treated with 200, 300 or 400 MBq/kg of 46a seven days after cell injection. The animals inoculated with OHS cells were treated with 100, 200 or 400 MBq/kg of 46a seven days after cell inoculation. The control groups (MT-1 and OHS) received saline only. Doses were corrected for the actual weight of each animal and administered by single bolus tail vein injections.

Radioactivity Measurements

Radioactivity measurements of the labelled compounds were carried out with a liquid scintillation counter (Beckman LS 6500, Beckman Instruments, USA) or with a Capintec CRC-7R radioisotope calibrator (Capintec, USA). The radioactivity level of the excised organs was measured with an automated gamma counter (LKB Wallac 1282, Turku, Finland).

Scintigraphy

A gamma camera (ADAC, USA) equipped with a 6 mm pinhole collimator was used. Dynamic data were acquired using a 128×128 matrix size, the field of view was zoomed to the middle 25×25 cm of the camera, and 2 min frames were collected for 2 hours.

Bioscope

A prototype real time autoradiography system (Bioscope 3225, IDEAS, Høvik, Norway) consisting of a double sided multiple strip silicon detector was used to obtain images of bone slices.

RESULTS AND DISCUSSION

Biodistribution

Biodistribution in Mice

Tables 4–7 show the % injected dose per gram of organ (% ID/g) at 0.5 (0.25 in the case of 31a), 2, 5 and 24 hours postinjection of the radioiodinated compounds 31a, 34a, 46a, 67a and 72a in balb/c mice. The data and Tables are presented in FIGS. 11–14.

Since radioiodine is known to accumulate in the thyroid, high uptake in this organ is indicative of dehalogenation in vivo.[77] Accordingly, tissue samples containing the thyroid were systematically collected and their radioactivity levels measured. Administration of the phosphate phosphonate 31a resulted in uptake of 0.13±0.03% of the injected dose in the thyroid at 24 h postinjection, while the corresponding uptake for the bisphosphonates 34a, 46a, 67a and 72a was 0.06±0.04% or below. At this level, the uptake is of the same order as for other soft tissues, indicating an extraordinary high stability in vivo.

The phosphate phosphonate 31a was rapidly excreted through the kidneys, resulting in low uptake in all organs 2 h postinjection. At 24 h postinjection, uptake in femur was 2.05±0.49% ID/g and that of the skull 1.22±0.19% ID/g. At the time of question, the highest uptake in soft tissues was found in the kidneys (0.08±0.02% ID/g, 24 h). Therefore, the femur to soft tissue ratio was excellent (>25).

The bisphosphonate 34a accumulated fast with high preference for bone. The uptake in femur 0.5 h postinjection was 18.8±0.51% ID/g and that of the skull was 10.28±2.58% ID/g. The blood clearance was rapid (blood; 2.22±0.31% ID/g, 0.5 h) and the uptake in soft tissues was generally low, except in the kidneys (8.23±6.39% ID/g, 0.5 h). However, the compound was efficiently excreted from this organ and 24 h after administration uptake in the kidneys was low as well (1.06±0.10% ID/g). As there was no significant leakage of the compound from bone tissues (femur 15.25±4.89% ID/g and skull 7.13±2.73% ID/g, 24 h) the resulting femur to soft tissue ratio was high (>14, 24 h).

A superior bone affinity was found for the hydroxy-bisphosphonate 46a, with uptakes of 45.03±6.75 and 24.61±3.85% ID/g 0.5 h postinjection in femur and the skull, respectively. The activity in blood was initially high (15.92±12.75% ID/g), but dropped down to 1.36±0.25% ID/g after 2 h. The uptake in kidney was initially high as well (18.64±1.78% ID/g, 0.5 h). However, clearance from this organ was fairly rapid with an uptake of 5.16±2.00% ID/g after 24 h. A somewhat lower uptake was found in the liver (2.27±0.69% ID/g, 24 h) and the uptake in other soft tissues was negligible at this time. The uptake in bone reached a peak after 2 h (femur; 45.54±4.10% ID/g) and remained very high (femur; 37.79±11.78% ID/g, 24 h) resulting in a femur to soft tissue ratio of 7 or above.

The aminomethylenebisphosphonate 67a appeared to lack bone seeking properties as the uptake in femur was only 1.39±0.43% ID/g after 24 h, and that of the skull as low as 0.91±0.08% ID/g. In addition, the compound had a rather high uptake in soft tissues. The highest uptake was found in the liver (5.57±0.79% ID/g, 24 h) and the spleen (2.49±0.37% ID/g, 24 h).

The propylidenebisphosphonate 72a had a high bone affinity with uptakes of 10.36±4.26% ID/g in the skull and 8.84±0.97% ID/g in femur at the 24 h time point. It is worth mentioning that uptakes in femur and that of the skull were similar for this compound, while the other compounds accumulated preferentially in femur and to a less extent in the skull. The uptake in soft tissues was very low for this compound, with radioactivity levels of 0.85±0.08% ID/g and 0.35±0.06% ID/g detected in the kidneys and liver at 24 h postinjection, respectively.

The low bone affinity found for the phosphate phosphonate 31a could be expected from its molecular structure;

however, the apparent lack of bone-seeking properties observed for the aminomethylenebisphosphonate 67a was surprising. Aminobisphosphonates are among the most potent inhibitors of bone resorption known, a property believed to be dependent of their high bone affinity.[78] Since 67a was administered at a n.c.a. level, minor impurities in the sample may have affected the biological properties of the compound. The possibility of in vivo dehalogenation is less likely as uptake in the thyroid was at the same level for this compound as for the other bisphosphonates.

Of the compounds tested, the hydroxybisphosphonate 46a and the alkylidenebisphosphonates 34a and 72a were found to be potent bone-seekers. The latter compounds were more selective for bone; however, the hydroxybisphosphonate 46a was superior with respect to bone affinity. Eventually, bone affinity was given primary consideration and the hydroxy-bisphosphonate 46a was selected for further studies.

Biodistribution in Rats

Figure 15:
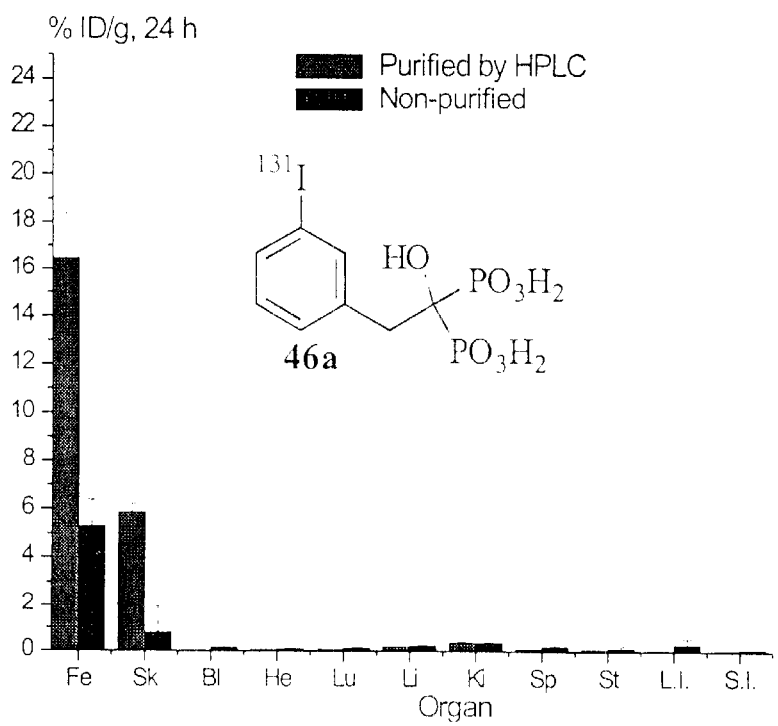
FIG. 15 shows the biodistribution of i.v. administered 46a 24 h postinjection in congenitally athymic, nude rats (Han:rnu/rnu Rowett) weighing 60 g. The values are the means of three rats with error bars representing the standard deviation. Abbreviations: Fe; femur, Sk; skull, Bl; blood, He; heart, Lu; lung, Li; liver, Ki; kidney, Sp; spleen, St; stomach, L.I.; large intestine, S.I.; small intestine.
Figure 16:
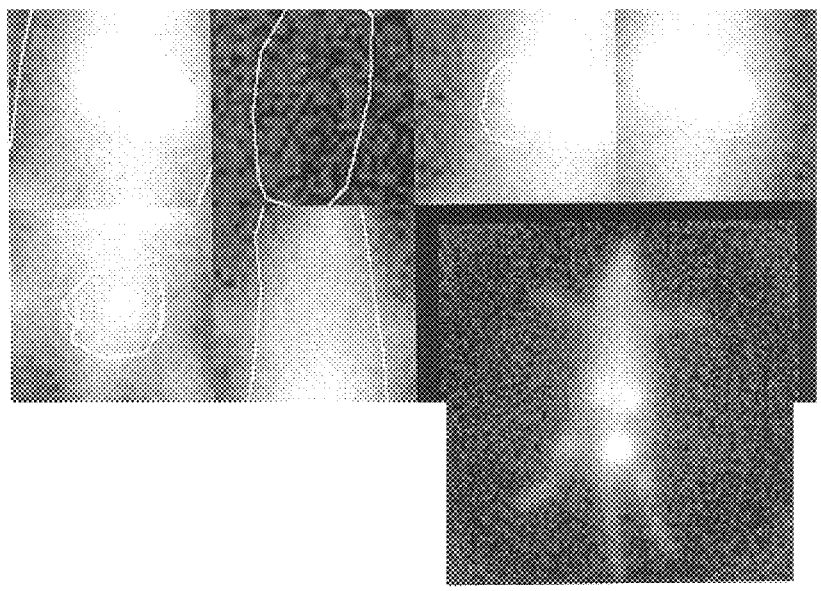
FIG. 16 shows a photographic image. The images show the regions from which the dynamic curves were derived. The inserted image corresponds to the whole body.
Figure 17:
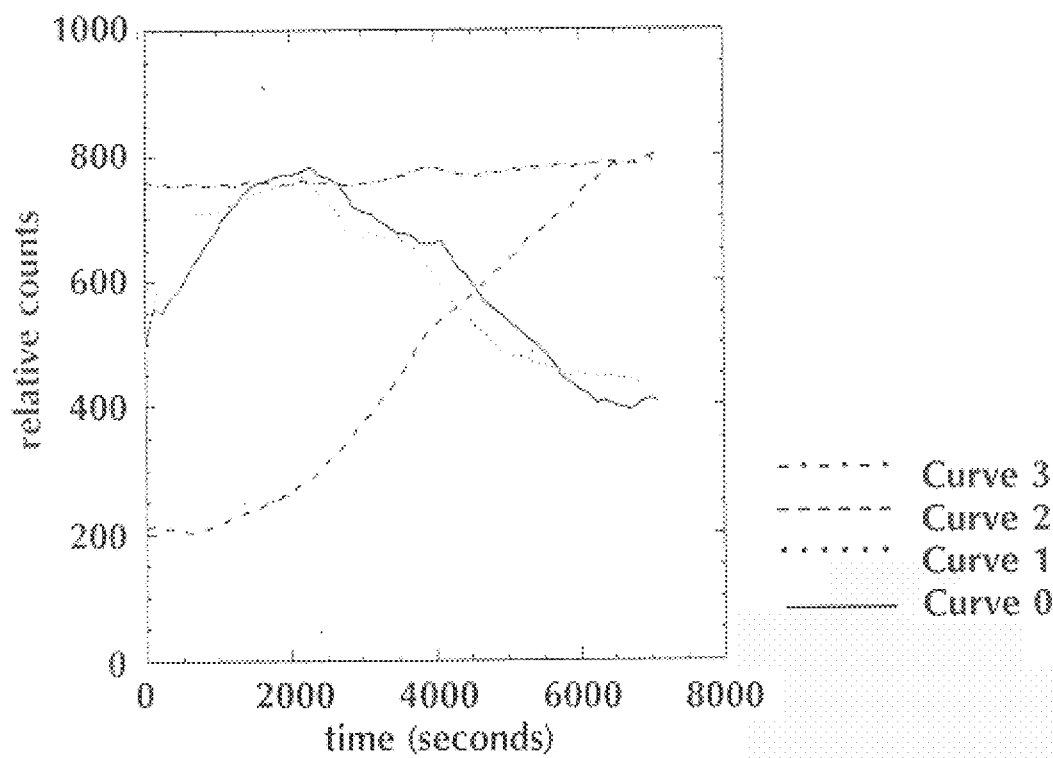
FIG. 17 shows the dynamic curves derived from the regions illustrated in FIG. 16. The curves represent detected radioactivity and correspond to: kidneys (curve 0 and 1), bladder (curve 2) and whole body (curve 3).

To further evaluate the hydroxybisphosphonate 46a, biodistribution of this compound was obtained in rats. The goal of this experiment was to find whether there was a difference in the properties of the HPLC-purified compound as compared with a nonpurified sample. The results are given in Table 8 and are also presented in FIG. 15.

In the case of the HPLC-purified sample, a superior bone affinity was found in rats. At the 24 h point of time, uptakes of 16.44±1.96% and 5.84±0.35% ID/g were found in femur and the skull, respectively. Moreover, uptake in soft tissues was very low, the highest uptake being that of the kidneys (0.36±0.03% ID/g, 24 h). As a result the femur to soft tissue ratio was excellent (>45, 24 h). A high selectivity for bone was found for the nonpurified compound as well with femur to kidney ratio of 14; however, the uptake in femur (5.28±1.10% ID/g, 24 h) was only one-third of that obtained with the HPLC-purified sample.

It is known that rapid infusion of bisphosphonic acids may lead to formation of calcium-bisphosphonate complexes. The ability to form such complexes differs from compound to compound, but it is generally high. For example, an infusion rate below 60 mg/h of pamidronate is required to maintain optimal bioavailability for this compound.[79] The nonpurified sample contained about 125 µg/ml and was given as single bolus injections of 0.2 ml. Consequently, the relative lower bone affinity found for this sample may have been caused by reduced bioavailability due to complex formation.

The results obtained with the nonpurified sample were remarkable for two reasons: (i) the selectivity for different bone tissues was the highest observed in this study, with femur to skull ratio close to 7. (ii) In addition, the uptake in the thyroid was very low; although no measures were taken to remove unreacted iodine from the sample or to block uptake in the thyroid gland, only 0.03±0.01% of the total injected radioactivity was detected in this gland.

In order to avoid extensive experiments required to determine the cause of the relatively lower bone uptake found for the nonpurified sample, we decided to use the HPLC-purified compound in further studies. However, if a slower infusion rate of the nonpurified hydroxy bisphosphonate 46a results in high bioavailability, laborious HPLC purification may not be required for biological applications of this compound.

Pharmacokinetics in Mice

The progression from intravenous injection of the hydroxybisphosphonate 46a in mice (balb/c, 20 g) was monitored by means of scintigraphy for 2 h. Images were obtained and dynamic curves for the radioactivity detected in the kidneys and bladder were derived by interactively drawing regions around structures of interest (FIG. 9). As can be seen from the resulting graph (FIG. 7), the whole body curve increases with time. This is due to the increased sensitivity in the middle of the image, where the accumulation occurs in the kidneys and bladder.

The analysis shows that 27% of the injected activity has accumulated in the bladder after 2 hours. Furthermore, uptake in the kidneys reached a peak at 45 min postinjection, amounting to 7.5% (adding left and right kidney) of the injected dose. From that point of time, the biological half-life in the kidneys was 50 min. The bladder curve was still increasing after 2 h, resulting in estimates of 35% excretion and 65% retention of the injected dose.

The pharmacokinetics of polyphosphonates in different species, varying from rodents to humans, is known to relate to weight by the expression:[80]

Corr. Factor=(mass man/mass animal)$^{0.33}$

In our case, this translates to a correction on the time scale of a factor of 15.1

Bone Lesions to Healthy Bone Ratio

Figure 18:
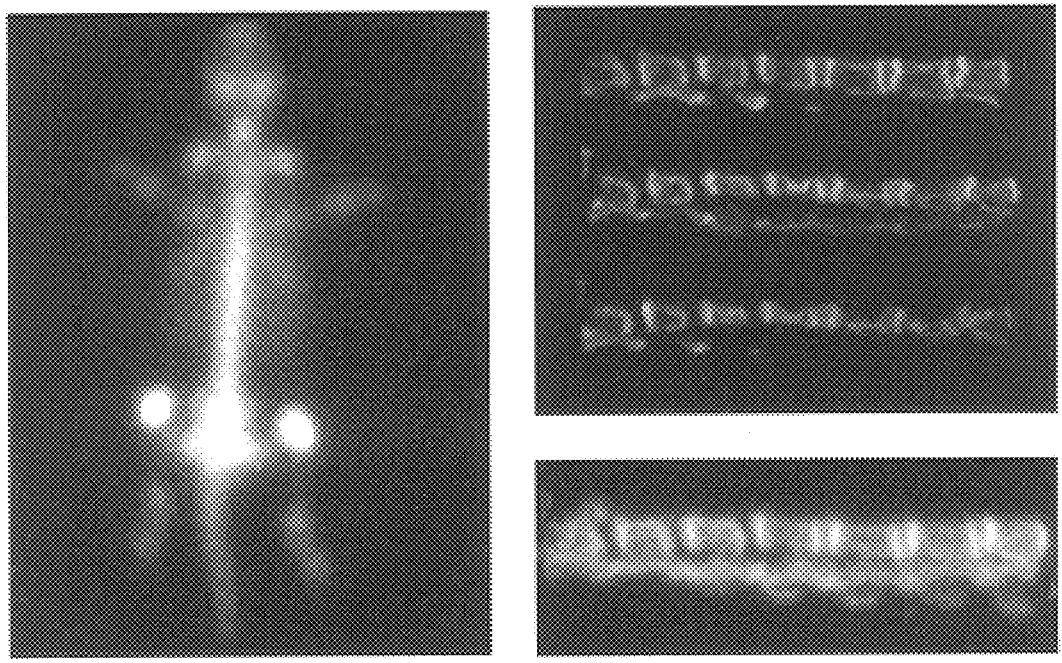
FIG. 18 shows the image at the left side was obtained by scintigraphy of a rat (114 g) 24 h after administration of 46a. The upper images to the right are selected slices of the spine (Bioscope). The structure below appeared when these images were added in layers.

In order to obtain ratios of bone cancer lesions to healthy bone, the hydroxybisphosphonate 46a was injected into a rat inoculated with MT-1 cells (a human breast cancer cell line, see section 4.2.3.1.) seven days earlier. The animal was sacrified 24 h postinjection and whole body images were obtained by means of scintigraphy. No tumours were depicted, but the high affinity and selectivity for bone previously demonstrated for this compound was confirmed. The radioactivity distributions in slices of the spine were then measured with a device (Bioscope) for real time autoradiography. The resulting images were automatically aligned by means of an image correlation method (Personal communication Arne Skretting, The Norwegian Radium Hospital, Oslo). Finally, the aligned images were added in layers to reconstruct the whole spine. The resulting structure clearly confirms the validity of this method (FIG. 18). Abnormal uptake was detected in one slice only. Furthermore, subsequent staining of this slice failed to identify any MT-1 cells. Accordingly, the results obtained were inconclusive.

Dose Estimates

Estimates of the doses resulting from administration of the $^{131}$I labelled hydroxybisphosphonate 46a in 'reference man' were calculated with MIRDOSE (3.1). The dose estimates are given in Table 9. For the purpose of comparison with older literature, the values are expressed in both mGy/MBq and rad/mCi. The estimates are based on biodistribution data from the dynamic study, described in section 4.2.1.3, and condition upon the compound being adsorbed on bone surfaces.

Administration of 1.00 GBq of the compound is estimated to result in doses of 1.10 Gy to the bone marrow and 7.44 Gy to bone surface. The corresponding dose to the urinary bladder is 0.09 Gy.

In comparison, the doses resulting from administration of 1.00 GBq of $^{153}$Sm-EDTMP are 1.20–2.00 Gy to the bone marrow, 5.3–8.8 Gy to bone surface and 0.4–1.3 Gy to the bladder. In the case of $^{153}$m-EDTMP, doses were first estimated from kinetical studies in rat, and were later confirmed by clinical data.[81]

In general, estimates of the actual dose delivered to tumours is problematic in that bone-seeking compounds concentrate in bone cancer lesions and irradiate the tumour cells by virtue of their proximity. Additionally, uptake of therapeutic compounds is known to be extremely variable from patient to patient. Finally, tumour doses will depend on actual volumes and growth rate of the tumour.[82]

TABLE 9

Output from the MIRDOSE (3.1) program assuming residence times equal to 28, 153, 10 and 3 hours in trabecular bone, cortical bone, kidneys and remainder of body, respectlively.

| TARGET ORGAN | TOTAL DOSE mGy/MBq rad/mCi |
|---|---|
| 1) Adrenals | 2.24E-01 8.28E-01 |
| 2) Brain | 2.49E-01 9.21E-01 |
| 3) Breasts | 7.78E-02 2.88E-01 |
| 4) Gallbladder Wall | 9.63E-02 3.56E-01 |
| 5) LLI Wall | 1.54E-01 5.68E-01 |
| 6) Small Intestine | 1.18E-01 4.36E-01 |
| 7) Stomach | 8.81E-02 3.26E-01 |
| 8) ULI Wall | 1.06E-01 3.91E-01 |
| 9) Heart Wall | 1.22E-01 4.50E-01 |
| 10) Kidneys | 1.70E-01 6.29E-01 |
| 11) Liver | 1.06E-01 3.92E-01 |
| 12) Lungs | 1.42E-01 5.24E-01 |
| 13) Muscle | 1.57E-01 5.80E-01 |
| 14) Ovaries | 1.33E-01 4.93E-01 |
| 15) Pancreas | 1.38E-01 5.12E-01 |
| 16) Red Marrow | 1.10E+00 4.07E+00 |
| 17) Bone Surfaces | 7.44E+00 2.75E+01 |
| 18) Skin | 1.18E-01 4.36E-01 |
| 19) Spleen | 1.07E-01 3.94E-01 |
| 20) Testes | 9.32E-02 3.45E-01 |
| 21) Thymus | 1.06E-01 3.91E-01 |
| 22) Thyroid | 1.62E-01 5.98E-01 |
| 23) Urin Bladder Wall | 8.78E-02 3.25E-01 |
| 24) Uterus | 1.05E-01 3.90E-01 |
| 27) Total Body | 4.67E-01 1.73E+00 |
| 28) EFF DOSE EQUIV | 4.79E01.77E+00 |
| 29) EFF DOSE | 3.28E-01 1.21E+00 |

Bisphosphonates are known to accumulate to a much higher degree in bone lesions then in healthy bone, e.g. tumour lesions to normal bone ratios of about 10:1 has been found in the case of $^{186}$Re HEDP.[11] Based on the dose estimates obtained for the hydroxybisphosphonate 46a, lesion to healthy bone dose ratios of this magnitude would result in tumour doses of 74 Gy/GBq. At this level the prospect of curation is good.

Studies of Antitumour Effect

The hydroxybisphosphonate 46a was evaluated in two antitumour efficacy studies, including human breast cancer cells (MT-1) and human osteosarcoma cells (OHS) in immuno-deficient nude rats.

The MT-1 Model

The MT-1 model simulates formation of mixed lytic/sclerotic skeletal metastasis in breast cancer patients. The model had recently been established in immuno-deficient rats by injections into the left ventricula (L.V.) of the oestrogen receptor-negative human breast cancer (MT-1) cell line.[83,84,85] In this model, large masses of tumour cells build up in the spine, replacing the normal bone marrow and eroding the bone part of the spine. Consequently, the animals develop hind-leg paralysis or become inactive with a kyfotic (hunchback) posture after a mean lag period of about 20 days.

The MT-1 cell line has an aggressive and metastatic behaviour and animals infected develop tumours in the brain, lung and adrenals as well. Repeated treatments (days 7 and 14) with the chemotherapeutic agents cisplatin and doxorubicin have not improved survival nor did they have any significant effect on the metastatic growth.

Figure 19:
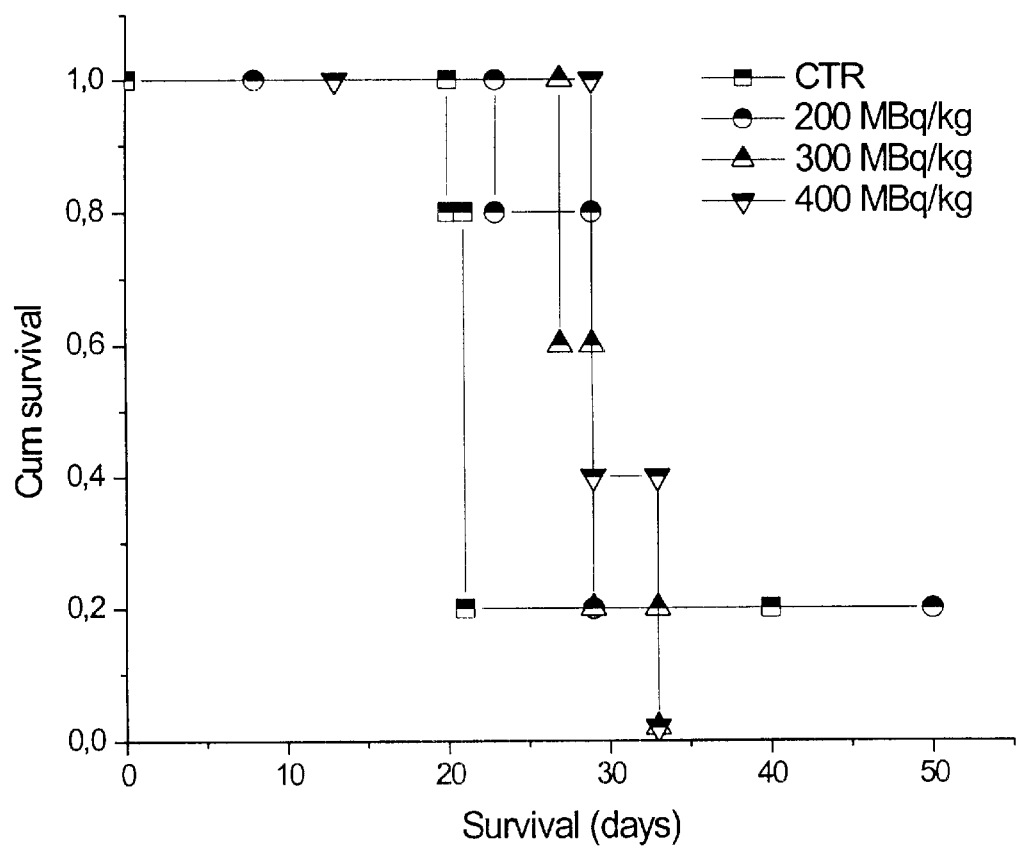
FIG. 19 shows the survival curves for rats injected (L.V.) with MT-1 cells. A total of 20 animals, allocated in four groups (n=5 in each group), were used. Seven days after cell injection the animals were treated with 200, 300 or 400 MBq/kg of 46a, whereas the control group received saline only.

Treatment with the hydroxybisphosphonate 46a was initiated 7 days after tumour cell inoculation, while the control group received saline only. As shown in FIG. 19, the rats in the control group developed tumours with a mean survival time of 20.8 days (range 20–21, one survivor). In comparison, the mean survival times for the animals treated with 46a were 27.5 days (range 23–29, one survivor), 29.0 days (range 27–33) and 30.6 days (range 29–33) with increasing dose of 200, 300 and 400 MBq/kg, respectively (n=5 in each group). Survival time refers to the time from cell inoculation until the animals suffered discomfort due to their metastatic condition and hence were sacrificed.

One long time survivor was observed in the control. One long time survivor was also found in the group receiving the lowest dose. Consequently, the observed long time survival may be interpreted as cases where the cell line failed to establish metastasis in the actual animals, or behaved atypically. If the two long time survivors are excluded from the data, the increased survival time found for the animals treated with 46a as compared with the controls, are statistically significant (p<0.05, Wilcoxon rank-sum test) at all three dose levels. It was indications of a dose-response relationship as well, but this was not statistically significant.

The OHS Model

The OHS model had been established by intratibial injections of the osteogenic sarcoma (OHS) cell line in immuno-deficient rats.[86,87] Eventually, the rats develop palpable tibial tumours. At the time of treatment (7 days after cell inoculation) the tumours fill approximately 50–60% of the tibial cavity and have a substantial osteoid production closely resembling that of osteoblastic osteosarcomas in the clinic.[88] The model has been used to evaluate the antitumour efficacy of several drugs currently used in the treatment of bone-related cancer.

Disease-free latency was defined as the period between tumour cell inoculation and the time the diameter of the tumour-injected tibia had increased by 2–3 mm compared with that of the non-injected contralateral leg.

Figure 20:
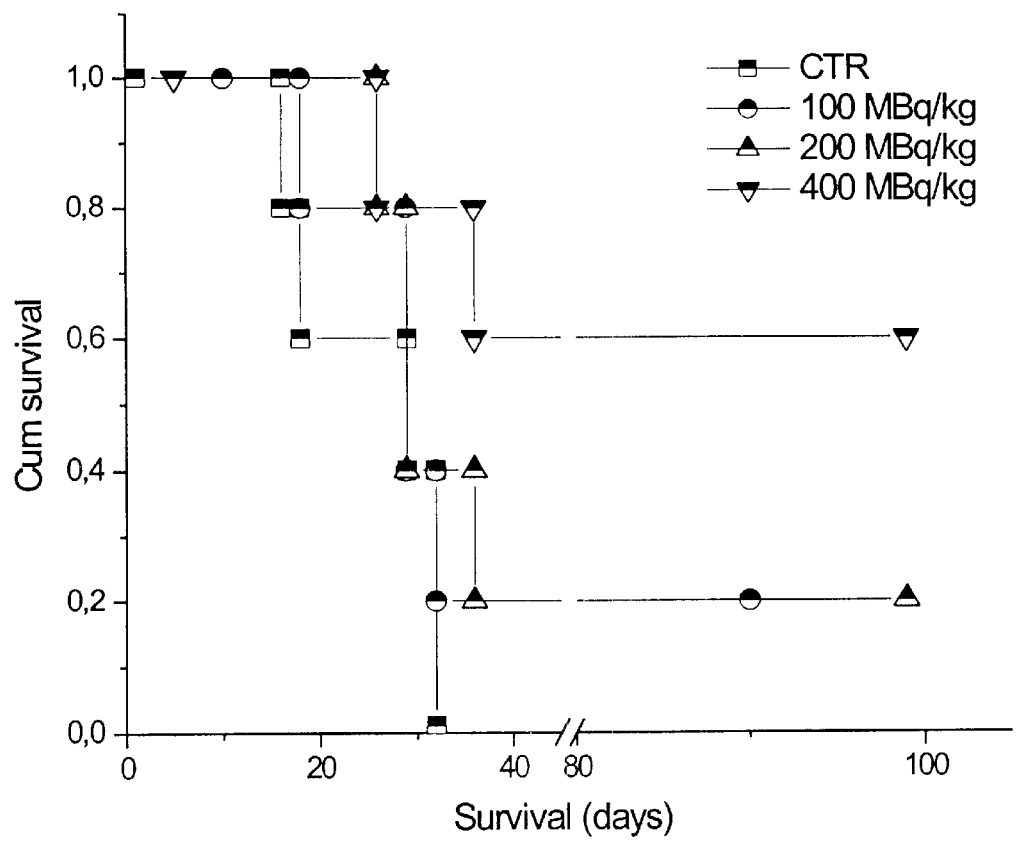
FIG. 20 shows the survival curves for rats inoculated with OHS cells. A total of 20 animals, allocated in four groups (n=5 in each group), were used. Seven days after cell inoculation the animals were treated with 100, 200 or 400 MBq/kg of 46a, whereas the control group received saline only.

As shown in FIG. 20, all the untreated, OHS-injected control animals (5/5) developed palpable bone tumours after 16–32 days (mean 25.4 days). In comparison, the mean disease-free latency was 27 days (range 18–32, one survivor), 30 days (range 26–36, one survivor) and 31 days (range 26–36, 3 survivors) for the animals treated with 100, 200 and 400 MBq/kg of 46a, respectively (n=5 in each group).

The group receiving the highest dose had a marked increase in disease-free latency time (P <05, Kruskal-Wallis test) as compared to the other groups. In addition, 3 of 5 (60%) animals receiving the highest dose were long time survivors. Furthermore, 5 of 15 (33%) animals treated with the compound were long time survivors (>100 days), while all controls developed palpable tumours (5/5, <33 days).

In comparison, Windem et al. reported 62% (8/13 rats, 60 days) survival rate of OHS-inoculated rats treated with $^{153}$Sm-EDTMP (800 MBq/kg).[88] Moreover, 2 of 10 rats (20%) treated with $^{89}$Sr (20 MBq/kg) and 3 of 15 rats (20%) treated with ifosfamide (150 mg/kg) were disease-free after 60 days.

The results indicate that the antitumour efficacy of 400 MBq/kg of the hydroxybisphosphonate 46a is similar to that of 800 MBq/kg of $^{153}$Sm-EDTMP. However, the actual dose to bone marrow is estimated to be 2.2–3.6 times as high for 800 MBq/kg $1^{53}$Sm-EDTMP as compared to 400 MBq/kg of the hydroxy-bisphosphonate 46a. Consequently, it is reasonable to assume that considerable higher doses may be delivered to tumour volumes with the novel compound as compared with currently used drugs.

A total of five novel compounds have been synthesised, labelled and evaluated for potential use in the treatment of bone-related cancer. Conditions for radiohalogenation were found which provided close to quantitative radiochemical yields in short time and with mild safe handling procedures. The labelled bisphosphonates were purified by means of HPLC and conveniently collected in non-toxic phosphate buffer.

Three compounds were found to have favourable properties as bone-seeking radiopharmaceuticals, including high affinity and selectivity for bone. Among these, two compounds became potential candidates for further evaluation. The ethylidenebisphosphonate 34a has a very high bone affinity, rapid pharmacokinetics and excellent selectivity for bone. On the other hand, the hydroxybisphosphonate 46a is superior with respect to bone affinity but the pharmacokinetics is less rapid and the selectivity poorer as compared with the bisphosphonate 34a. Eventually, bone affinity was given primary consideration and the hydroxybisphosphonate 46a was selected for further studies.

The pharmacokinetics of the hydroxybisphosphonate 46a was studied in mice by means of scintigraphy, and based on these results, estimates of doses in 'reference man' were calculated. Additionally, the antitumour efficacy of 46a was studied in tumour models of human breast cancer and osteosarcoma. Please note that the hydroxybisphosphonate 46a is referred to as compound 3h in Examples (Section A) and compound 1 in Examples (Section B).

In the breast cancer model, treatment with the bisphosphonate resulted in increased lifetime. The response was statistically significant (p<0.05) at all dose levels investigated. In comparison, repeated treatments with the chemotherapeutic agents cisplatin and doxorubicin have not improved survival nor did they have any significant effect on the metastatic growth in this model. In the osteosarcoma model, treatment with the hydroxybisphosphonate 46a resulted in a dramatic increase in lifetime. Moreover, in the group receiving the highest dose, 3 of 5 animals were long-time survivors, while all the controls developed palpable tumours.

At an administered dose level that resulted in similar survival of OHS-inoculated rats, the bone marrow dose of 46a was estimated to be less than half of that resulting from $^{153}$Sm-EDTMP. These results indicate that the antitumour efficacy of the hydroxybisphosphonate is considerably higher than that of currently used drugs.

To date, targeted radiotherapy by means of bone-seeking radiopharmaceuticals is hampered by unfavourable decay modes, unreasonable costs and limited availability. The hydroxybisphosphonate offers the advantage of a readily available radionuclide at low cost. $^{131}$I has a half-life of 8.0 days, which is convenient for handling, and decays with low energy β-particles. The decay mode is considered highly suitable for treatment of small tumours. Consequently, the bisphosphonate may find use in curative and palliative treatment of bone-related cancer. If $^{131}$I is replaced with $^{123}$I or $^{125}$I, the compound may find use for imaging as well. In conclusion, further evaluation is warranted aiming at clinical applications.

REFERENCES

1. Rubens, R. D., In *Bisphosphonates on Bones,* Bijvoet, O. L. M., Fleisch, H. A., Canfield, R. E. and Russell, R. G. G., Elsevier Sciences B.V., Amsterdam (1995) p. 337.
2. Coleman, R. E., In *Bisphosphonates on Bones,* Bijvoet, O. L. M., Fleisch, H. A., Canfield, R. E. and Russell, R. G. G., Elsevier Sciences B.V., Amsterdam (1995) P. 349.
3. Lewington, V. J., Phys. Med. Bid., 41 (1996) 2027 and references therein.
4. Pecker, C., *Univ. Calif. Pub. Pharmacol.,* 11 (1942)117.
5. Volkert, W. A. and Hoffman, T. J., *Chem Rev.,* 99 (1999) 2269.
6. Atkins, H. L., *Appl. Radiat. Isot.,* 49 (1998) 277.
7. Robinson, R., Spicer, J. A., Preston, D. F., Wegst, A. V. and Martin, N. L., *Nucl. Med. Biol.,* 14 (1987) 219.
8. Lewington, V. J., McEvan, A. J., Ackery, D. M. et al., *Eur. J. Cancer,* 27 (1991) 954.
9. Goeckeler, W. F., Edwards, B., Volkert, W. A., Holmes, R. A., Simson, J. and Wilson, D., *J. Nucl. Med.,* 28 (1987) 495.
10. Srivastava, S. C., Meinken, G. E., Richards, P., Som. P., Oster, Z. H., Atkins, H. L., Brill, A. B., Knapp, F. F. Jr., and Butler, T. A., *Int. J. Nucl. Med. Biol.,* 12 (1985) 167.
11. Maxon III, H. R., Schroder, L. E., Hertzberg, V. S., Thomas, S. R., Englaro E. E., Samaratunga, R., Smith, H., Moulton, J. S., Williams, C. C., Ehrhardt, G. J. and Schneider, H. J., *J. Nucl. Med.,* 32 (1991) 1877.
12. Eisenliut, M., J. Nucl. Med., 25 (1984) 1356.
13. Eisenhut, M., Berberich, R., Kimmig, B. and Oberhausen, E., J. Nucl. Med, 27 (1986) 1255.
14. Eisenhut, M., Fritz, P., Kimmig, B., Wingen, F. And Krempien, B., *Appl. Radiat. Isot.,* 37 (1986) 741.
15. Eisenhut, M., Barber, I. and Taylor, D. M., *Appl. Radiat. Isot.,* 38 (1987)535.
16. Larsen, R. H. and Bruland, Ø., *J. Labelled. Cpd. Radiopharm.,* 41 (1998) 823; See also: U.S. Pat. No. 5,089,249 (1991).
17. Larsen, R. H., Murud, K. M., Akabani, G., Hoff, P., Bruland, 0. and Zalutsky, M. R., *J. Nucl. Med.,* 40 (1999) 1197.
18. Zweit, *J. Phys. Med Biol.,* 41 (1996) 1905.
19. Howell, R. W., Rao, D. V. and Sastiy, K. S., *Med. Phys.,* 16 (1989) 66.
20. Zanzonico, P. B., *Thyroid,* 7 (1997) 199.
21. Beckers, C., *Thyroid,* 7 (1997) 221.
22. Castronovo, F. P. Jr., Beh, R. A., Veillux, N. M., *J. Nucl. Med. Technology,* 10 (1982) 157.
23. Humm, J. L. and Cobb, L. M., *J. Nucl. Med.,* 31 (1990) 75.
24. Vaidyanathan, G. and Zalutsky, M. R., *Phys. Med. Biol.,* 41, (1996) 1915.
25. Hassfjell, S. P., Bruland, Ø. and Hoff, P., *Nucl. Med. Biol.,* 24 (1997) 231.
26. Papapoulus, S. E., In *Bisphosphonates on Bones,* Bijvoet, O. L. M., Fleisch, H. A., Canfield, R. E. and Russell, R. G. G., Elsevier Sciences B.V., Amsterdam (1995) p. 231.
27. Li, C. and Yuan, C., *Tetrahedron Lett.,* 34 (1993) 1515.
28. Texier-Boullet, F. and Foucaud, A., *Synthesis,* (1982) 165.
29. Sekine, M., Nakajima, M., Kume, A., Hashizume, A. and Hata, T., *Bull. Chem. Soc. Jpn.,* 55 (1982) 224 and references therein.
30. Myers, T. C., Preis, S. and Jensen, E. V., *J. Am. Chem. Soc.,* 76 (1954), 4172; Harvey, R. G., Myers, T. C., Jacobson, H. I. and Jensen, E. V., *J. Am. Chem. Soc.,* 79 (1957) 2612.

31. Oae, S., Fukumoto, T. and Kiritani, R., *Bull. Chem. Soc. Jpn.*, 36 (1963)346.
32. Kornblum, N., Jones, W. J. and Anderson, G. J., *J. Am. Chem. Soc.*, 81 (1959) 4113.
33. Pudovik, A. N. and Zimin, M. G., *Pure & Appl. Chem.*, 52 (1980) 989 and references therein.
34. Teulade, M. P. and Savignac, P., *J. Org. Met. Chem.*, 304 (1986) 283.
35. McKenna, C. E., Higa, M. T., Cheung, N. H. and McKenna, M. C., *Tetrahedron Lett.*, (1977) 155.
36. Coenen, H. H., Moerlein, S. M. and Stöcklin, G., *Radiochimica Acta*, 34 (1983) 47 and references therein.
37. Moerlein, S. M. and Coenen, H. H., *J. Chem. Soc. Perkin Trans. I.*, (1985) 1941.
38. Seevers, R. H. and Counsell, R. E., *Chem. Rev.*, 82 (1982) 575.
39. Vaidyanathan, G. and Zalutsky, M. R., *Appl. Radiat. Isot*, 44 (1993) 621.
40. Clark, H. A., Gordon, A. F., Young, C. W. and Hunter, M. J., *J. Am. Chem. Soc.*, 73 (1951) 3798.
41. Effenberger, F. And Habich, D., *Liebigs. Am. Chem.*, (1979) 842. See also Habich, D. and Effenberger, F., *Synthesis*, (1979) 841.
42. Ramsden, H. E., Balint, A. E., Whitford, W. R., Walburn, J. J. and Cserr, R., *J. Org. Chem. Soc.*, 22 (1957) 1202.
43. Severson, R. G., Rosscup, R. J., Lindberg, D. R. and Engberg, R. D., *J. Am. Chem. Soc.*, 79 (1957) 6540.
44. Reeves, W. P. and White, M. R., *Synth. Corn.*, 6 (1976) 193.
45. Comish, A. J. and Eaborn, C., *J. Chem. Soc. Perkin Transac. II*, (1975) 874.
46. Berlin, K. D., Hellwege, D. M. and Nagabhushanam, M., *J. Org. Chem. Soc.*, 30 (1965) 1265.
47. McConnell, R. L. and Coover, H. W. Jr., *J. Am. Chem. Soc.*, 78 (1956) 4450.
48. Fitch, S. J. and Moedritzer, K., *J. Am. Chem. Soc*, 84 (1962) 1876.
49. Nicholson, D.A. and Vaughn, H., *J. Org. Chem.*, 36 (1971) 3843.
50. Engel, R., *Organic Reactions*, 36 (1988) 175.
51. Genet, J. P., Mallart, S., Greck, C. and Piveteau, E., *Tetrahedron Lett.*, 32 (1991) 2359.
52. Itsuno, S., Sakurai, Y. and Ito, K., *Synthesis*, (1988) 995.
53. Suzuki, F., Fujikawa, y., Yamamoto, S., Mizutani, H., Oya, I., Ikai, T. and Oguchi, T., *Ger. Offen.* 2831578 (1979); Takeuchi, M., Sakamoto, S., Yoshida, M., Abe, T. and Isomura, Y., *Chem. Pharm. Bull.*, 41 (1993) 688 and references therein.
54. Trost, B. M. and Curran, D. P., *Tetrahedron Lett.*, 22 (1981) 1287.
55. Trost, B. M., Arndt, H. C., Strege, P. E. and Verhoeven, T. R., *Tetrahedron Lett.*, (1976) 3477.
56. Leonard, J., Lygo, B. and Procter, G., *Advanced practical organic chemistry*, Blackie Academic & Professional, New York, p.102.
57. Crossland, R. K. and Servis, K. L., *J. Org. Chem.*, 35 (1970) 3195.
58. Doyle, M. P. and Bryker, W. J., *J. Org. Chem.*, 44 (1979) 1572.
59. Berei, K. and Vasros, L., In *The Chemistry of Functional Groups, Supplement D*, Patai, S. and Rappoport, Z., (1983) John Wiley & Sons Ltd, p. 405.
60. Maeda, M., Komori, H., Dohmoto, H. and Kojima, M., *J. Labelled Cpd. Radiopharm.*, 22 (1985) 487 and references therein.
61. Foster, N. I., Dannals, R., Bums, H. D. and Heindel, N. D., *J. Radioanal. Chem.*, 65 (1981) 95.
62. Barrio, J. R., Satyamurthy, N., Ku, H. and Phelps, E., *J. Chem. Soc., Chem. Commun.*, (1983) 443.
63. Ku, H. and Barrio, J. R., *J. Org. Chem.*, 46 (1981) 5239.
64. Satyamurthy, N. and Barrio, J. R., *J. Org. Chem.*, 48 (1983) 4394.
65. Eabom, C., *J. Org. Met. Chem.*, 100 (1975) 43.
66. Wilbur, D. S., Anderson, K. W., Stone, W. E. and O'Brian, H. A., *J. Labelled. Cpd. Radiopharm.*, 19 (1982) 1171 and references therein.
67. Effenberger, F. and Spiegler, W., *Angew. Chem. Int. Ed. Engl.*, 20 (1981) 265.
68. Hamilton, J. G. J., *Appl. Phys.*, 12 (1941) 441.
69. Hoff, P., *Acta Physica Polonica B*, 31 (2000) 33.
70. Lambrecht, R. M. and Mirzadeh, S., *J. Appl. Radiat. Isot.*, 36 (1985) 443 and references therein.
71. Nefedov, V. D., Norseev, Yu. V., Toropova, M. A. and Khalkin, V. A., Russ. *Chem. Rev.*, 37 (1968)87; Visser, G. W. M., *Radiochimica Acta*, 47 (1989) 97.
72. Vaidyanathan, G. and Zalutsky, M. R., *Bioconjugate Chem.*, 3 (1992) 499.
73. Doberenz, V., Dang, D. N., Dreyer, R., Milanov, M., Norseyev, Y. V. and Hkalkin, V. A., *Radiochem. Radioanal. Lett.*, 52 (1982) 119. See also Schwarz, U. P., Plascjak, P., Beitzel, M. P., Gansow, O. A., Eckelman, W. C. and Waldmann, T. A., *Nucl. Med & Biol.*, 25 (1998) 89.
74. Wiedmer, W. H., Zbinden, A. M., Trechsel, U. and Fleisch, H., *Calcif. Tissue Int.*, 35 (1983) 397.
75. Hendriksen, G., Messelt, S. Olsen, E. and Larsen, R. H., *Appl. Radiat. Isot.*, in press.
76. Larsen, R. H., Wieland, B. W. and Zalutsky, M. R., *Appl. Radiat. Isot.*, 47 (1996) 135.
77. Zalutsky, M. R. and Narula, A. S., *Appl. Radiat. Isot.*, 38 (1987) 1051.
78. Ebetino, F. H. and Dansereau, S. M., In *Bisphosphonates on Bones*, Bijvoet, O. L. M., Fleisch, H. A., Canfield, R. E. and Russell, R. G. G., Elsevier Sciences B.V., Amsterdam (1995) p. 139.
79. Leyvraz, S., Hess, U., Flesch, G., Bauer, J., Hauffe, S., Ford, J. M. and Burckhardt, P., *J. Natl. Cancer. Inst.*, 84 (1992) 788.
80. Dedrick, R. L., Bischoff, K. B. and Zaharko, D. S., *Cancer Chem. Reports Part* 1, 54 (1970) 95.
81. Eary, J. F., Collins, C., Stabin, M., Vernon, C., Petersdorf, S., Baker, M., Hartnett, S., Ferency, S., Addison, S. J., Appelbaum, F. and Gordon, E. E., *J. Nucl. Med.*, 34 (1993) 1031.
82. Howell, R. W., Narra, V. R. and Ra, D. V., *J. Nucl. Med*, 33 (1992) 277.
83. Engebraaten, Ø. and Fodstad, Ø., *Int. J. Cancer*, 82 (1999) 219.
84. Ree, A. H., Tvermyr, M., Engebraaten, O, Rooman, M., Røsok, Ø., Hovig, E., Meza-Zepeda, L. A., Bruland, Ø. And Fodstad, Ø., *Cancer Research*, 59 (1999) 4675.
85. Naundorf, H., Rewasowa, E. C., Fichtner, I., Büttner, B., Becker, M. and Görlich, M., *Breast Cancer Research and Treatment*, 23 (1992) 87.
86. Kjønniksen, I., Winderen, M., Bruland, Ø. And Føodstad, Ø., *Cancer Research*, 54 (1994) 1715.
87. Fodstad, Ø., Brøgger, A., Bruland, Ø., Solheim, Ø. P., Nesland, J. M. and Pihl, A., *Int. J. Cancer*, 38 (1986) 33.
88. Winderen, M., Kjønniksen, I. and Fodstad, Ø., *Journal of the National Cancer Institute*, 87 (1995) 221.
89. Royal Society/Universities federation for animal welfare (UFAW, 1987).
90. United Kingdom Coordinating Committee on Cancer Research (UKCCCR), *Br. J. Cancer.*, 58 (1988) 156.

What is claimed is:

1. A pharmaceutical compound, or pharmaceutically acceptable salt thereof, for use in medicine, wherein said compound is of formula I R—Ar—X—Y  I wherein
   R comprises a radiolabel selected from the group consisting of $^{123}$I, $^{124}$I, $^{125}$I, $^{131}$I, $^{211}$At, $^{186}$Re, Tc-99m, and β-emitting bromine nuclei;
   Ar is an aromatic moiety;
   X is a linker group; wherein X is selected from the group consisting of: a substituted or unsubstituted $C_{1-4}$ alkylene group, a substituted or unsubstituted $C_{1-4}$ amine group, a substituted or unsubstituted $C_{1-4}$ ether group, a substituted or unsubstituted $C_{1-4}$ thioether group, S=O and $SO_2$; and
   Y is a geminal bisphosphonic acid group,
with the proviso that when X is a substituted or unsubstituted $C_{1-4}$ alkylene group, X is meta to R.

2. A compound according to claim 1 wherein said compound is of formula II

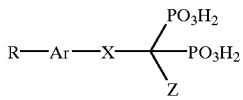

and wherein Z is H, $NH_2$ or an oxy substituent.

3. A compound according to claim 2 wherein Z is H or OH.

4. A compound according to claim 1 wherein X is a substituted or unsubstituted $C_{1-4}$ alkylene group.

5. A compound according to claim 1 wherein X is a $C_{1-4}$ amine group, $C_{1-4}$ ether group or a $C_{1-4}$ thioether group, each of which may be substituted or unsubstituted.

6. A compound according to claim 1 wherein X is S=O or $SO_2$.

7. A compound according to claim 1 wherein said aromatic moiety is a single aromatic ring.

8. A pharmaceutical composition comprising a compound according to claim 1 admixed with a pharmaceutically acceptable carrier, diluent, or excipient.

9. A method of treating a subject in need of treatment of bone disorders, the method comprising administering to said subject a therapeutically effective amount of a compound according to claim 1.

10. A method of treating a subject in need of treatment of breast cancer, the method comprising administering to said subject a therapeutically effective amount of a compound according to claim 1.

11. A compound according to claim 1 wherein said aromatic moiety is selected from the group consisting of phenyl, napthyl, thiophenyl, furyl, pyridyl, and pyrrole.

12. A compound according to claim 4 wherein X is substituted.

13. A compound according to claim 5 wherein X is an amine group.

14. A compound according to claim 1 wherein the radiolabel is $^{131}$I.

15. A compound according to claim 1 wherein the radiolabel is $^{186}$Re.

16. A compound according to claim 1 wherein the radiolabel is Tc-99m.

17. A compound according to claim 1 wherein said X group is meta to said R group.

18. A compound according to claim 1 which has the formula

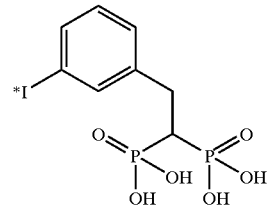

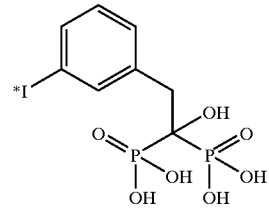

or a pharmaceutically acceptable salt of either compound, wherein I* represents $^{123}$I, $^{124}$I, $^{125}$I, or $^{131}$I.

19. A compound according to claim 1 which has the formula

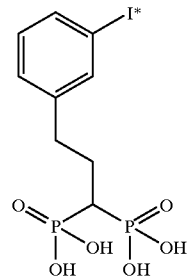

or a pharmaceutically acceptable salt thereof, wherein *I represents $^{123}$I, $^{124}$I, $^{125}$I or $^{131}$I.

20. A compound according to claim 1 which has the formula

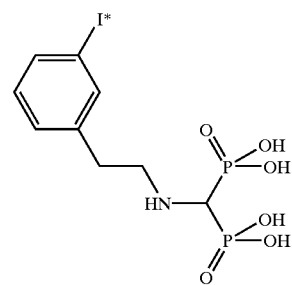

or a pharmaceutically acceptable salt thereof, wherein I* represents $^{123}$I, $^{124}$I, $^{125}$I or $^{131}$I.

21. A process for preparing a compound of formula I, as defined in claim 1

R—Ar—X—Y  I wherein
   R comprises a radiolabel selected from the group consisting of $^{123}$I, $^{124}$I, $^{125}$I, $^{131}$I, $^{211}$I, $^{186}$Re, Tc-99m, and β-emitting bromine nuclei;
   Ar is an aromatic moiety;

X is a linker group; wherein X is selected from the group consisting of: a substituted or unsubstituted $C_{1-4}$ alkylene group, a substituted or unsubstituted $C_{1-4}$ amine group, a substituted or unsubstituted $C_{1-4}$ ether group, a substituted or unsubstituted $C_{1-4}$ thioether group, S=O and $SO_2$; and Y is a geminal bisphosphonic acid group;

with the proviso that when X is a substituted or unsubstituted $C_{1-4}$ alkylene group, X is meta to R;

said process comprising the following steps:

(i) preparing a phosphonate precursor comprising Ar, X and Y;

(ii) radiolabelling said phosphonate precursor.

22. A process according to claim 21 wherein step (ii) is an iododesilyation reaction.

* * * * *